(12) United States Patent
Dacosta et al.

(10) Patent No.: US 10,159,499 B2
(45) Date of Patent: Dec. 25, 2018

(54) BONE IMPLANTS AND CUTTING APPARATUSES AND METHODS

(71) Applicant: Paragon 28, Inc., Englewood, CO (US)

(72) Inventors: Albert Dacosta, Lone Tree, CO (US); Matthew S. Solar, Indialantic, FL (US); Thomas Chang, Santa Rosa, CA (US); Michael Houghton, Fort Collins, CO (US)

(73) Assignee: PARAGON 26, INC., Englewood, CO (US)

( * ) Notice: Subject to any disclaimer, the term of this patent is extended or adjusted under 35 U.S.C. 154(b) by 621 days.

(21) Appl. No.: 14/458,722

(22) Filed: Aug. 13, 2014

(65) Prior Publication Data

US 2014/0350561 A1    Nov. 27, 2014

Related U.S. Application Data

(63) Continuation-in-part of application No. 14/110,536, filed as application No. PCT/US2012/032765 on Apr. 9, 2012, now Pat. No. 9,452,057.

(Continued)

(51) Int. Cl.
    *A61B 17/16*    (2006.01)
    *A61B 90/00*    (2016.01)

(52) U.S. Cl.
    CPC ...... *A61B 17/1682* (2013.01); *A61B 17/1633* (2013.01); *A61B 2090/08021* (2016.02); *Y10T 29/49826* (2015.01)

(58) Field of Classification Search
    CPC ............ B23B 2240/32; B23B 2240/36; A61B 17/1666; A61B 17/1682; A61B 17/1684
    See application file for complete search history.

(56) References Cited

U.S. PATENT DOCUMENTS 5,021,056 A    6/1991  Hofmann et al.
8,876,444 B1 * 11/2014 Chanturidze ......... B23B 49/005
                                              408/191

(Continued)

FOREIGN PATENT DOCUMENTS

WO    9729704 A1    8/1997

OTHER PUBLICATIONS

International Preliminary Report on Patentability for PCT application No. PCT/US2012/032765 dated Oct. 8, 2013, 8 pages.

(Continued)

*Primary Examiner* — Samuel Hanna
(74) *Attorney, Agent, or Firm* — Heslin Rothenberg Farley & Mesiti, P.C.

(57) ABSTRACT

Reamer sleeves, reamer assemblies, and methods of assembling the reamer assemblies are disclosed. The reamer sleeves include a base portion with a top surface and a bottom surface and a securement mechanism extending away from the top surface of the base portion. The securement mechanism includes an opening, at least one engagement member adjacent the opening, and at least one engagement protrusion extending away from the engagement member into the opening. The opening extends through the securement mechanism to the bottom surface of the base portion. The bone reamer assembly including a reamer and a reamer sleeve removably coupled to the reamer. The reamer including a shaft with a first and second end, a cutting member coupled to the second end of the shaft, and a groove near the second end of the shaft. A method of assembling a hard tissue reamer assembly is also disclosed.

11 Claims, 59 Drawing Sheets

Related U.S. Application Data

(60) Provisional application No. 61/473,194, filed on Apr. 8, 2011.

(56) References Cited

U.S. PATENT DOCUMENTS

| | | |
|---|---|---|
| 2002/0082604 A1 | 6/2002 | Abdelgany et al. |
| 2002/0138078 A1 | 9/2002 | Chappuis |
| 2003/0097133 A1* | 5/2003 | Green ................ A61B 17/1617 606/80 |
| 2004/0193168 A1* | 9/2004 | Long ..................... A61B 17/16 606/80 |
| 2006/0184174 A1* | 8/2006 | Harris, Jr. .......... A61B 17/1617 606/80 |
| 2007/0038303 A1 | 2/2007 | Myerson et al. |

OTHER PUBLICATIONS

International Search Report for PCT/US2012/032765 dated Oct. 25, 2012, 5 pages.

\* cited by examiner

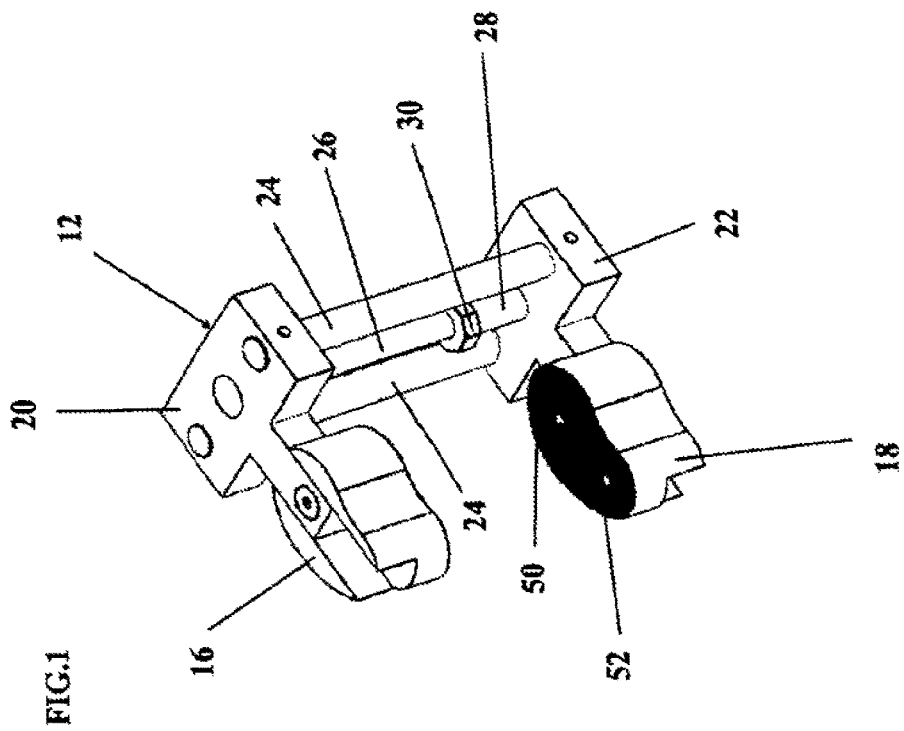
FIG.1
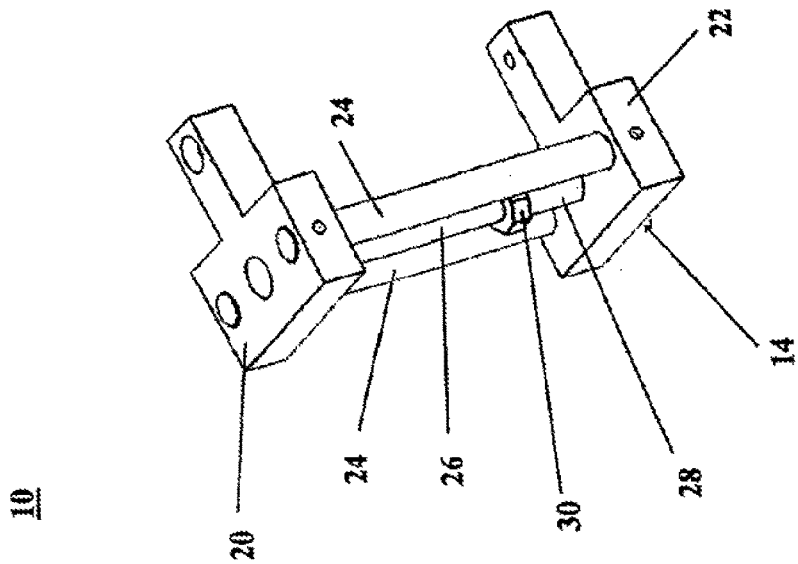

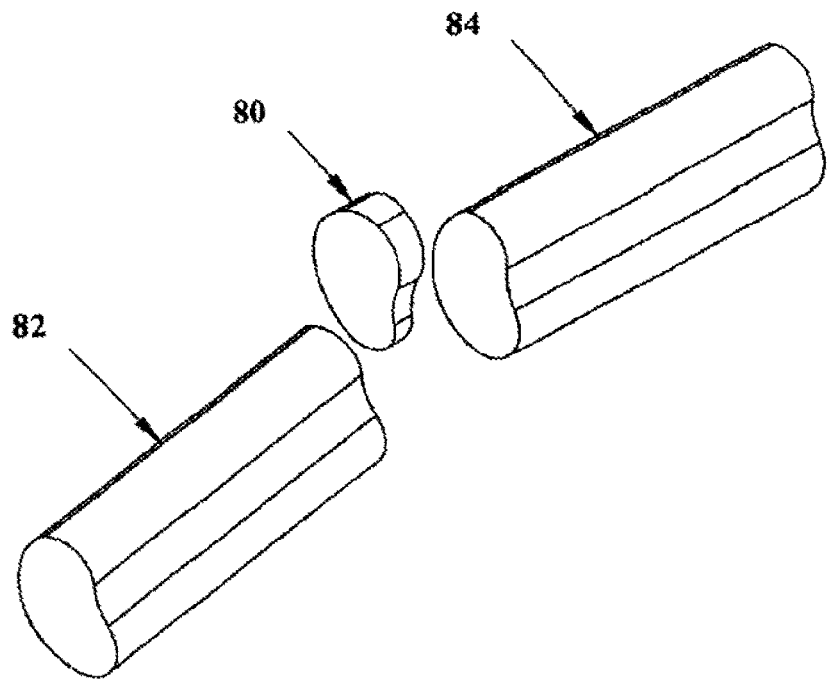
FIG. 8
FIG. 9
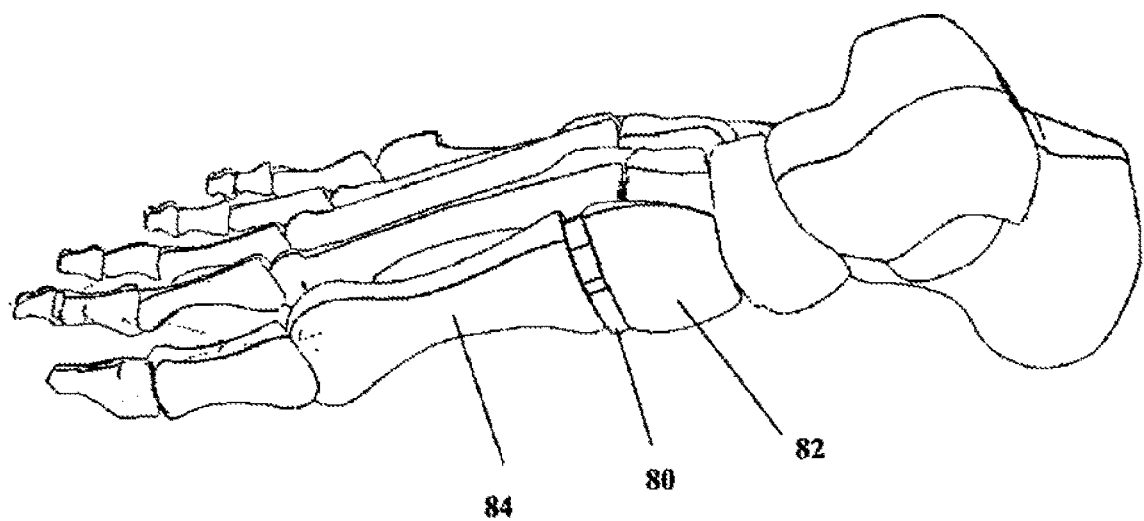

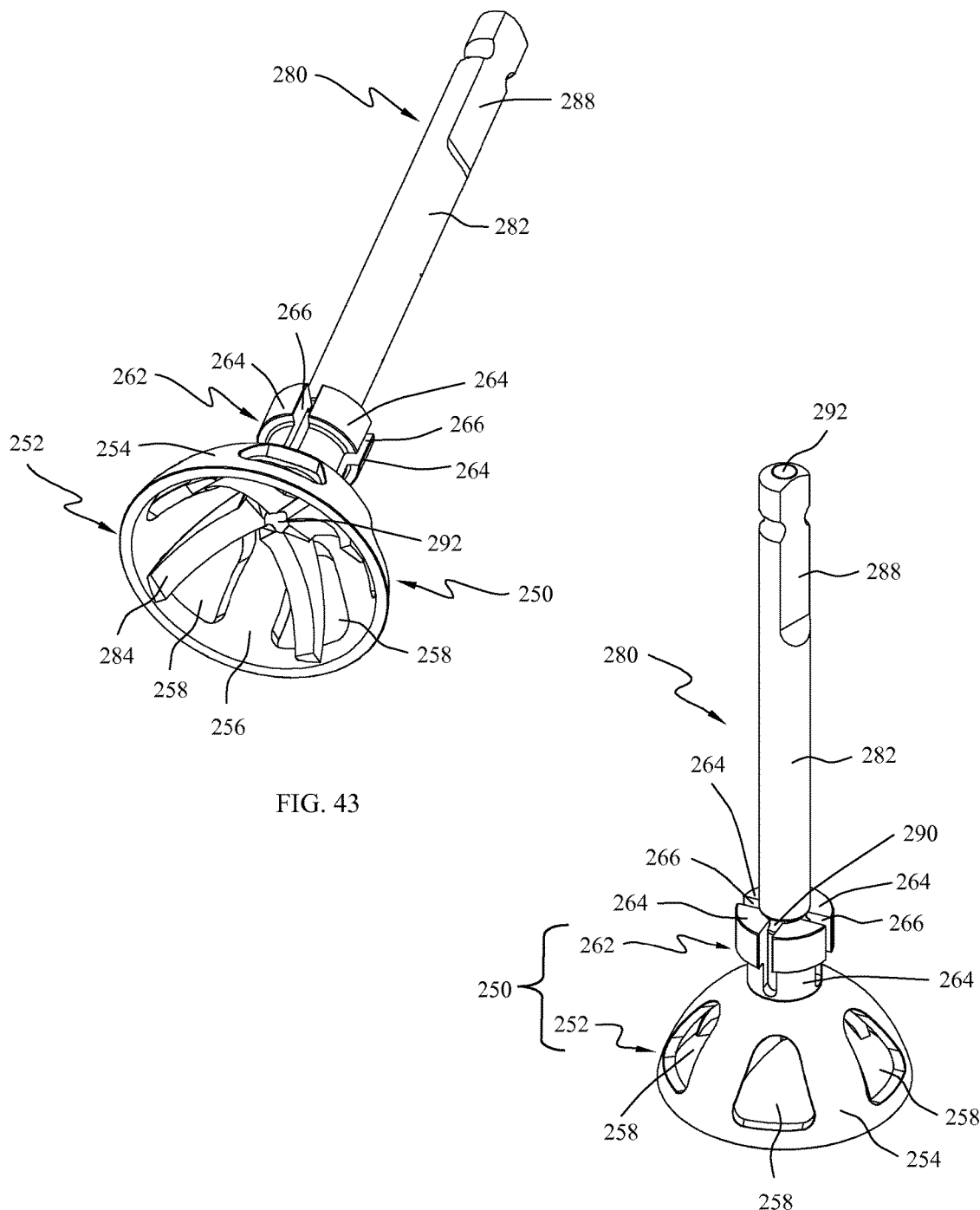

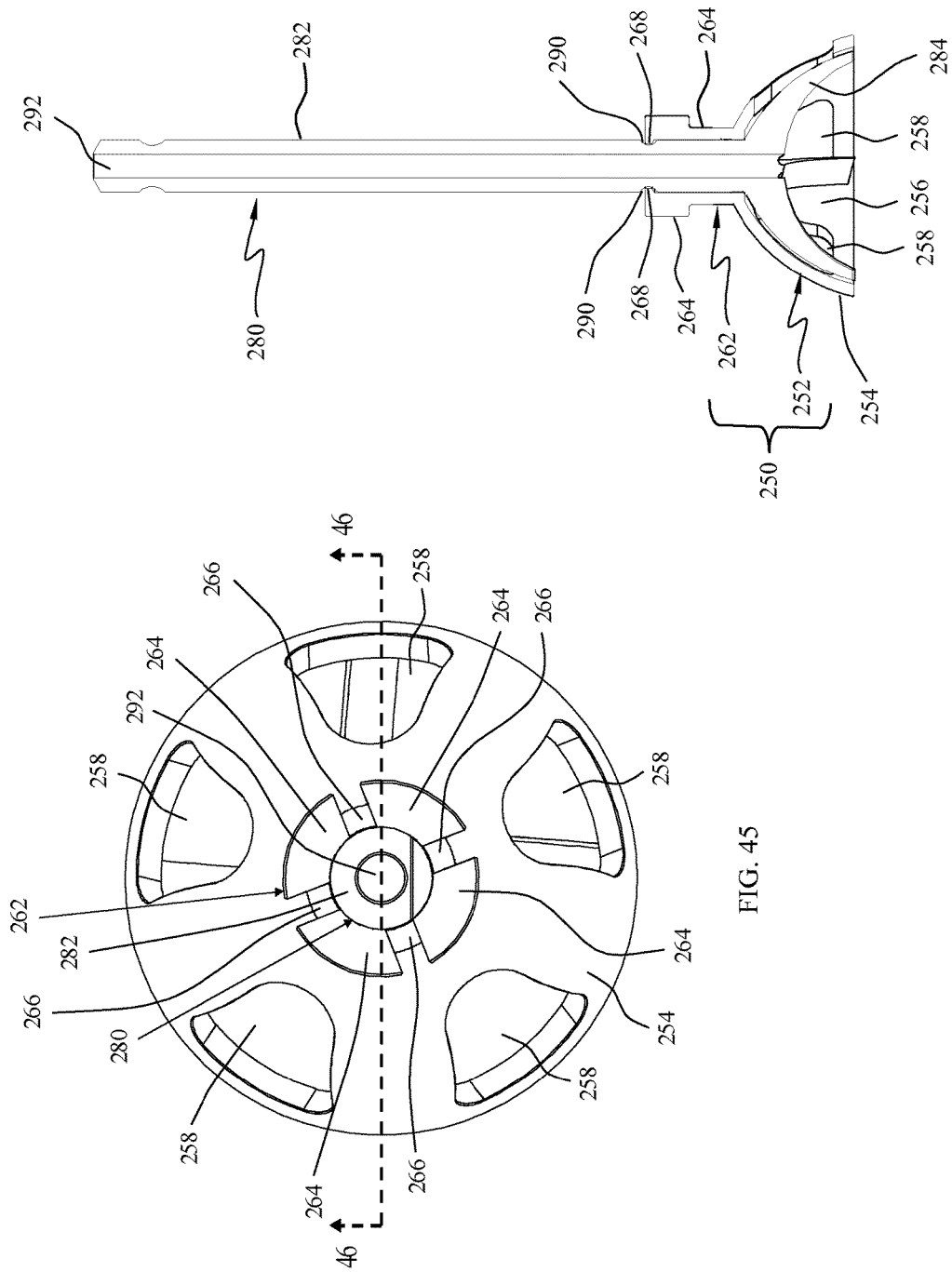

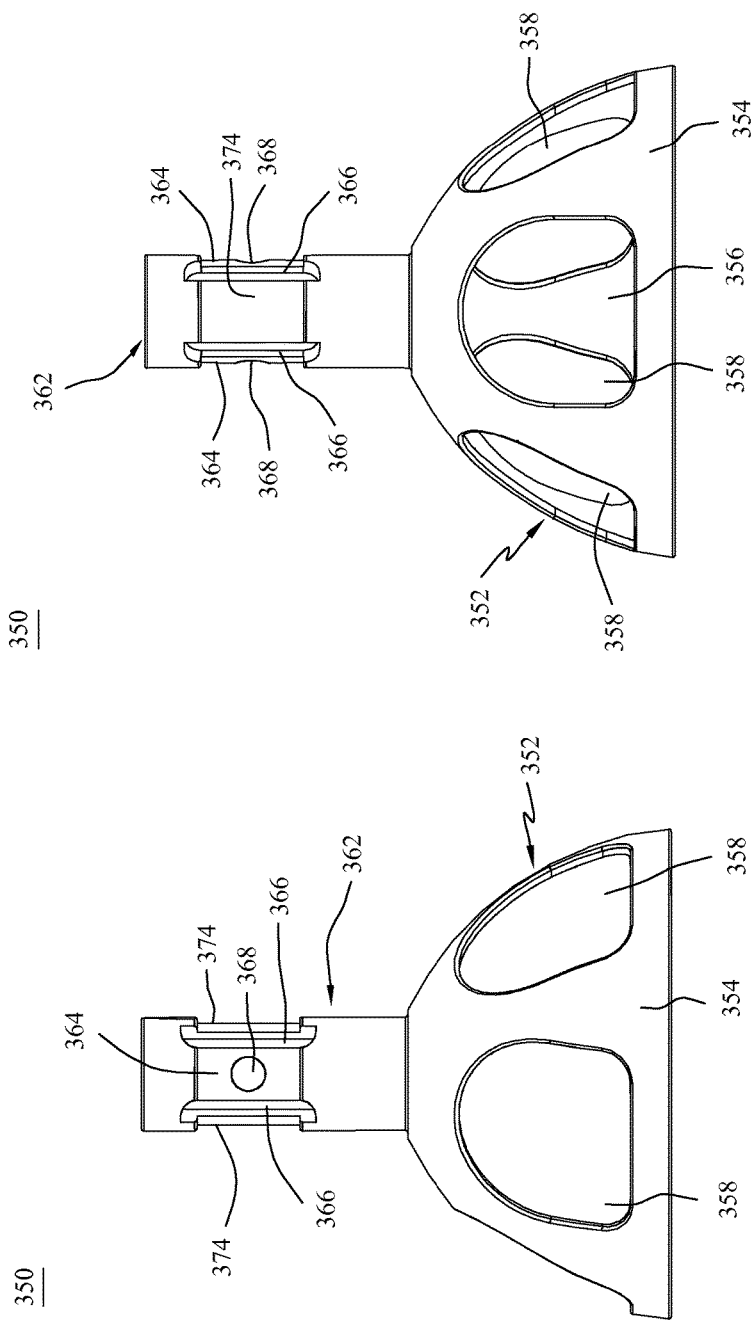

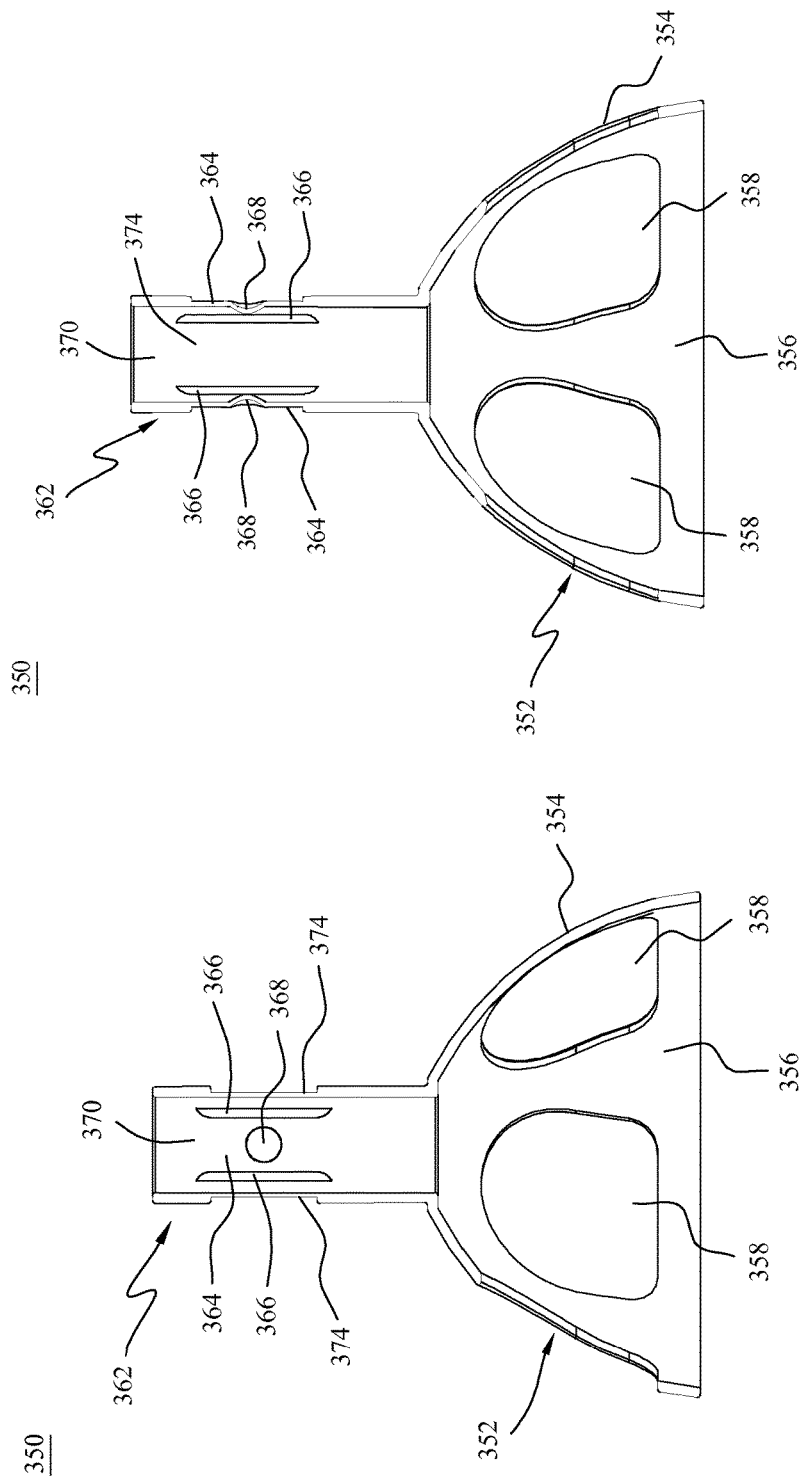

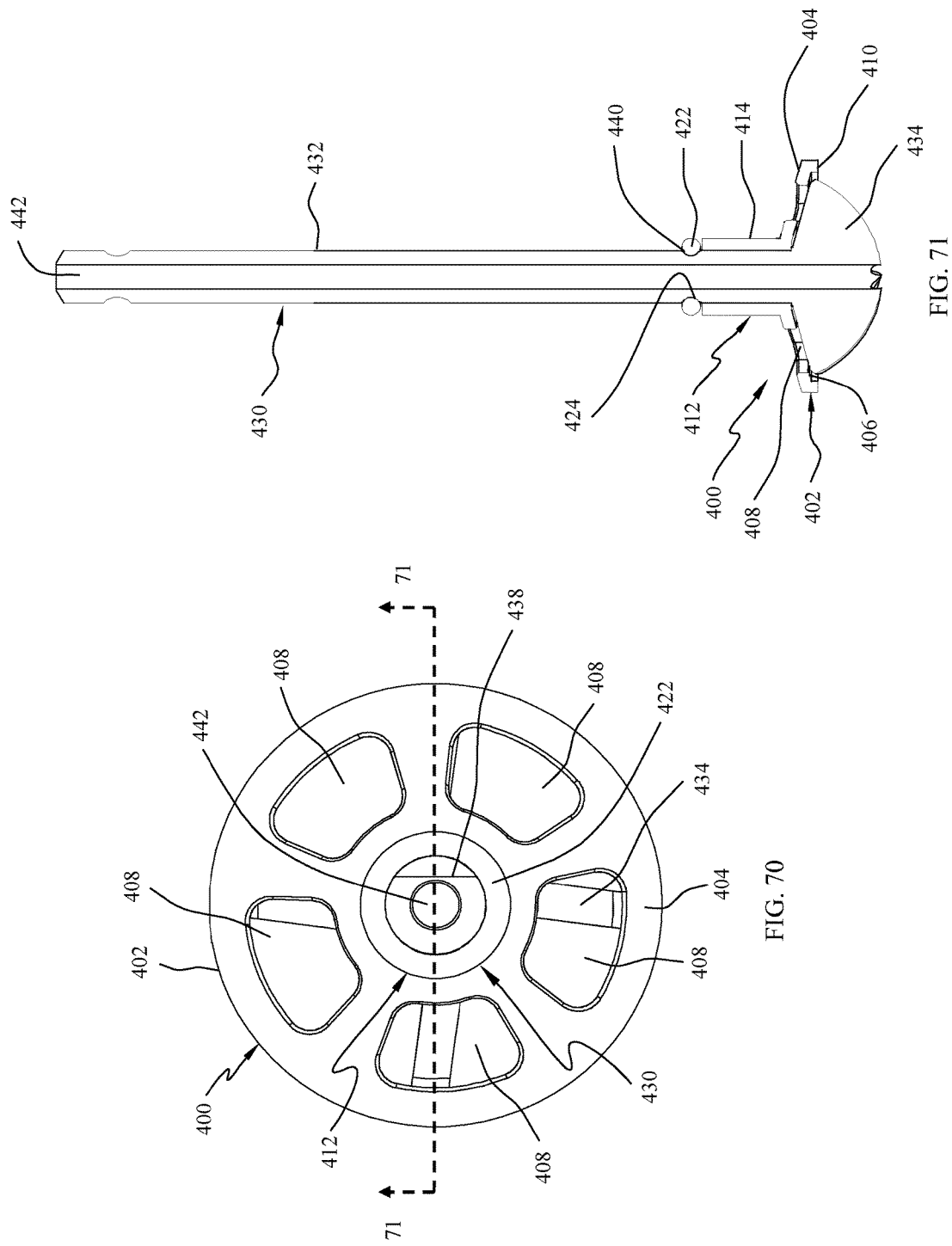

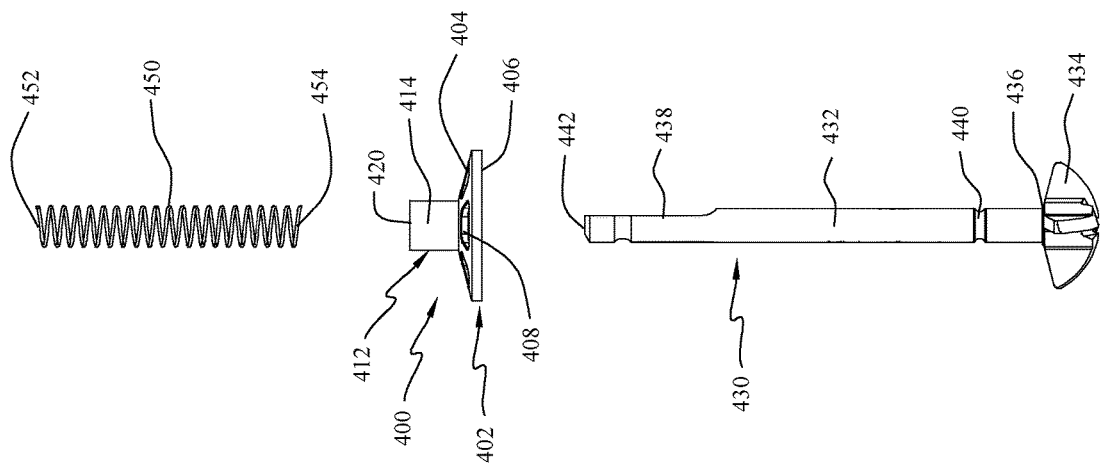
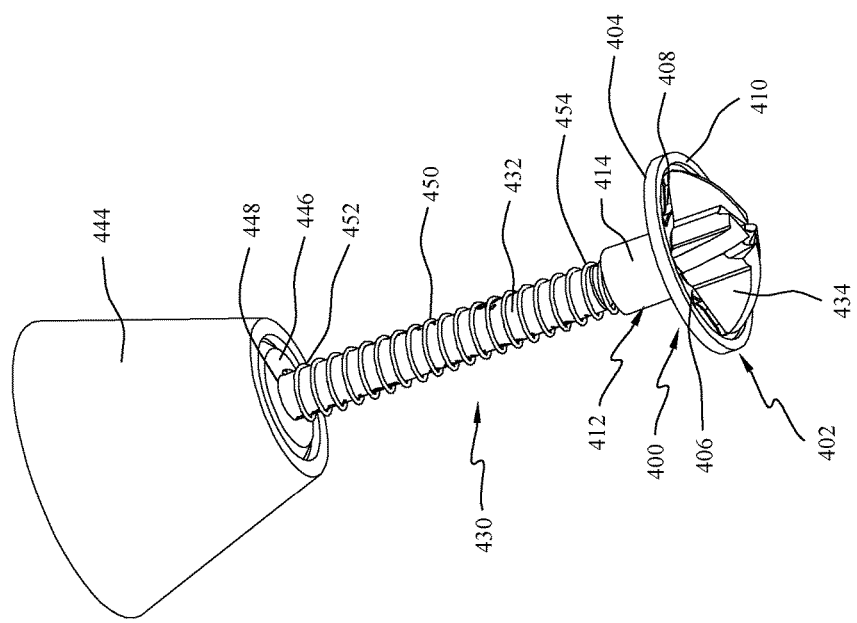

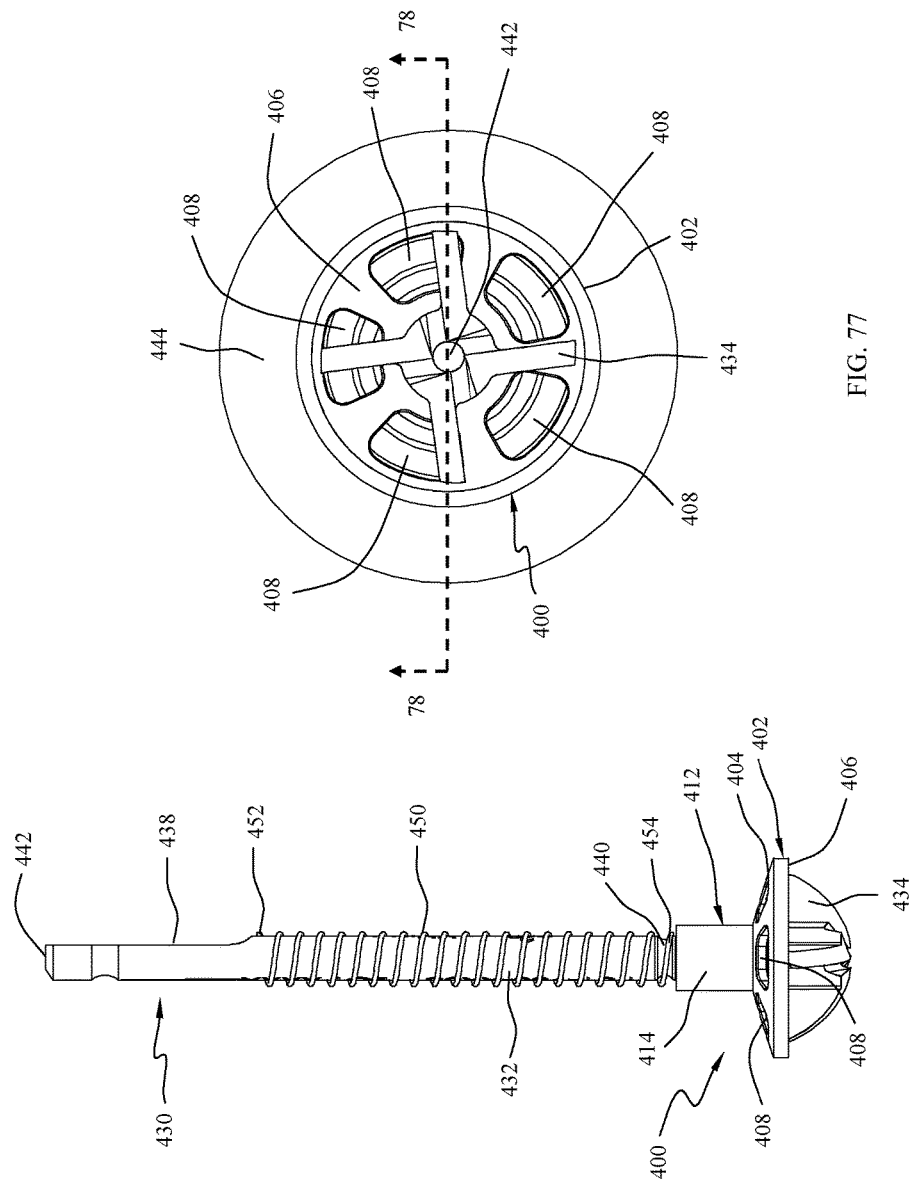

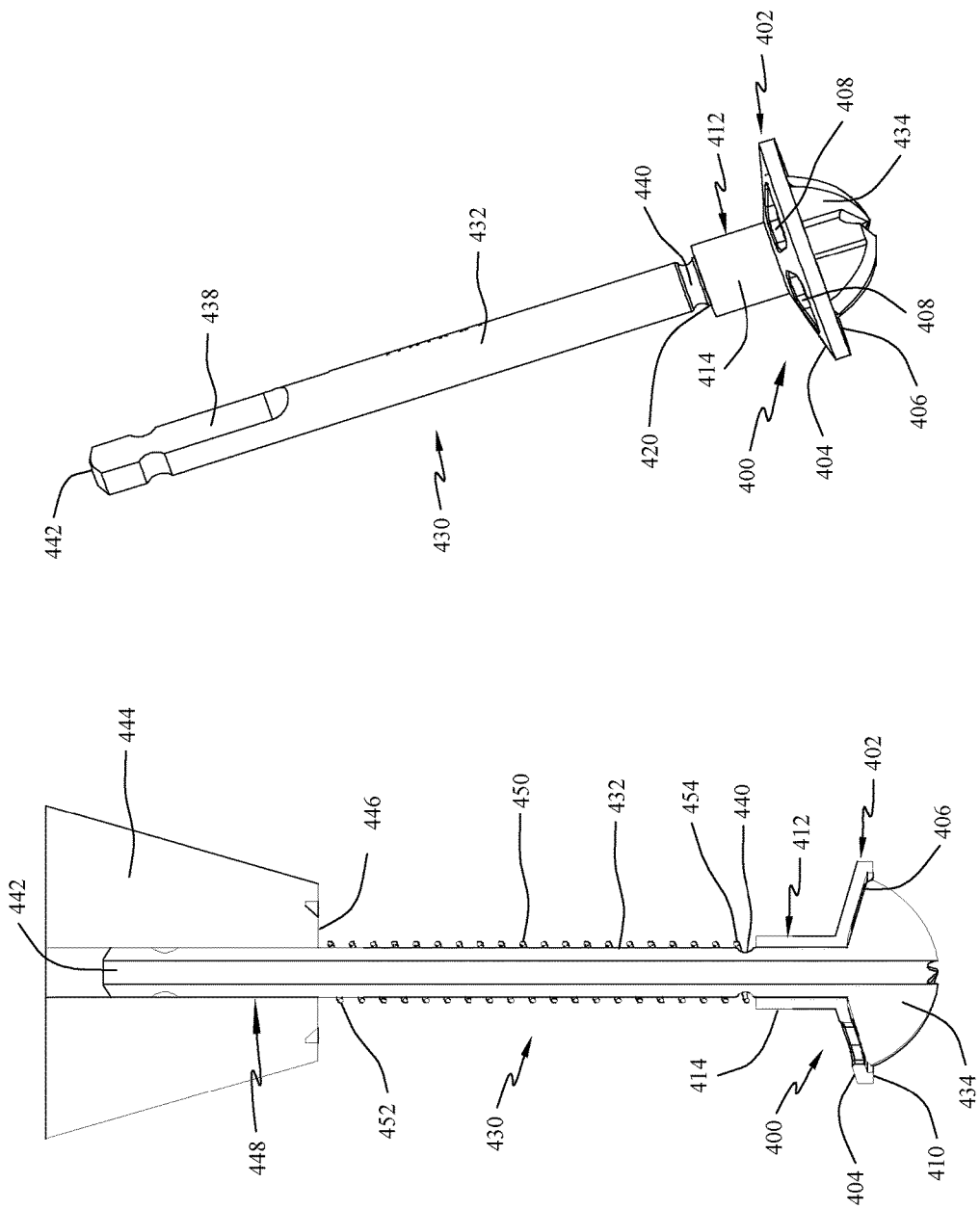

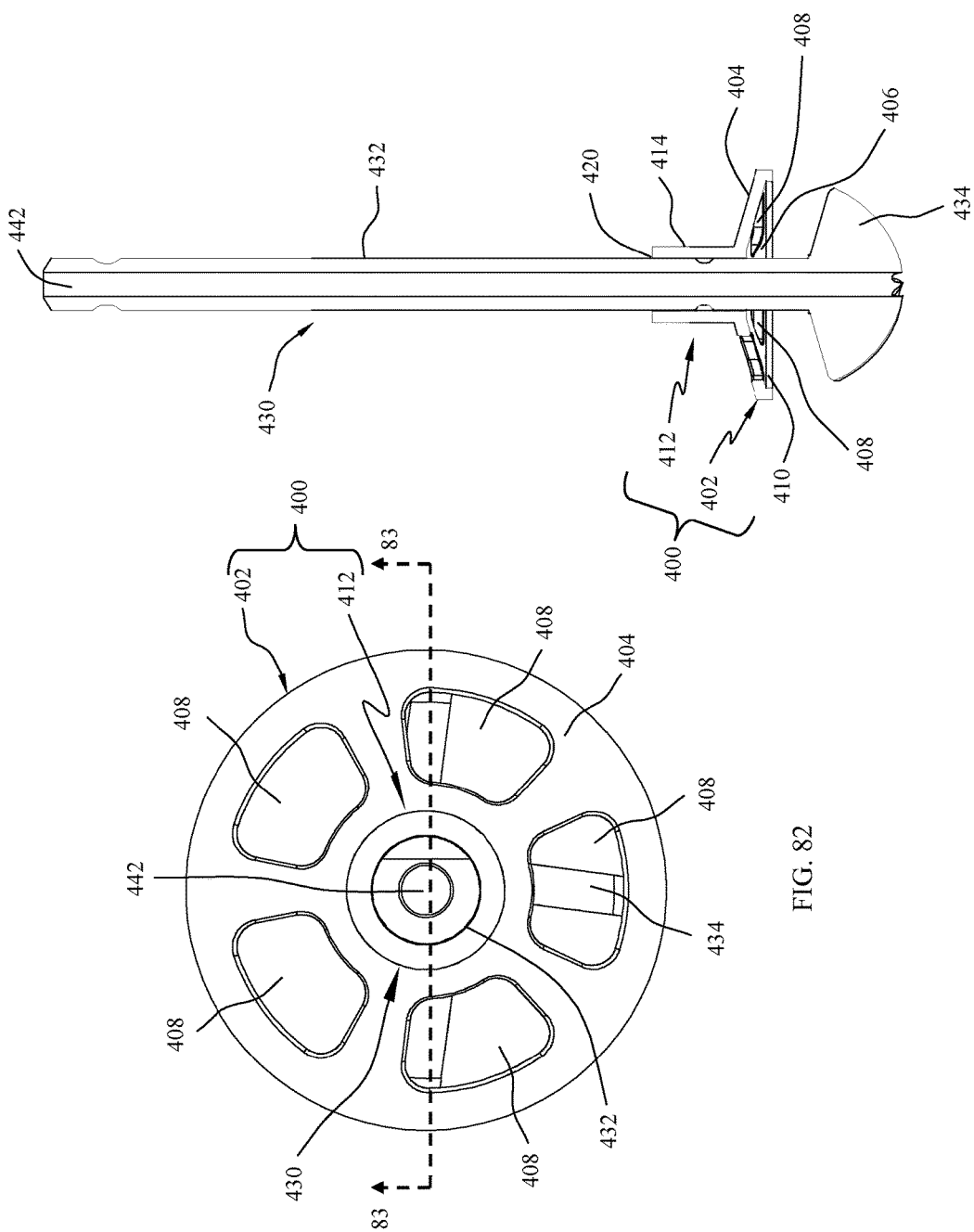

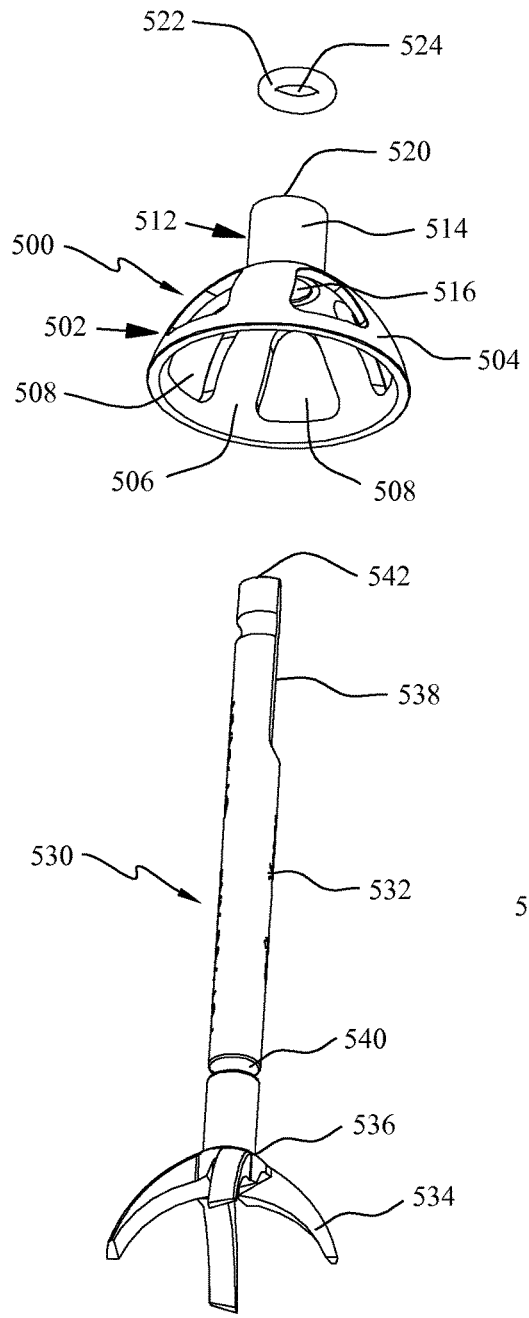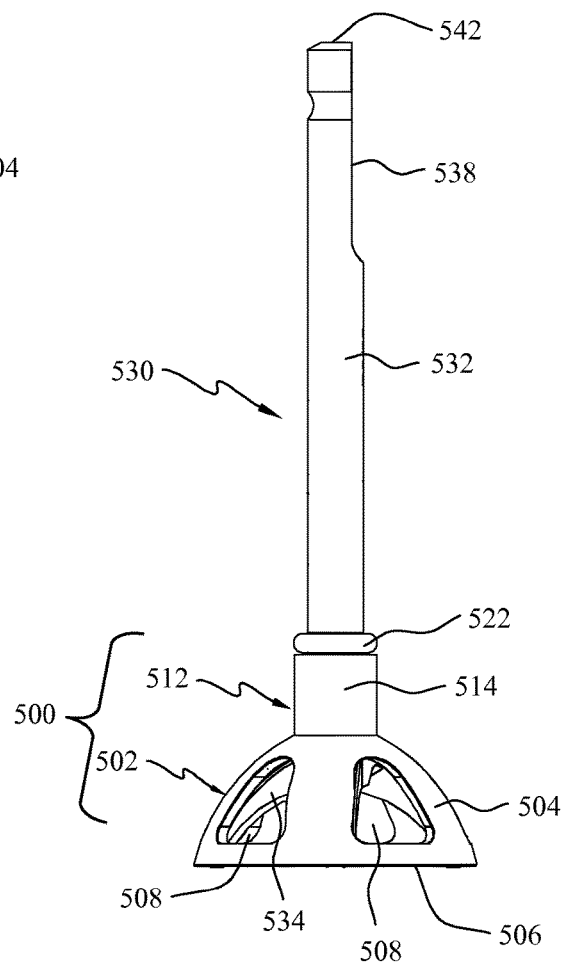
FIG. 90
FIG. 91

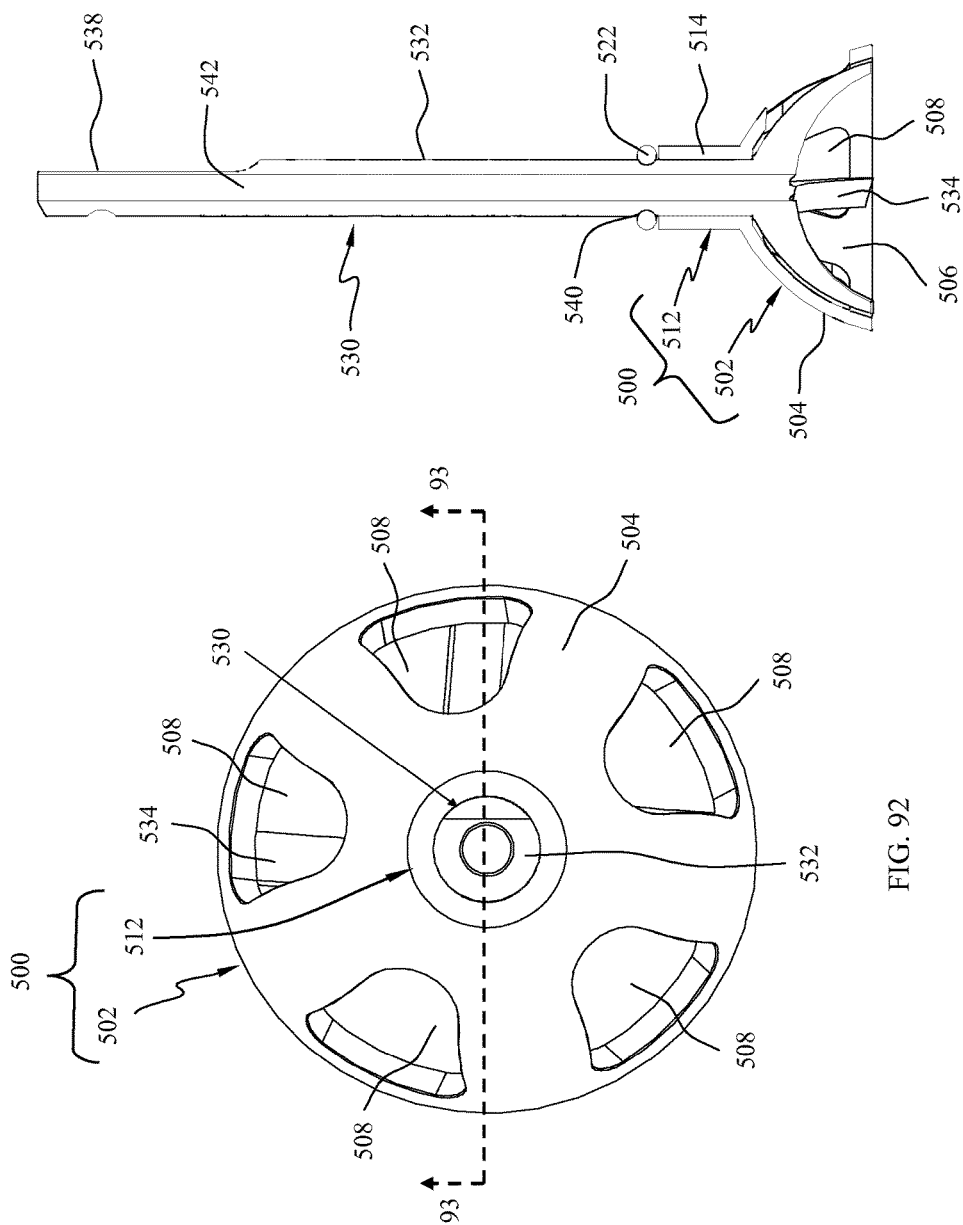

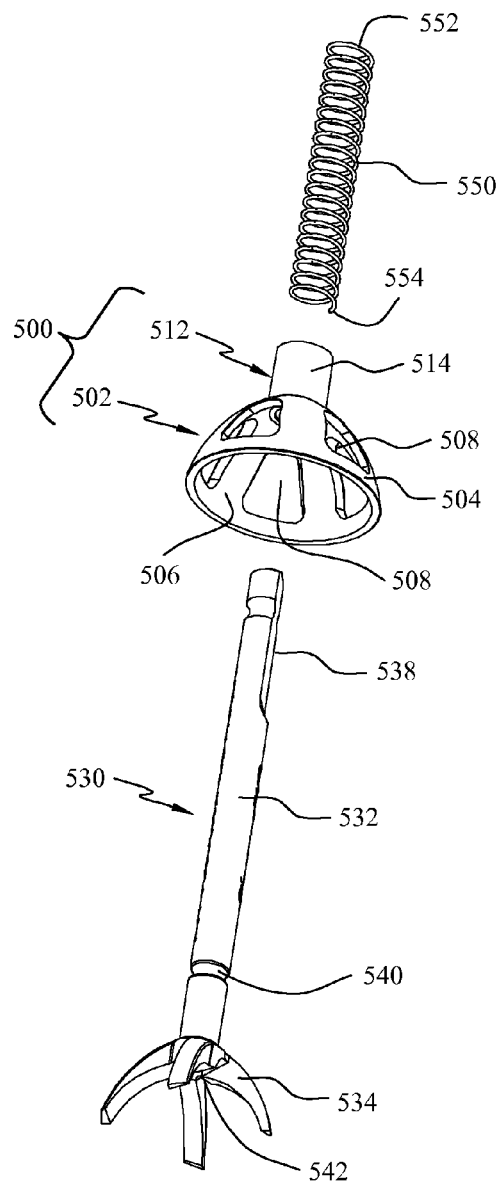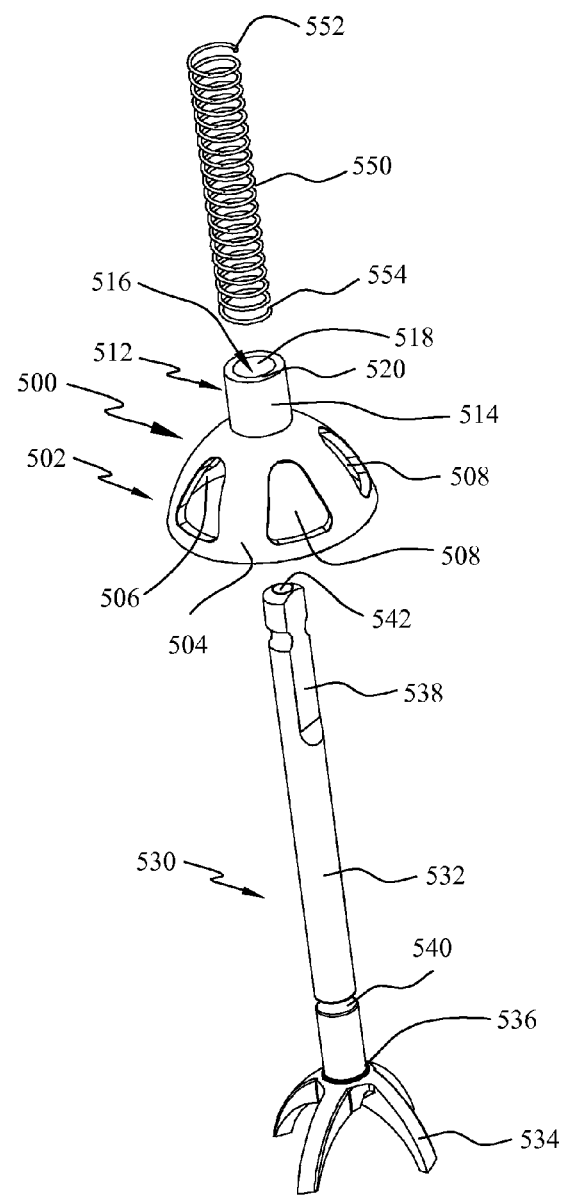
FIG. 96
FIG. 97

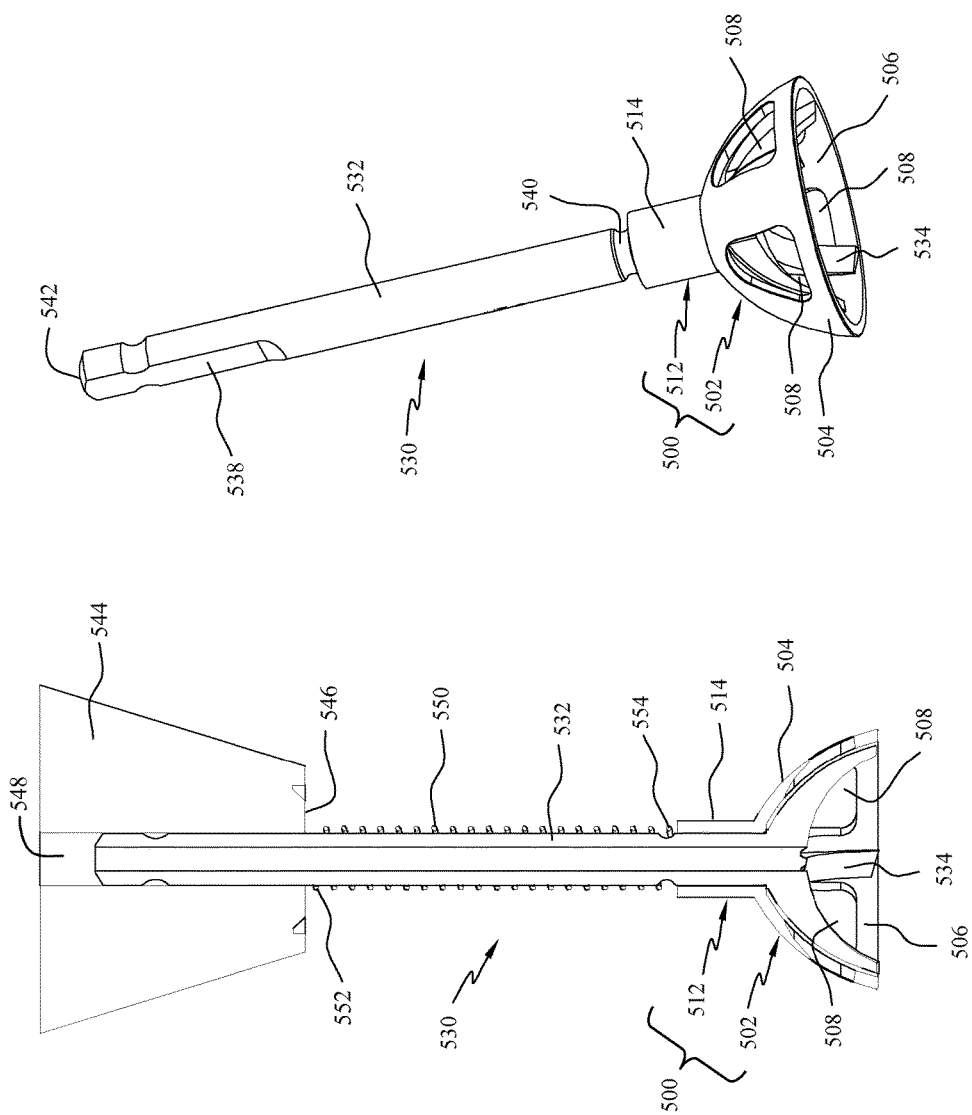

BONE IMPLANTS AND CUTTING APPARATUSES AND METHODS

CROSS-REFERENCE TO RELATED APPLICATION

This application is a continuation-in-part of U.S. application Ser. No. 14/110,536 filed on Oct. 8, 2013 which is a national stage filing under section 371 of International Application No. PCT/US2012/032765 filed on Apr. 9, 2012, and published in English on Oct. 11, 2012 as WO 2012/139114 and claims the priority benefit under 35 U.S.C. § 119(e) of U.S. provisional patent application No. 61/473,194 filed Apr. 8, 2011, each of which is hereby incorporated by reference in their entireties.

TECHNICAL FIELD

This present disclosure relates generally to the field of orthopaedics related to restoring anatomic length to joints between two bones in the upper and lower extremity following revision surgery, large deformities, injuries, and/or generally short anatomy.

BACKGROUND

The Lapidus procedure is commonly used to correct a hallux valgus deformity, which is a lateral deviation of the great toe, with subsequent hypermobility (or laxity). The Lapidus procedure is also commonly used to repair failed surgeries. Typically, a wedge of bone is removed in a biplanar direction at the distal end of the cuneiform, which will provide correction of the deformity and typically results in shortening of the great toe. The result of this shortening is a shift in weight distribution to the second ray, which can result in metatarsalgia. When the first ray is shortened the function of the patient's sesamoids may also be affected because of the change in weight distribution on the sesamoids. Currently to correct the shortening of the great toe when doing a Lapidus procedure, the accepted practice is for surgeons to make straight transverse cut on the metatarsal, then cut a wedge out of the cuneiform to obtain realignment of the intermetatarsal angle as determined by the surgeon, and insert a block of bone into the joint. The block of bone is then shaped by the surgeon until it fits within the joint. The shape of bone fails to help correct the angle. Blood supply to this joint can be limited in certain patients and using the overly processed bone makes it difficult to incorporate and heal which makes the bone prone to failure. It is well known that blood supply consideration to the joint and anatomical height and weight bearing through the joint are all concerns for healing the Lapidus procedure.

The metatarsal-phalangeal joint, when fused, is commonly denuded of cartilage by either using cup or cone reamers to minimize a loss of length and to provide versatility in final positioning or by making transverse type cuts using a saw blade. Generally, the cartilage surfaces of the metatarsal and proximal phalanx are removed and the end of the proximal phalanx is aligned with the end of the metatarsal with the two bones being fused together using screws, wires, or plates. In the case of revision surgeries of the metatarsal-phalangeal joint, the first ray may be shortened by 5-10+mm.

Accordingly, it is an object of the present invention to overcome one or more of the above-described drawbacks and/or disadvantages of the prior art. For example, in view of the deficiencies of the current implants and methods of performing the Lapidus procedure and fusion of the metatarsal-phalangeal joint, and similar implants and surgical methods for other areas of the body where multiple bone structures exist including, but not limited to, the hand, wrist and spine, it would be desirable to develop devices, instrumentation, and methods to allow a surgeon to achieve a satisfactory long term, predictable clinical outcome for these types of correction surgeries.

SUMMARY

The present invention is directed toward devices, instruments, and methods for cutting and inserting implants in the upper and lower extremity.

In one aspect of the present invention provided herein, is a reamer sleeve. The reamer sleeve includes a base portion with a top surface and a bottom surface and a securement mechanism extending away from the top surface of the base portion. The securement mechanism includes an opening extending through the securement mechanism to the bottom surface of the base portion, at least one engagement member adjacent the opening, and at least one engagement protrusion extending away from the engagement member into the opening.

In another embodiment of the present invention provided herein, is a bone reamer assembly. The bone reamer assembly includes a reamer and a reamer sleeve removably coupled to the reamer.

In another aspect of the present invention provided herein, is a method of assembling a hard tissue reamer assembly. The method includes obtaining a reamer and a reamer sleeve. The reamer includes a shaft with a first end and a second end, a cutting member coupled to the second end of the shaft, and a groove in the shaft near the second end of the shaft. The reamer sleeve includes a base portion having a top surface and a bottom surface and a securement mechanism extending away from the top surface of the base portion. The securement mechanism includes an opening extending through the securement mechanism to the bottom surface of the base portion, at least one engagement member adjacent the opening, and at least one engagement protrusion extending from the engagement member into the opening. The method further includes aligning the opening of the securement mechanism of the reamer sleeve with the shaft of the reamer. The method also includes sliding the reamer sleeve down the shaft of the reamer toward the second end and engaging the at least one engagement protrusion of the securement mechanism in the groove of the shaft of the reamer.

These and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

FIG. 1 is an isometric view of a pair of bone clamps, in accordance with an aspect of the present invention;

FIG. 8 is an isometric view of two prepared bone surfaces and the wedge shaped bone segment of FIGS. 7A-7E with an anatomical profile, in accordance with an aspect of the present invention;

FIG. 9 is a medial view of a right foot having the bone segment of FIGS. 7A-7E implanted in the foot, in accordance with an aspect of the present invention;

FIG. 43 is a bottom perspective view of the reamer assembly of FIG. 41, in accordance with an aspect of the present invention;

FIG. 44 is a top perspective view of the reamer assembly of FIG. 41, in accordance with an aspect of the present invention;

FIG. 45 is a top view of the reamer assembly of FIG. 41, in accordance with an aspect of the present invention;

FIG. 46 is a cross-sectional view of the reamer assembly of FIG. 41 taken along line 46-46 of FIG. 45, in accordance with an aspect of the present invention;

FIG. 56 is a first side view of the reamer sleeve of FIG. 54, in accordance with an aspect of the present invention;

FIG. 57 is a second side view of the reamer sleeve of FIG. 54, in accordance with an aspect of the present invention;

FIG. 60 is a cross-sectional view of the reamer sleeve of FIG. 54 taken along line 60-60 in FIG. 58, in accordance with an aspect of the present invention;

FIG. 61 is a cross-sectional view of the reamer sleeve of FIG. 54 taken along line 61-61 in FIG. 58, in accordance with an aspect of the present invention;

FIG. 70 is a top view of the reamer assembly of FIG. 66, in accordance with an aspect of the present invention;

FIG. 71 is a cross-sectional view of the reamer sleeve of FIG. 66 taken along line 71-71 in FIG. 70, in accordance with an aspect of the present invention;

FIG. 72 is a bottom perspective view of another embodiment of a reamer assembly attached to the end portion of a drill and including the reamer sleeve of FIG. 62, in accordance with an aspect of the present invention;

FIG. 73 is an exploded side view of the reamer assembly of FIG. 72, in accordance with an aspect of the present invention;

FIG. 76 is a side view of the reamer assembly of FIG. 72, in accordance with an aspect of the present invention;

FIG. 77 is a bottom view of the reamer assembly of FIG. 72, in accordance with an aspect of the present invention;

FIG. 78 is a cross-sectional view of the reamer assembly of FIG. 72 taken along line 78-78 in FIG. 77, in accordance with an aspect of the present invention;

FIG. 79 is a perspective view of another reamer assembly including the reamer sleeve of FIG. 62, in accordance with an aspect of the present invention;

FIG. 82 is a top view of the reamer assembly of FIG. 79, in accordance with an aspect of the present invention; and FIG. 83 is a cross-sectional view of the reamer assembly of FIG. 79 taken along line 83-83 in FIG. 82, in accordance with an aspect of the present invention.

FIG. 90 is an exploded bottom perspective view of the reamer assembly of FIG. 88, in accordance with an aspect of the present invention;

FIG. 91 is a side view of the reamer assembly of FIG. 88, in accordance with an aspect of the present invention;

FIG. 92 is a top view of the reamer assembly of FIG. 88, in accordance with an aspect of the present invention;

FIG. 93 is a cross-sectional view of the reamer sleeve assembly of FIG. 88 taken along line 93-93 in FIG. 92, in accordance with an aspect of the present invention;

FIG. 96 is an exploded bottom perspective view of the reamer sleeve assembly of FIG. 94, in accordance with an aspect of the present invention;

FIG. 97 is an exploded top perspective view of the reamer sleeve assembly of FIG. 94, in accordance with an aspect of the present invention;

FIG. 100 is a cross-sectional view of the reamer sleeve assembly of FIG. 94 taken along line 100-100 in FIG. 99, in accordance with an aspect of the present invention;

FIG. 101 is a perspective view of another reamer sleeve assembly including the reamer sleeve of FIG. 84, in accordance with an aspect of the present invention;

DETAILED DESCRIPTION FOR CARRYING OUT THE INVENTION

In this application, the words proximal, distal, anterior or plantar, posterior or dorsal, medial and lateral are defined by their standard usage for indicating a particular part or portion of a bone or prosthesis coupled thereto, or directional terms of reference, according to the relative disposition of the natural bone. For example, "proximal" means the portion of a bone or prosthesis nearest the torso, while "distal" indicates the portion of the bone or prosthesis farthest from the torso. As an example of directional usage of the terms, "anterior" refers to a direction towards the front side of the body, "posterior" refers to a direction towards the back side of the body, "medial" refers to a direction towards the midline of the body and "lateral" refers to a direction towards the sides or away from the midline of the body. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices, instrumentation and methods are described herein with reference to use with the bones of the foot, the bones of the foot, ankle and lower leg may be used to describe the surfaces, positions, directions or orientations of the devices, instrumentation and methods. Further, the devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the devices, instrumentation and methods, and the aspects, components, features and the like thereof, described herein with respect to the right foot may be mirrored so that they likewise function with the left foot. Further, the devices, instrumentation and methods, and the aspects, components, features and the like thereof, disclosed herein are described with respect to the foot for brevity purposes, but it should be understood that the devices, instrumentation, and methods may be used with other bones of the body having similar structures, for example the upper extremity, and more specifically, with the bones of the wrist, hand, and arm.

Figure 2:
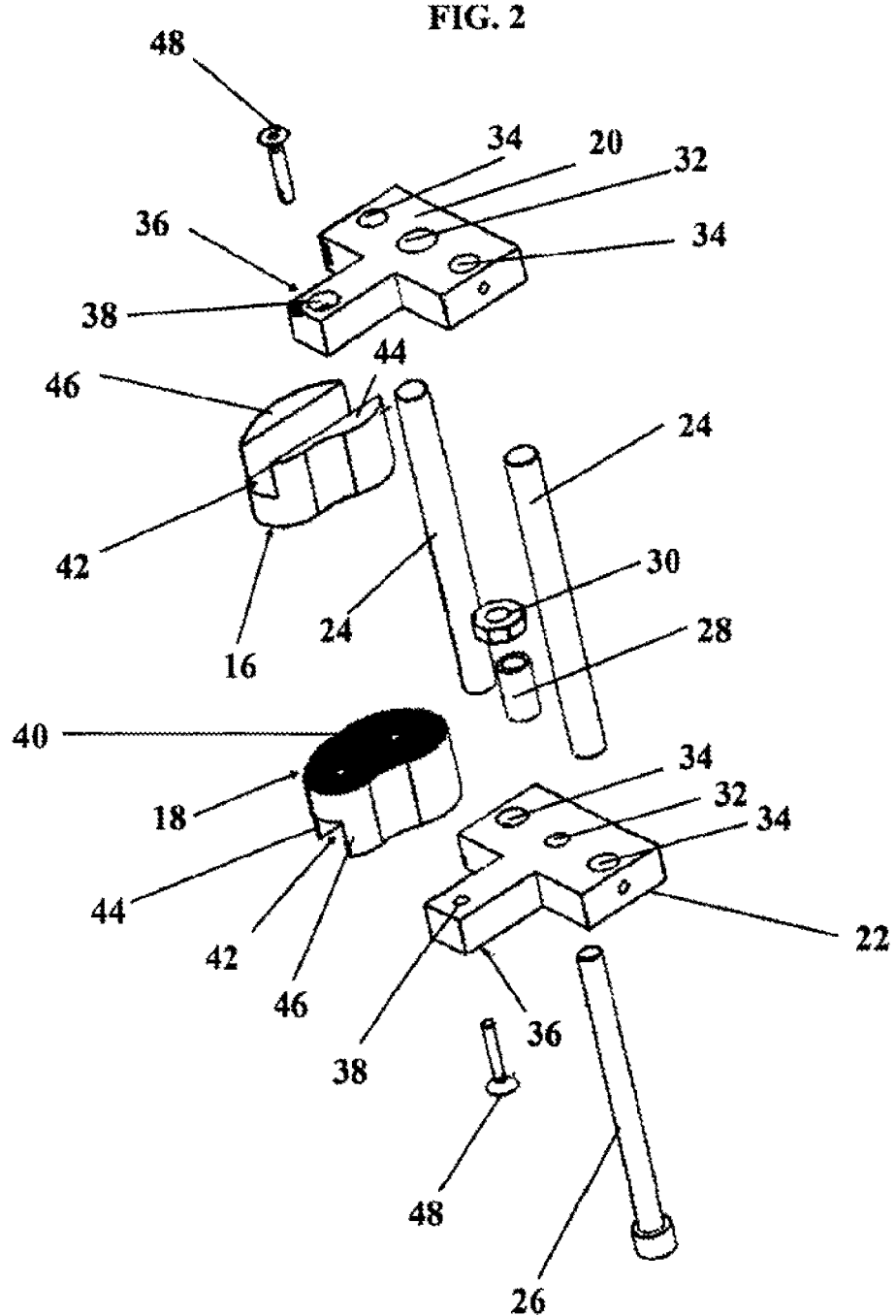
FIG. 2 is an exploded view of the bone clamps of FIG. 1, in accordance with an aspect of the present invention.
Figure 3:
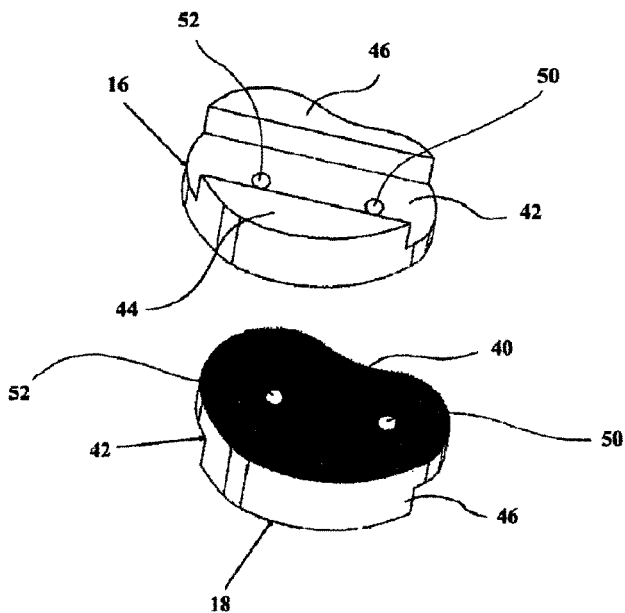
FIG. 3 is an isometric view of a mating pair of jaws for the bone clamp of FIG. 1, in accordance with an aspect of the present invention.

Referring to the drawings, wherein like reference numerals are used to indicate like or analogous components throughout the several views, and with particular reference to FIGS. 1-3, there is illustrated an exemplary embodiment bone clamping device 10 for cutting an allograft or xenograft bone into a specific shape for creating bone segments for implantation. The clamping device 10 having a first clamp 12, a second clamp 14, a first jaw 16, and a second jaw 18. As best illustrated in FIGS. 1 and 2, the first clamp 12 and the second clamp 14 both having a top base 20, a bottom base 22, two guide rails 24, a clamping screw 26, a spacer 28, and a retaining screw 30. The top base 20 having a first opening 32 for receiving the clamping screw 26, a pair of second openings 34 for receiving the two guide rails 24, and an attachment member 36 having a third opening 38 for attaching the first jaw 16. The bottom base 22 having a first opening 32 for receiving the clamping screw 26, a pair of second openings 34 for receiving the two guide rails 24, and an attachment member 36 having a third opening 38 for attaching the second jaw 18.

Figure 4:
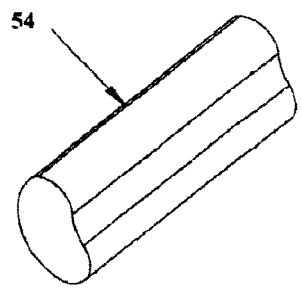
FIG. 4 is an isometric view of a piece of bone cut using the bone clamps of FIG. 1, in accordance with an aspect of the present invention.

The first jaw 16 and the second jaw 18 have an outer anatomical profile designed to guide a cutting device, such as a saw blade, for cutting a allograft or xenograft bone into a shaft of bone 54 (See FIG. 4). As depicted in FIGS. 1-3, the first jaw 16 and second jaw 18 are shaped for cutting allograft or xenograft bone for creating Lapidus implants for insertion at the tarsal-metatarsal joints, as well as for insertion into other joints in the upper and lower extremity having similar shapes. The clamping device 10 may also be used for cutting other bones having various sizes and shapes by replacing the first jaw 16 and second jaw 18 with differently shaped jaw members. For example, the clamping device 10 may also be used for creating implants for insertion between the cuboid and calcaneous, within the calcaneous, and at the subtalar joint, as well as in the upper extremity at the metacarpo-phalangeal joint, carpo-metacarpal joint and at other joints or bones within the human body. The first jaw 16 and second jaw 18 may have opposing serrated faces 40 for clamping the allograft or xenograft bone during cutting. As best illustrated in FIG. 3, the first jaw 16 and second jaw 18 may also have a channel 42 in the back side of the first jaw 16 and second jaw 18 and having a first side member 44 and a second side member 46 for securing the first jaw 16 and second jaw 18 to the attachment members 36 of the top base 20 and bottom base 22. The first jaw 16 and second jaw 18 having a first opening 50 and a second opening 52 which may be used to secure the first jaw 16 and second jaw 18 to the attachment members 36.

As best illustrated in FIGS. 1 and 2, the first jaw 16 is secured to the attachment member 36 of the top base 20 by a fastener 48, such as a screw, and the second jaw 18 is secured to the attachment member 36 of the bottom base 22 by a fastener 48. The fasteners 48 pass through the third opening 38 in the attachment members 36 and into the first openings 50 in the first jaw 16 and second jaw 18 to secure the first jaw 16 and second jaw 18 to the attachment members 36. A piece of allograft or xenograft bone, (Not Shown), may then be positioned on the second jaw 18 of the bottom base 22 for cutting. The piece of allograft or xenograft bone may preferably be a square, cylinder, or any shape having at least two parallel surfaces for being clamped between the first jaw 16 and the second jaw 18. The top base 20 may then be lowered along the two guide rails 24 until the first jaw 16 contacts the top of the allograft or xenograft bone. Once the first jaw 16 and second jaw 18 are in contact with the allograft or xenograft bone and the allograft or xenograft bone is positioned for cutting, the clamping screw 26 may be tightened securing the allograft or xenograft bone in place in the first clamp 12. The spacer 28 and retaining screw 30 may also be used to secure the first clamp 12 before cutting the allograft or xenograft bone. Once the allograft or xenograft bone is captured between the first jaw 16 and second jaw 18 of the first clamp 12, a cutting device, such as a saw blade, preferably long enough to contact the first jaw 16 and the second jaw 18 simultaneously, may trace around the outer profile of the first jaw 16 and second jaw 18. After the saw blade traces around the outer profile with the first clamp 12 attached, the second clamp 14 may be secured to the second jaw 18 at second opening 52 using a fastener 48 as described above. Then the top base 20 may be slid into place in the first jaw 16, secured using clamping screw 26 of the second clamp 14. A fastener 48 may be used to attach the attachment member 36 of the top base 20 to the first jaw 16 at second opening 52. The first clamp 12 may then be loosened and removed from the allograft or xenograft bone. Once the first clamp 12 is removed the user may then use a saw blade to trace around the outer profile of the uncut portion of the bone along the first jaw 16 and the second jaw 18. Once the second cut is complete, a shaft of bone 54 with a profile matching that of the first jaw 16 and second jaw 18 is created, as best seen in FIG. 4. As illustrated in FIG. 4, the shaft of bone 54 may have a shape which corresponds to the shape of the tarsal-metatarsal joints, which may appear to have an oblong shape, more particularly a kidney bean shape or the shape of any other target location in which the implant may be placed.

Figure 5A:
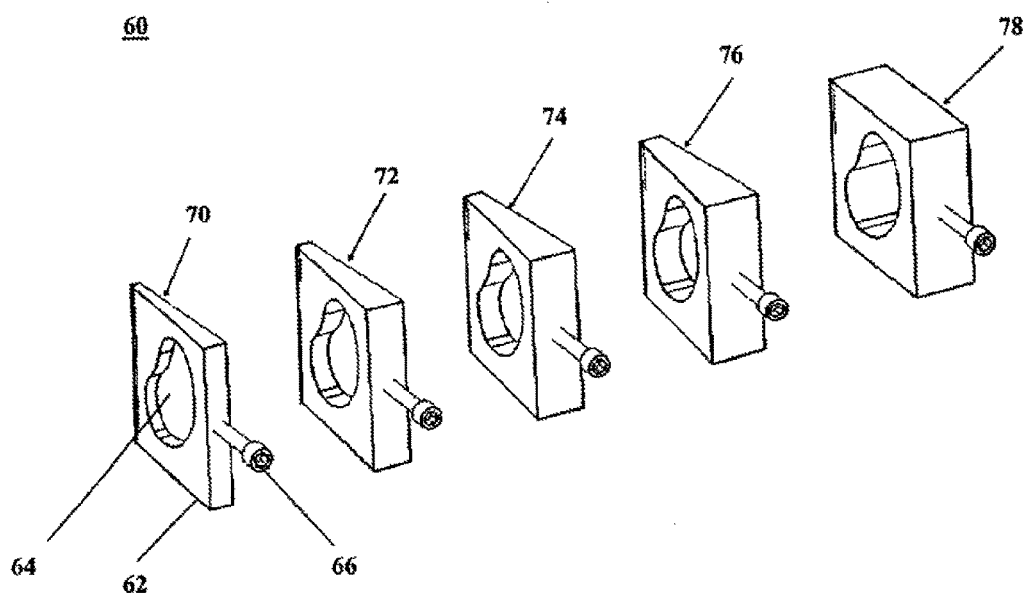
FIG. 5A is an isometric view of a set of wedge shaped saw jigs, in accordance with an aspect of the present invention.
Figure 5B:
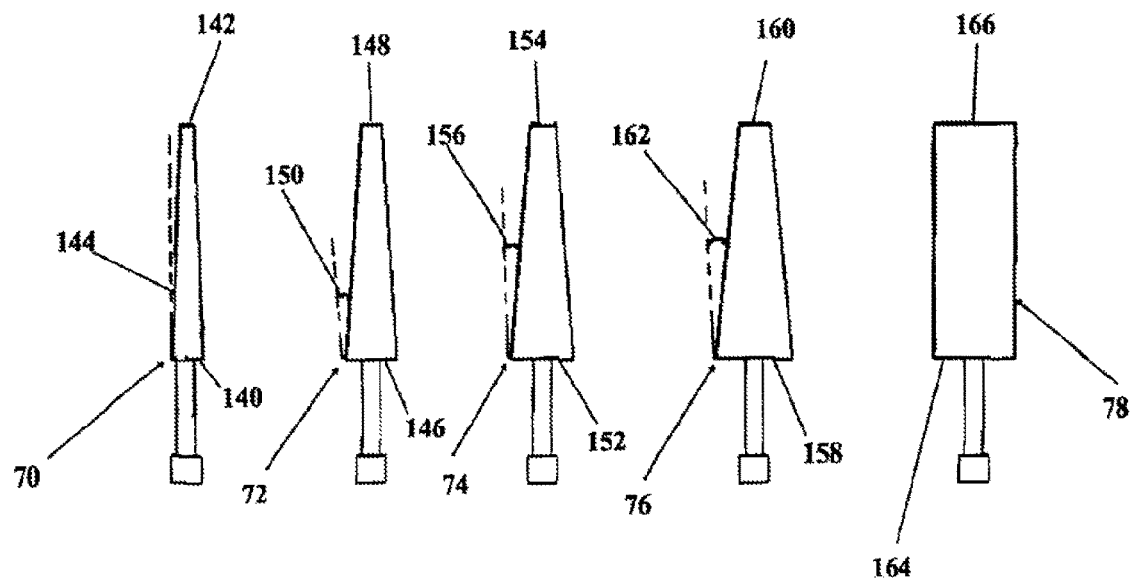
FIG. 5B is a top view of the set of wedge shaped saw jigs of FIG. 5A, in accordance with an aspect of the present invention.
Figure 6:
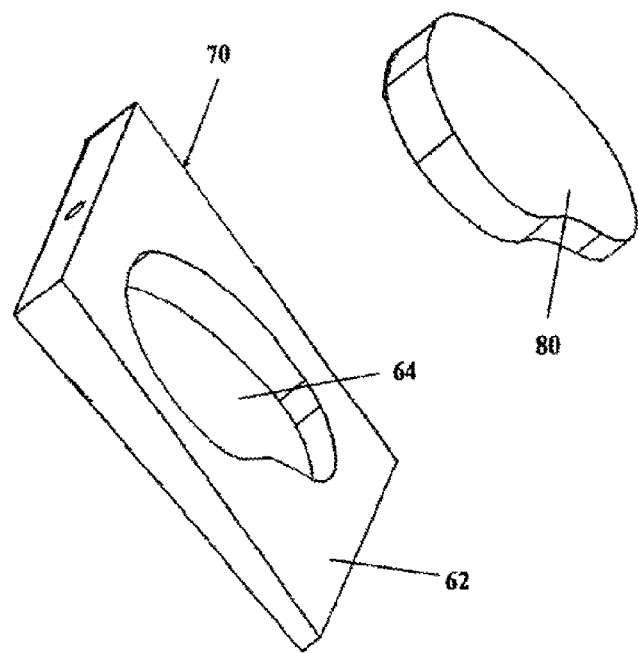
FIG. 6 is an isometric view of one of the wedge shaped saw jigs of FIG. 5 and a bone wedge cut using the saw jig, in accordance with an aspect of the present invention.

As best seen in FIG. 5A, is a set of saw jigs 60 for creating bone wedges of various sizes. The saw jigs 60 having a plate 62 with an oblong shaped opening 64, more preferably Lapidus shaped as depicted, and a locking screw 66. The saw jigs 60 may be created in various sizes for example preferably ranging from about 3 mm and 3° to about 20 mm to 20° to correspond to various degrees of correction, as well as for example 5 mm and 0° to about 20 mm and 0°. The saw jigs 60 may more preferably range from about 5 mm and 5° to about 12 mm and 12° to correspond to the various degrees of correction, as well as for example 14 mm and 0° to other thicknesses and angulations which may be cut to a final size during a case intra-operatively. Other sizes are also contemplated which correspond to the patient's anatomy as well as other sizes with no angles which may be sized intra-operatively. The saw jigs 60 include a first saw jig 70, a second saw jig 72, a third saw jig 74, a fourth saw jig 76, and a fifth saw jig 78, as depicted in the embodiment in FIGS. 5A-5B. The first saw jig 70 having a first end 140, a second end 142, and an angle 144 where for example the first end 140 is about 5 mm and the angle 144 is about 5°. The second saw jig 72 has a first end 146, a second end 148, and an angle 150 where for example the first end 146 is about 8 mm and the angle is about 8°. The third saw jig 74 has a first end 152, a second end 154, and an angle 156 where the first end 152 is about 10 mm and the angle is about 10°. The fourth saw jig 76 has a first end 158, a second end 160, and an angle 162 where for example the first end 158 is about 12 mm and the angle 162 is about 12°. The fifth saw jig 78 has a first end 164 and a second end 166 with a uniform thickness where for example the first end 164 and second end 166 are about 14 mm. The saw jigs 60 wherein where the first ends 140, 146, 152, 158, and 164 are opposite the second ends 142, 148, 154, 160, and 166. The shaft of bone 54 which was cut using the clamping device 10, as seen in FIG. 4, would be inserted into the opening 64 of one of the set of saw jigs 60 having the desired dimensions for implantation and the shaft of bone 54 would be secured using the locking screw 66. Then a band saw blade or other cutting device, not shown, could be operated along both sides of the saw jig selected from the set of saw jigs 60 creating a bone wedge 80. The bone wedge 80 may be cut using the saw jigs 60 to mimic the anatomical considerations of the bones the bone wedge 80 is being inserted between with the desired angular corrections for a given procedure.

Referring now to FIGS. 6-9, an example of the bone wedge 80 which may be cut from the first saw jig 70 is shown. The bone wedge 80 has a profile identical to the Lapidus shaped opening 64 of the first saw jig 70. Illustrated in FIGS. 7A-7E, are an isometric view, a distal side view, a medial side view, a plantar side view, and a lateral side view of the bone wedge 80, respectively. The bone wedge 80 is cut to a desired restoration length necessary for the patient receiving the implant and has an outer anatomical profile that mimics the anatomical considerations of the bones it is being inserted between. For example, as depicted in FIGS. 8 and 9, the outer anatomical profile of the bone wedge 80 on the proximal and distal sides is cut to mimic the shapes of the medial cuneiform 82 and metatarsal 84 bones, which is an oblong shape, or more preferably is a kidney shape. In addition, the bone wedge 80 is cut with a desired angle thereby creating a desired angular offset between the medial cuneiform 82 and the metatarsal 84. The bone wedge 80 may be cut in the saw jigs 70, 72, 74, or 76 to create a wedge geometry having reproducible angular corrections which are desired for a given procedure. For example, in the Lapidus implant the desired angulation may be used to correct valgus and plantar angulation of the bones by tapering the bone wedge 80 from the medial side to the lateral side and from the dorsal side to the plantar side. The bone wedge 80 may have heights ranging from about 25 mm to 40 mm, width ranging from about 10 mm to 30 mm, and thickness ranging from about 0 mm to 20 mm at the dorsal side and the medial side and tapering from the dorsal side to plantar side and medial side to lateral side at an angle ranging from about 0° to 20°. More preferably, the bone wedges 80 have heights of about 32 mm, a width of about 21 mm at the dorsal medial corner, and functional thickness of 5 mm and 5°, 8 mm and 8°, 10 mm and 10°, 12 mm and 12°, and 14 mm and 0°. It is also contemplated that the taper of the thickness of the bone wedge 80 may be from the dorsal-medial corner to the plantar-lateral corner.

Figure 7A:
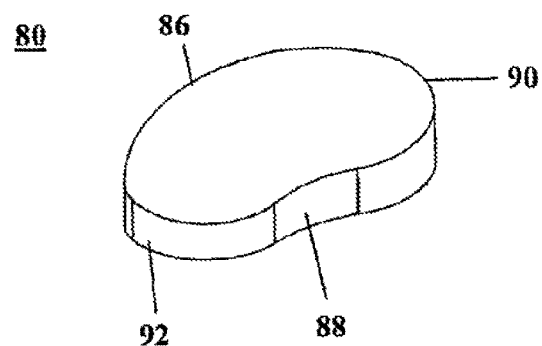
FIG. 7A is an isometric view of a wedge shaped bone segment with an anatomical profile, in accordance with an aspect of the present invention.
Figure 7B:
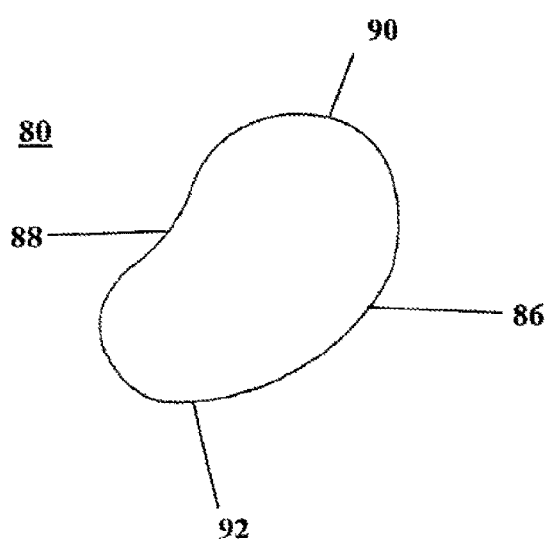
FIG. 7B is a distal side view of the wedge shaped bone segment of FIG. 7A, in accordance with an aspect of the present invention.
Figure 7C:
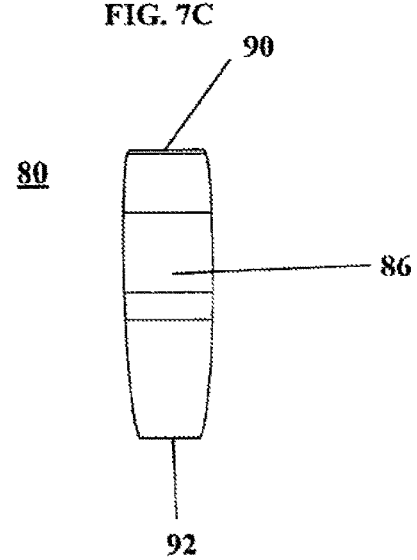
FIG. 7C is a medial side view of the wedge shaped bone segment of FIGS. 7A-7B, in accordance with an aspect of the present invention.
Figure 7D:
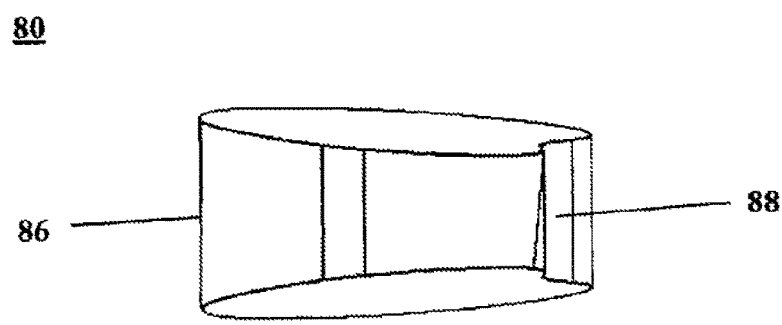
FIG. 7D is a plantar side view of the wedge shaped bone segment of FIGS. 7A-7C, in accordance with an aspect of the present invention.
Figure 7E:
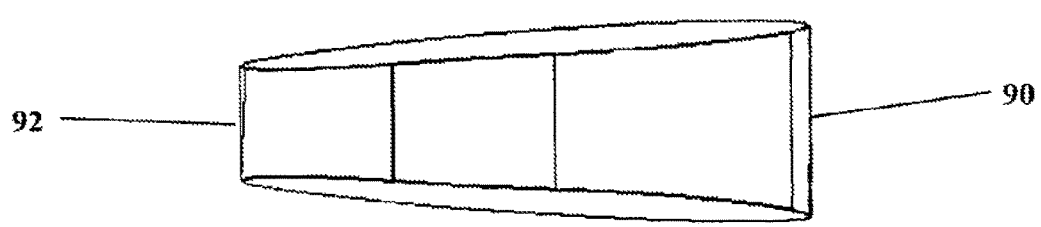
FIG. 7E is a lateral side view of the wedge shaped bone segment of FIGS. 7A-7D, in accordance with an aspect of the present invention.

As seen in FIGS. 7D-7E, the bone wedge 80 is tapered in the medial-lateral plane from the medial side 86 of the bone wedge 80 to the lateral side 88 and in the dorsal-planatar plane from the dorsal side 90 of the bone wedge 80 to the plantar side 92. More particularly, the bone wedge 80 may be tapered from the dorsal-medial corner to plantar-lateral corner of the Z-axis. Thus, a bi-planar surface is created on the bone wedge 80 wherein the proximal surface converges towards the distal surface. The bone wedge 80 may be cut from bone for example cancellous bone and/or a combination of cortical or cancellous bone, or may be made of metal, for example a titanium material, or may be made of a polymer or composite, for example a polyetheretherketone ("PEEK") material, or other material appropriate for implantation. In the event allograft or xenograft bone is used it may be minimally processed allograft or xenograft bone having stout cancellous or cancellous and cortical bone and is used for retaining maximum osteoinductivity. The minimally processed allograft or xenograft bone is not gamma irradiated to preserve mechanical integrity and is not exposed to peroxides to preserve osteoinductivity.

A surgical method for implanting the bone wedge 80 into a joint, shown in FIG. 23, will now be described. The method utilizes some of the devices, instruments, features, aspects, components and the like described above, and therefore reference will be made to the above described embodiments, such as the illustrated embodiments presented in the figures and discussed above. However, such references are made for exemplary purposes only and are not intended to limit the surgical method beyond the specifically recited steps. Further, the surgical method may be discussed under the umbrella of particular bones, but such an application is not intended to be limiting and the method described herein may be used or conducted with bone or other tissue not specifically discussed herein without departing from the spirit and scope of the surgical method.

Assuming the patient has a hallux valgus deformity which needs to be corrected, an implant device, such as bone wedge 80, and fixation members, such as pins, screws, plates, or external fixation may be used to correct the deformity. For example, the hallux may be pointing outward away from the midline of the body and need to be realigned, wherein the first metatarsal and phalanx may be angled away from the midline of the body and towards the other toes. As the first metatarsal and medial cuneiform are being used for exemplary purposes only, the generic term "first bone" may be used hereinafter to refer to the first metatarsal bone, or any other bone that includes similar features, positioning, orientation, function or the like. Similarly, the generic term "second bone" may be used hereinafter to refer to the medial cuneiform, or any other bone that includes similar features, positioning, orientation, function or the like. Likewise, the generic term "first joint" may be used hereinafter to refer to the joint between the first metatarsal and the medial cuneiform, or any other joint that includes similar features, positioning, orientation, function or the like.

Figure 23:
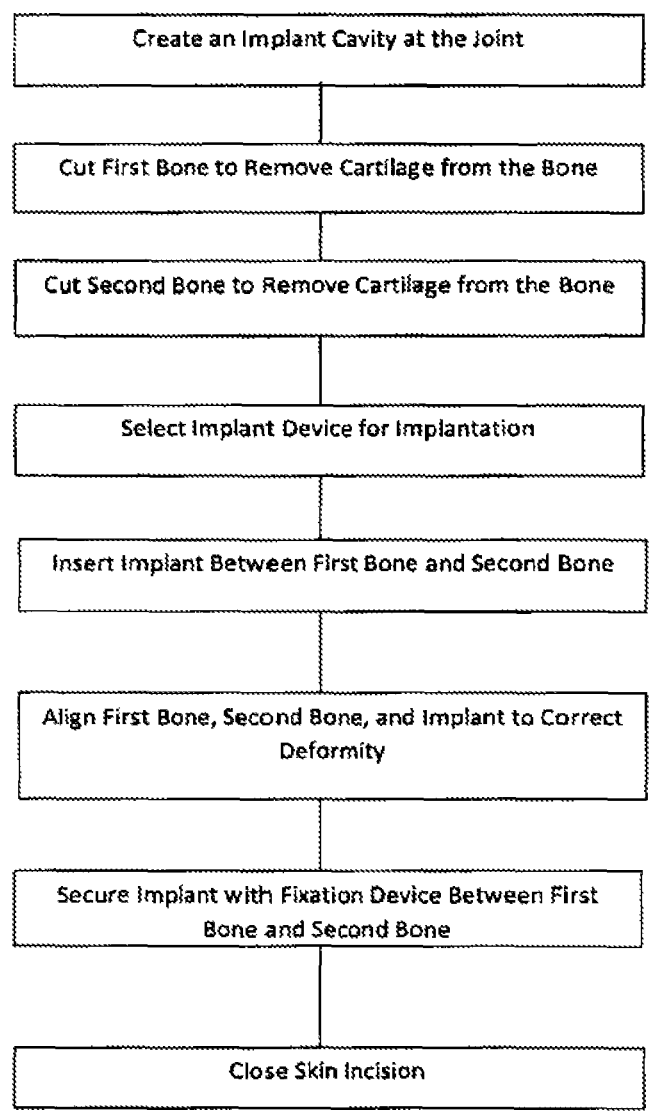
FIG. 23 depicts one embodiment of a surgical method for implanting an implant device into a patient's body, in accordance with an aspect of the present invention.

As illustrated in FIG. 23, in order to correct the deformity in the first and second bones, an implant cavity will first be formed at the first joint, whereby the first joint is exposed so the first and second bones may be prepared for the arthrodesis. The first bone will then be cut to remove the cartilage from the base of the first bone. Next, the second bone will be cut to remove the cartilage from the distal aspect of the second bone. The cut to the second bone should be performed at a 45° angle dorsal medial to plantar lateral to provide two planes of correction to the first and second bones. Once the first and second bone have been prepared the surgeon may either select a bone wedge 80 from a kit containing a set of various sizes of bone wedges and implant the bone wedge 80 having the desired width and angle. Alternatively, if a different size bone wedge is needed the surgeon may select the bone wedge 80 from the kit having a uniform size and cut a custom bone wedge, (Not Shown), for the desired site intra-operatively. Once a bone wedge 80 has been selected it may then be inserted between the first and second bones and aligned to correct the deformity of the bones. After the correct alignment has been achieved the bone wedge 80 must be fixed within the first joint with one or more fixation devices. The fixation devices may include screws, wires, plates, or external fixation. Once the bone wedge 80 is secured within the first joint the skin incision may be closed up by the surgeon.

One advantage of the embodiments discussed herein of the present invention is that the bone wedge 80 enables correction in both the dorsal-plantar plane and medial-lateral plane. Alternatively and more specifically, the bone wedge 80 may provide angulation from the dorsal-medial plane to the plantar-lateral plane. In addition, the Lapidus procedure allows for plantar angulation of the first ray to restore weight distribution back to the sesamoids. The custom allograft bone wedge 80 is designed to mimic the oblong shape of the joint, more particularly the kidney bean shape of the joint, and restore the angulation of the wedge to 45 degrees from the z-axis to provide both plantar and valgus angulation of the proximal phalanx. Another advantage of the embodiments of the present invention discussed herein is that the bone wedge 80 may be composed of the most robust cancellous or cancellous and cortical structure and will preserve the structure and osteoinductivity of the adjacent bones. A further advantage of the present invention discussed herein is that the bone wedge 80 may be used to correct a number of deformities in various joints and bones of the upper and lower extremities.

Figure 10A:
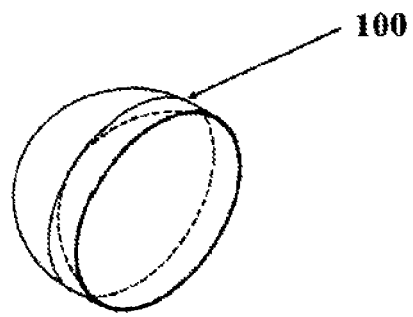
FIG. 10A is an isometric view of a restoration bone segment, in accordance with an aspect of the present invention.
Figure 10B:
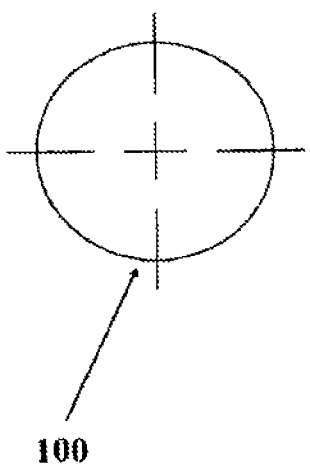
FIG. 10B is a front view of a restoration bone segment, in accordance with an aspect of the present invention.
Figure 10C:
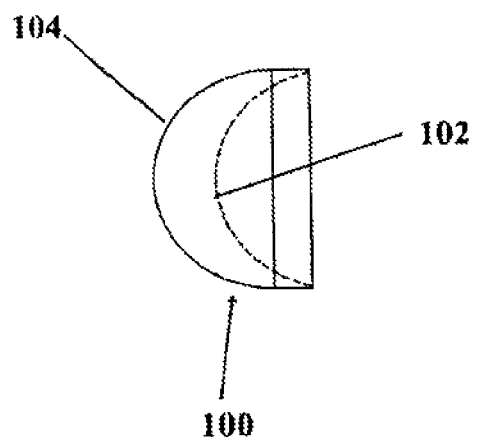
FIG. 10C is a side view of a restoration bone segment, in accordance with an aspect of the present invention.
Figure 11:
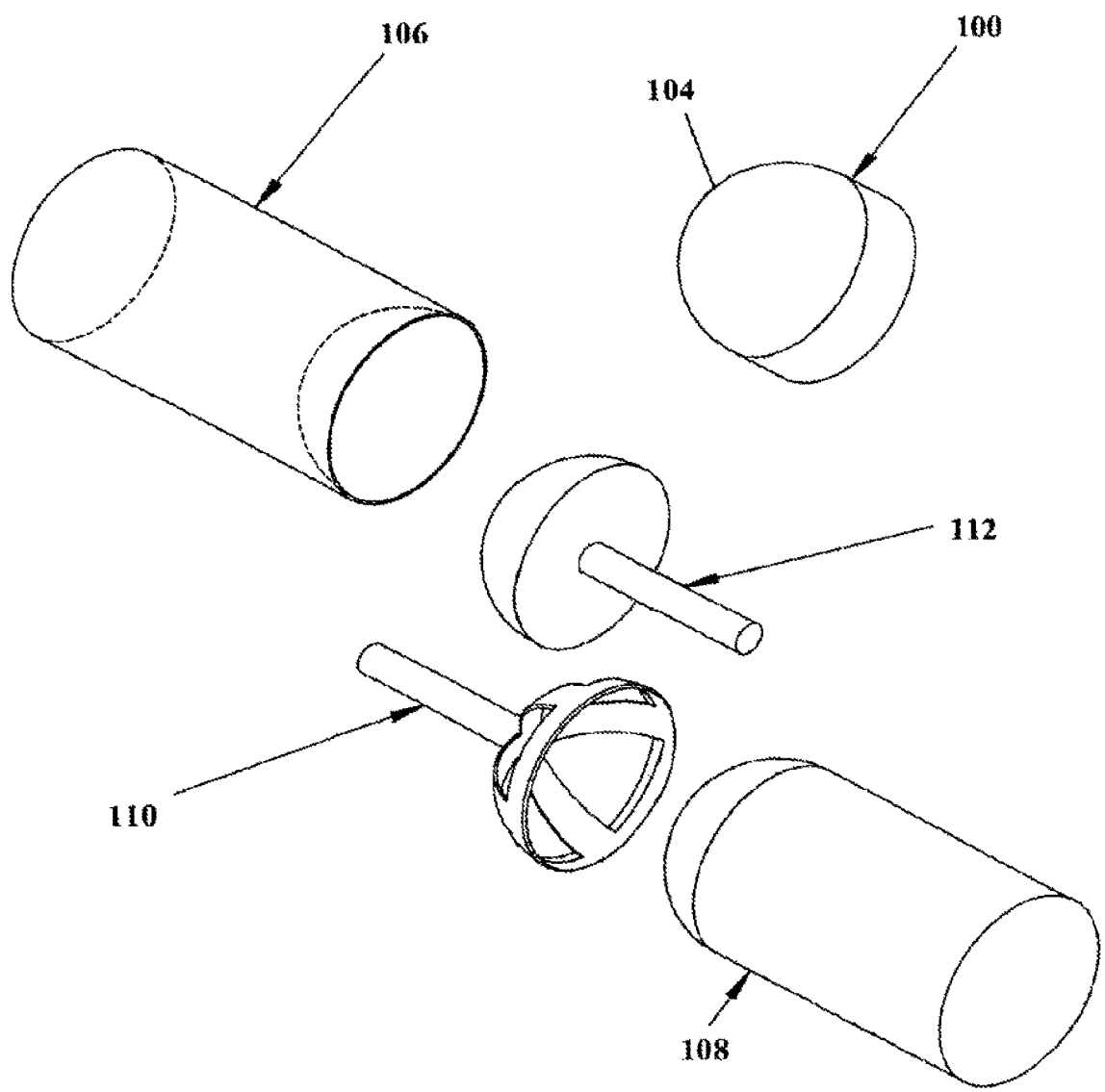
FIG. 11 is an isometric view of a cup and cone reamers, two prepared bone surfaces, and a restoration bone segment of FIGS. 10A-10C, in accordance with an aspect of the present invention.

Referring now to FIGS. 10A-21, illustrated in these figures are various implants and surgical instruments including cup and cone reamers and a restoration bone segment. As best seen in FIGS. 10A-10C, is a restoration bone segment 100 which may be used for insertion between two bone segments to adjust their overall length. The restoration bone segment 100 may be cut from bone, for example cancellous bone or combination cancellous/cortical bone, may be made of metal, for example a titanium material, or may be made of a polymer or composite, for example a polyetheretherketone ("PEEK") material. The allograft or xenograft bone is a minimally processed allograft or xenograft bone having stout cancellous bone or cancellous and cortical bone and is used to maintain maximum osteoinductivity. The restoration bone segment 100 has a concave end 102 for mating with a convex bone 108 and a convex end 104 for mating with a concave bone 106, as depicted in FIG. 11. The restoration bone segment 100 may be made using a cone reamer 110 and a cup reamer 112 which creates a ball and socket like configuration. To create the restoration bone segment 100, a cylindrical piece of bone having the desired circumference may have a convex end 104 created using the cone reamer 110, then the bone may be cut to the desired length and the cup reamer 112 may be used to create the concave end 102. Alternatively, the piece of bone may have the concave end 102 created using the cup reamer 112, then the bone may be cut to the desired length and the cone reamer 110 used to create the convex end 104. In addition, the cone reamer 110 and cup reamer 112 may be used to prepare the bones for insertion of the restoration bone segment 100, described in greater detail hereinafter.

Figure 12:
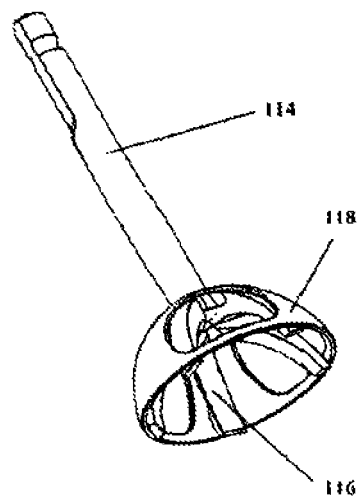
FIG. 12 is an isometric view of another embodiment of a cup reamer and cover, in accordance with an aspect of the present invention.
Figure 13:
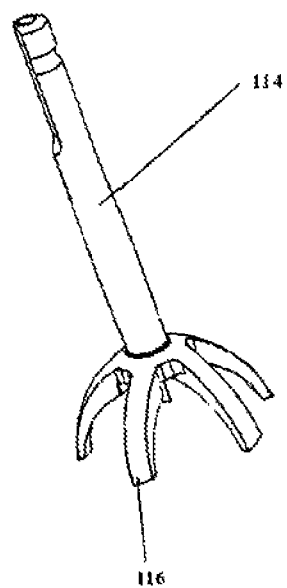
FIG. 13 is an isometric top view of the cup reamer of FIG. 12, in accordance with an aspect of the present invention.
Figure 14:
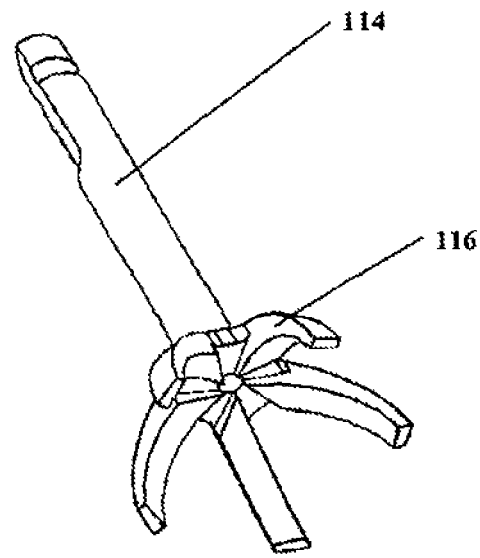
FIG. 14 is an isometric bottom view of the cup reamer of FIG. 12, in accordance with an aspect of the present invention.
Figure 15:
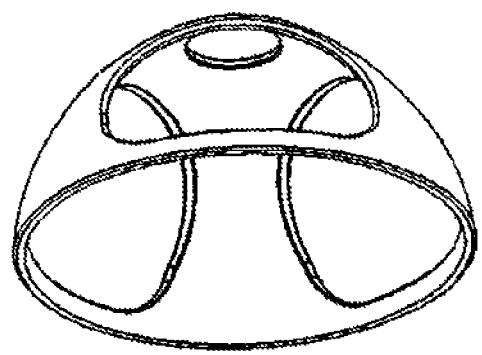
FIG. 15 is an isometric view of the cup reamer cover of FIG. 12, in accordance with an aspect of the present invention.

Another embodiment of the cone reamer 110 is depicted in FIG. 12. The cone reamer 110 has a shank 114 for insertion into a drill, a cutting edge 116 for cutting a convex shape into bone, and a backstop 118 to protect the opposite side from damage during reaming. As illustrated in FIGS. 13 and 14, it is also contemplated that the cone reamer 110 may be used without the backstop 118, seen in FIG. 15. Various size cutting edges 116 may be provided based on the desired diameter of the convex end 104 of the bone segment 100 and corresponding convex bone 108. The inner diameter of the cutting edge 116 corresponds to the outer diameter of the bone cut with the cone reamer 110.

Figure 16A:
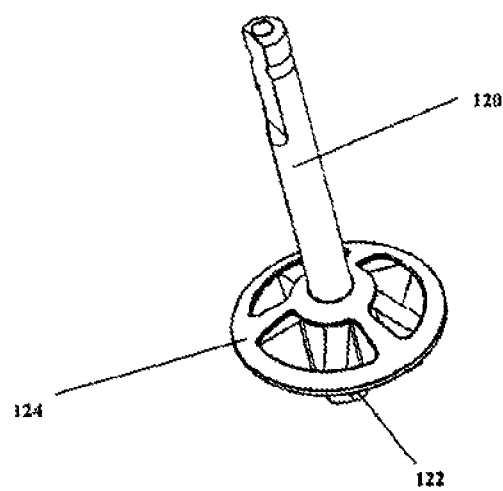
FIG. 16A is an isometric top view of another embodiment of a cone reamer and cover, in accordance with an aspect of the present invention.
Figure 16B:
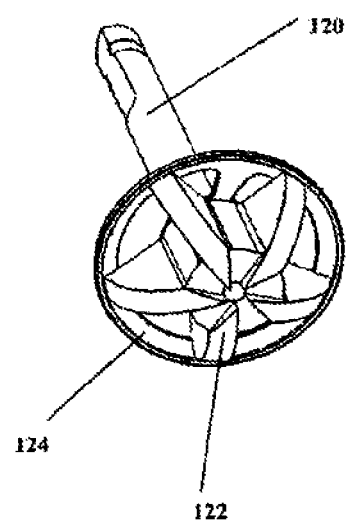
FIG. 16B is an isometric bottom view of the cone reamer and cover of FIG. 16A, in accordance with an aspect of the present invention.
Figure 17:
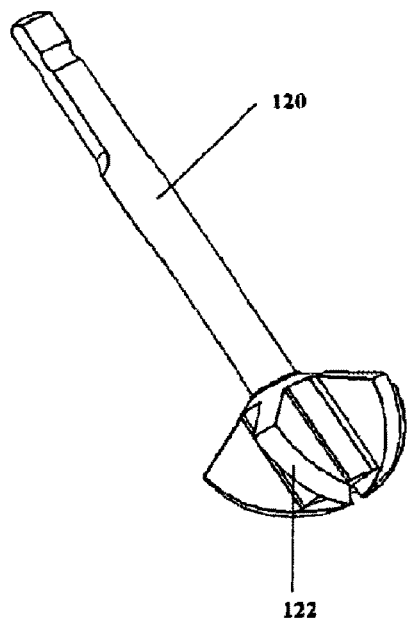
FIG. 17 is an isometric side view of the cone reamer of FIGS. 16A and 16B, in accordance with an aspect of the present invention.
Figure 18:
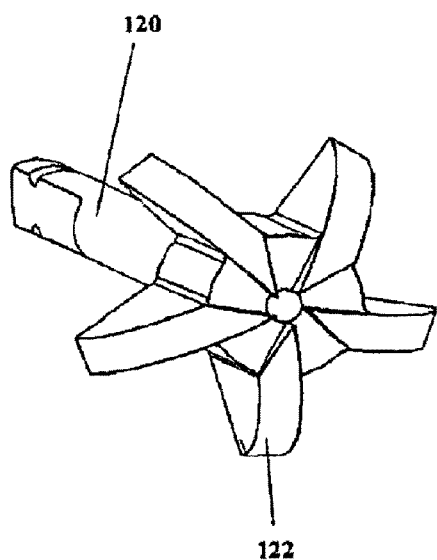
FIG. 18 is an isometric bottom view of the cone reamer of FIG. 17, in accordance with an aspect of the present invention.
Figure 19:
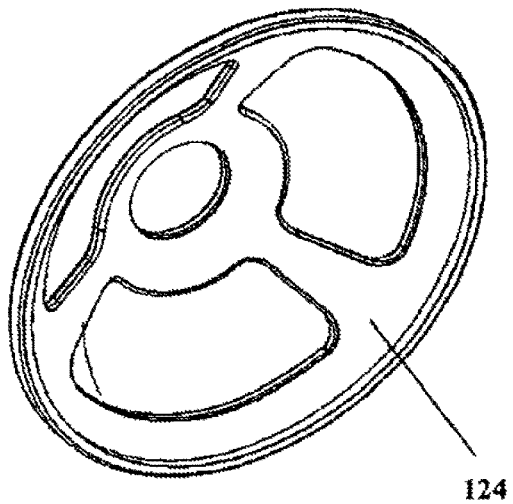
FIG. 19 is an isometric bottom view of the cone reamer cover of FIGS. 16A and 16B, in accordance with an aspect of the present invention.

Illustrated in FIGS. 16A-16B is another embodiment of the cup reamer 112. The cup reamer 112 has a shank 120 for insertion into a drill, a cutting edge 122 for cutting a concave shape into a bone, and a backstop 124 to protect the opposite side from damage during reaming. It is also contemplated and depicted in FIGS. 17-18 that the cup reamer 112 may be used without the backstop 124, seen in FIG. 19. Various size cutting edges 122 may be provided based on the desired diameter of the concave end 102 of the bone segment 100 and corresponding concave bone 106. The outer diameter of the cutting edge 122 corresponds to the inner diameter of the bone cut with the cup reamer 112.

Figure 20:
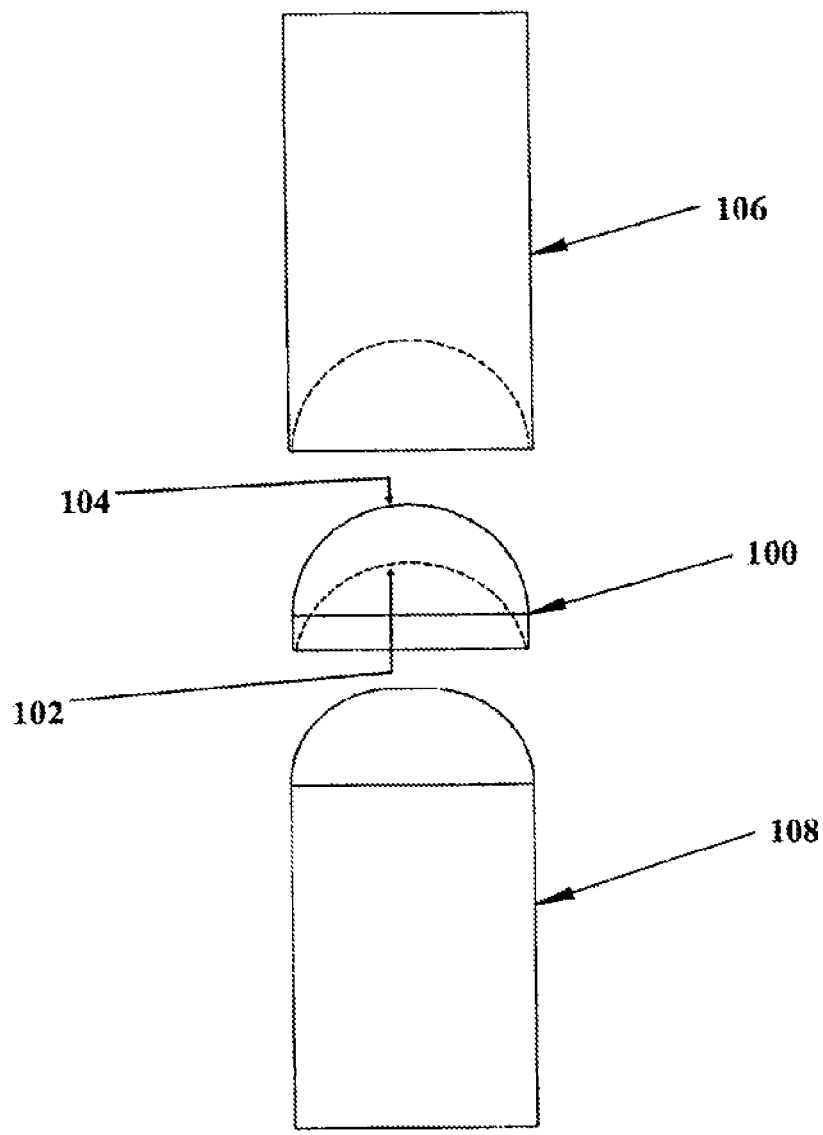
FIG. 20 is a side view of two prepared bone surfaces and a concave and convex shaped bone segment, in accordance with an aspect of the present invention.
Figure 21:
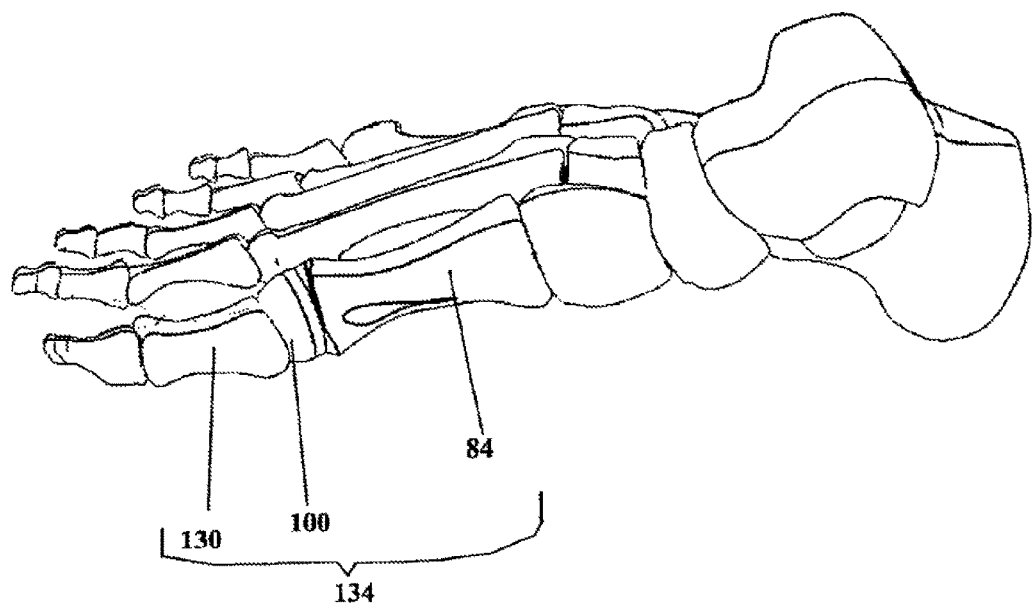
FIG. 21 is a medial view of a right foot having the bone segment of FIGS. 10A-10C implanted in the foot, in accordance with an aspect of the present invention.

Referring now to FIG. 20, the restoration bone segment 100 is shown aligned with the corresponding bones for implantation. The first bone being a concave bone 106 for mating with the convex end 104 of the bone segment 100 and the second bone being a convex bone 108 for mating with the concave end 102 of the bone segment 100. The cone reamer 110 and cup reamer 112 may have cutting edges 116 and 122, respectively, ranging for example from about 10 mm to 24 mm, with the most preferred dimensions for correction at the metatarsal-phalangeal joints being for example about 19 mm to 21 mm. As depicted in FIG. 21, the bone segment 100 may be inserted between the proximal phalanx 130 and the first metatarsal 84. In the depicted embodiment, the proximal end of the phalanx 130 is the concave bone 106 which mates with the convex end 104 of the bone segment 100, while the distal end of the first metatarsal 84 is the convex bone 108 which mates with the concave end 102 of the bone segment 100 to create a ball and socket configured metatarsal-phalangeal joint 134. By using an implant with a concave end 102 and a convex end 104 the amount of bone resection of the metatarsal-phalangeal joint 134 is minimized. In addition, the use of the bone segment 100 enables lengthening of the first metatarsal 84 before the metatarsal-phalangeal joint 134 is fused to help maintain a normal gait for the patient. The diameter of the bone segment 100 for use in the metatarsal-phalangeal joint 134 may range from for example about 10 mm to 24 mm, with the more preferable dimensions being for example about 19 mm to 21 mm. The thickness of the bone segment 100 for use in the metatarsal-phalangeal joint 134 may range from about 5 mm to about 20 mm for a bone segment 100. It is also contemplated that the bone segment 100 may be used in other joints and bones of the lower extremity, as well as in the joints and bones of the upper extremity.

Figure 24:
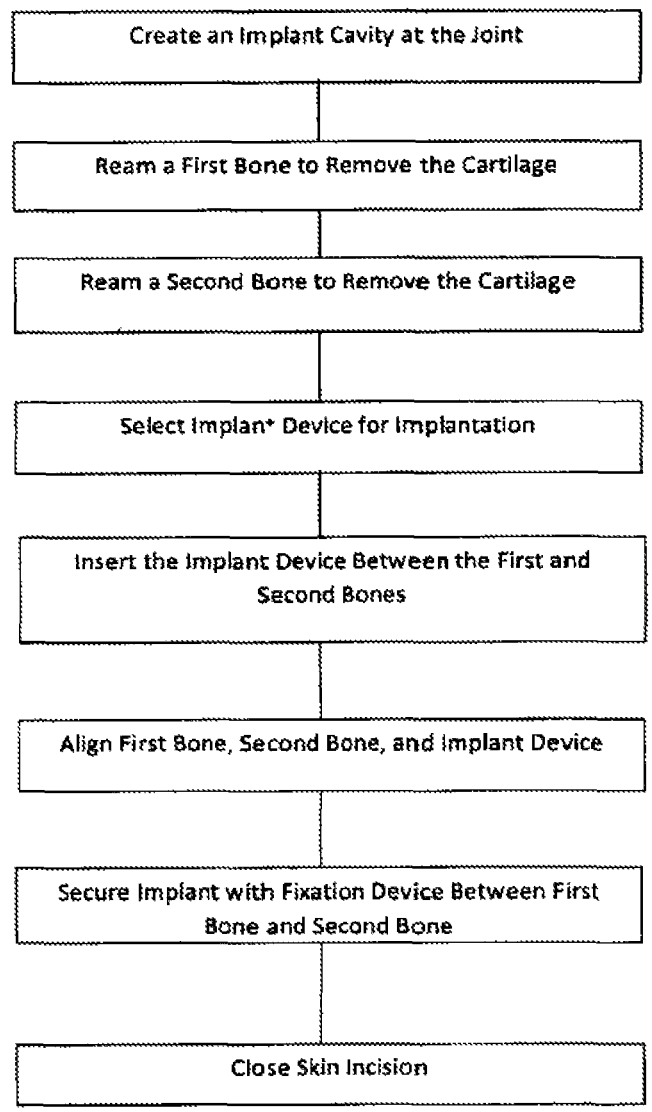
FIG. 24 depicts another embodiment of a surgical method for implanting an implant device into a patient's body, in accordance with an aspect of the present invention.

A surgical method for implanting the bone segment 100 into a joint, as seen in FIG. 24, will now be described. The method utilizes some of the devices, instruments, features, aspects, components, and the like described above, and therefore reference will be made to the above described embodiments, such as the illustrated embodiments presented in the figures and discussed above. However, such references are made for exemplary purposes only and are not intended to limit the surgical method beyond the specifically recited steps. Further, the surgical method may be discussed under the umbrella of particular bones, but such an application is not intended to be limiting and the method described herein may be used or conducted with bone or other tissue not specifically discussed herein without departing from the spirit and scope of the surgical method.

Assuming the patient has a shortened bone which needs to be corrected, an implant device, such as bone segment 100, and a fixation member may be used to correct the deformity. The fixation member may include one or more plates, screws, wires, or external fixation. For example, the first metatarsal and phalanx may have been shortened due to several reasons, such as a hallux valgus deformity, a revision surgery due to a failed prior surgery, a non-union, or a generally short anatomy. All of these resulting in a shortened first metatarsal, which may be affecting the person's gait. As the phalanx and first metatarsal are being used for exemplary purposes only, the generic term "first bone" may be used hereinafter to refer to the phalanx bone, or any other bone that includes similar features, positioning, orientation, function or the like. Similarly, the generic term "second bone" may be used hereinafter to refer to the first metatarsal bone, or any other bone that includes similar features, positioning, orientation, function or the like. Likewise, the generic term "first joint" may be used hereinafter to refer to the joint between the phalanx and the first metatarsal, or any other joint that includes similar features, positioning, orientation, function or the like.

As best illustrated in FIG. 24, in order to correct the deformity in the first and second bones, an implant cavity will first be formed at the first joint, whereby the first joint is exposed and the first and second bones are prepared. The first bone may be prepared by reaming the first bone to remove the cartilage from the proximal surface of the first bone thereby giving the proximal end of the first bone a concave surface. Next, the second bone may be prepared by reaming to remove the cartilage from the distal surface of the second bone, thereby giving the proximal end of the second bone a convex surface. Once the first and second bones have been prepared, the surgeon may select a bone segment 100, having a concave end 102 and a convex end 104, from a kit containing a set of each of various sizes of bone segments 100 which have various circumferences and thicknesses. Alternatively, the surgeon may select a cylinder of bone from the kit having a desired circumference and use the cup reamer 112 and cone reamer 110 to cut a bone segment 100 for the desired site intra-operatively. The surgeon then inserts the convex end 104 of the bone segment 100 into the concave surface of the first bone and fits the concave end 102 of the bone segment 100 over the convex surface of the second bone. Alternatively, the concave end 102 of the bone segment 100 may be inserted over the convex surface of the second bone and then the convex end 104 of the bone segment 100 inserted into the concave surface of the first bone. Once the bone segment 100 has been inserted the combined length of the first and second bones will be increased and the first and second bones aligned to a desired position. After the two bones are aligned and a final position is determined, a removable fixation device, such as a guide wire, may be used to secure the bone segment 100 while additional fixation is applied. The additional fixation of the bone segment 100 may be accomplished with one or more plates, screws, wires, or external fixation devices. Once the bone segment 100 is secured within the first joint, the incision may be closed by the surgeon.

One advantage of the embodiments of the present invention discussed herein is that the bone segment 100 will allow for manipulation of the joint to provide optimal positioning prior to applying fixation. The metatarsal-phalangeal bone segment 100 having a concave end and a convex end allows the surgeon to precisely position the toe with dorsiflexion and valgus specifications without the requirement of additional bone resection. The bone segment 100 may be made from allograft or xenograft bone that is robust in cancellous structure and which has only been minimally processed to maintain maximum osteoinductivity.

Figure 22:
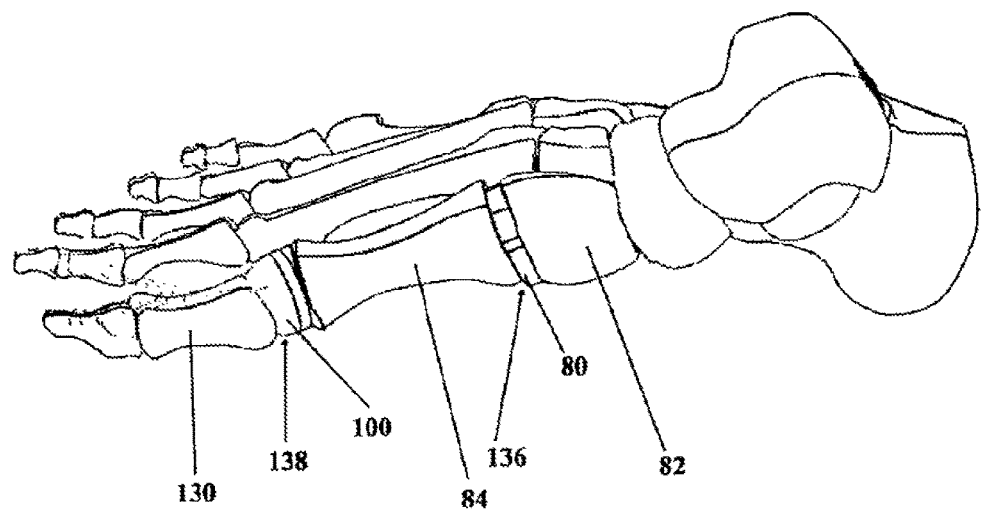
FIG. 22 is a medial view of a right foot having the bone segments of FIGS. 7A-7E and FIGS. 10A-10C implanted in the foot, in accordance with an aspect of the present invention.

An example of the placement of the bone wedge 80 of FIGS. 7A-7C and restoration bone segment 100 of FIGS. 10A-10C in the hallux are illustrated in FIG. 22. The restoration bone segment 100 may be used to adjust the length of the metatarsal-phalangeal joints or other similar joints in the upper and lower extremities. If length of the first metatarsal 84 is lost, the weight distribution on the patient's sesamoid bones may change which ultimately results in a change in how the patient walks. In order to address both the potential for functional loss of the sesamoid bones as well as a shortening of the phalanx, the present disclosure includes placement of the bone wedge 80 at the tarsal-metatarsal joint 136 and the restoration bone segment 100 at the metatarsal-phalangeal joint 138. The bone wedge 80 and the restoration bone segment 100 require additional fixation methods to secure them within the tarsal-metatarsal joint 136 and the metatarsal-phalangeal joint 138, respectively. Such fixation methods may include bone screws, wires, bone plates, external fixation, or the like. The bone wedge 80 and restoration bone segment 100 may also be used in other similar joints, for example the tarsal-metatarsal joints and metatarsal-phalangeal joints of the small toes as well as the metacarpo-phalangeal joint, carpo-metacarpal joint and other joints of the upper extremity. In addition, the bone wedge 80 may be used independently to correct deformities at the tarsal-metatarsal joint 136 and other similar joints in the upper and lower extremities. Likewise, the bone segment 100 may be used independently to correct deformities at the metatarsal-phalangeal joint 138 and other similar joints in the upper and lower extremities.

With continued reference to FIGS. 11-19 and now with reference to FIGS. 25-61, several reamer sleeves 118, 124, 200, 250, 300, and 350 which may be used with reamers, such as, reamers 110, 112, 230, and 280, are shown. The reamer sleeves 118, 124, 200, 250, 300, and 350 may be used to prevent damage to the surface of the bone opposite the side of the joint that is being reamed. If the adjacent bone is damaged during reaming, it can result in loss of bone, tissue or stock that then would need to be grafted to provide sufficient bone-on-bone contact for fusion. Thus, in joints, where it is difficult to obtain adequate exposure of the target bones and provide enough space to allow for unrestricted reaming, the reamer sleeves 118, 124, 200, 250, 300, and 350 may be used to protect the adjacent tissue of the joint.

Figure 27:
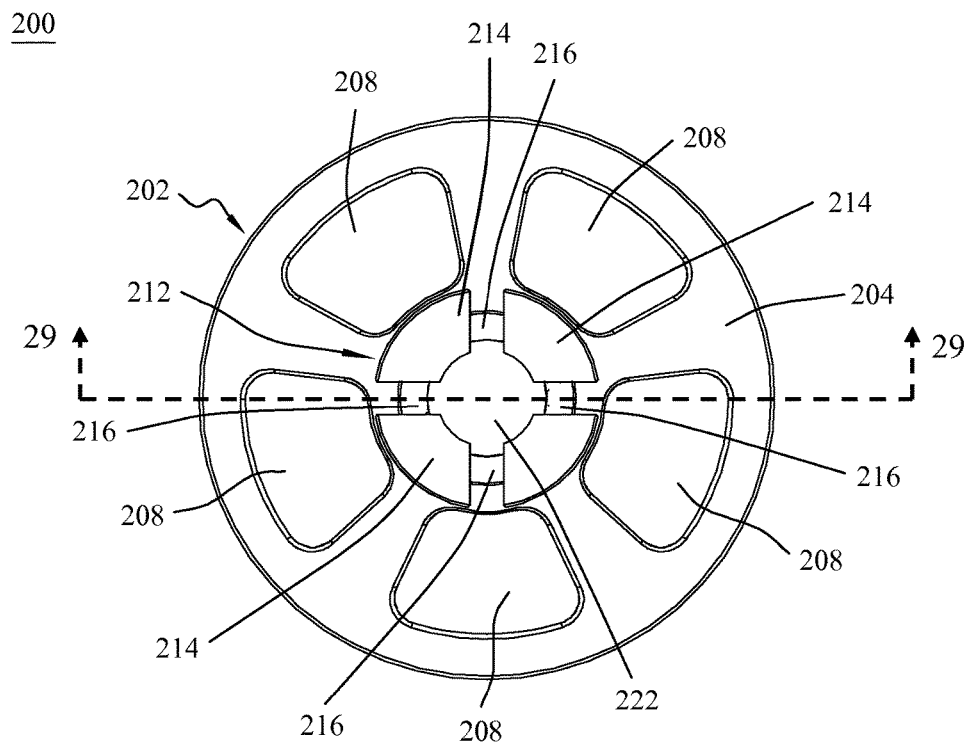
FIG. 27 is a top view of the reamer sleeve of FIG. 25, in accordance with an aspect of the present invention.
Figure 28:
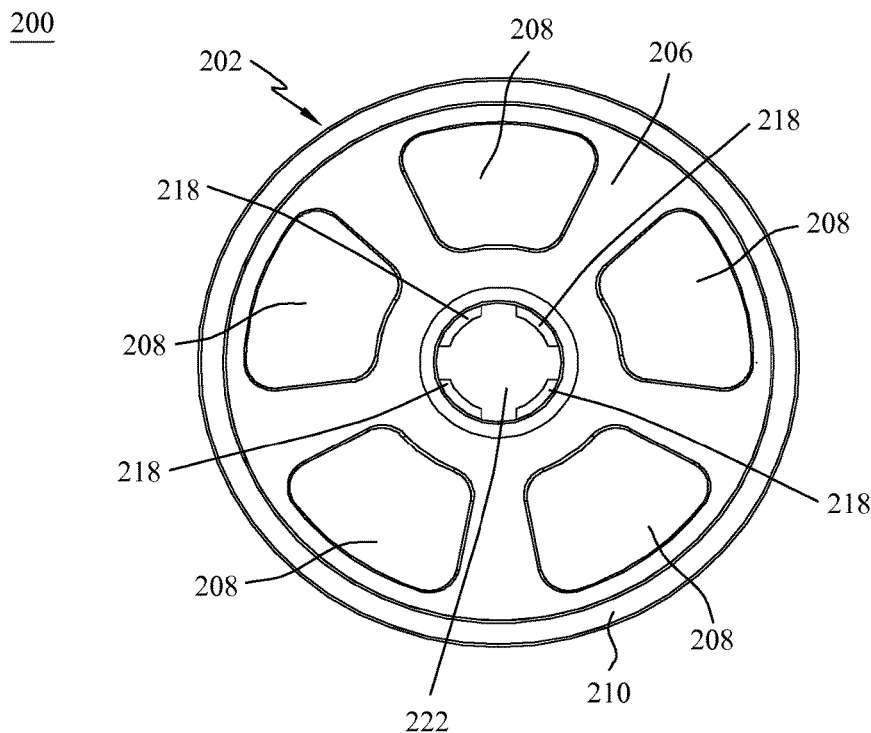
FIG. 28 is a bottom view of the reamer sleeve of FIG. 25, in accordance with an aspect of the present invention.
Figure 29:
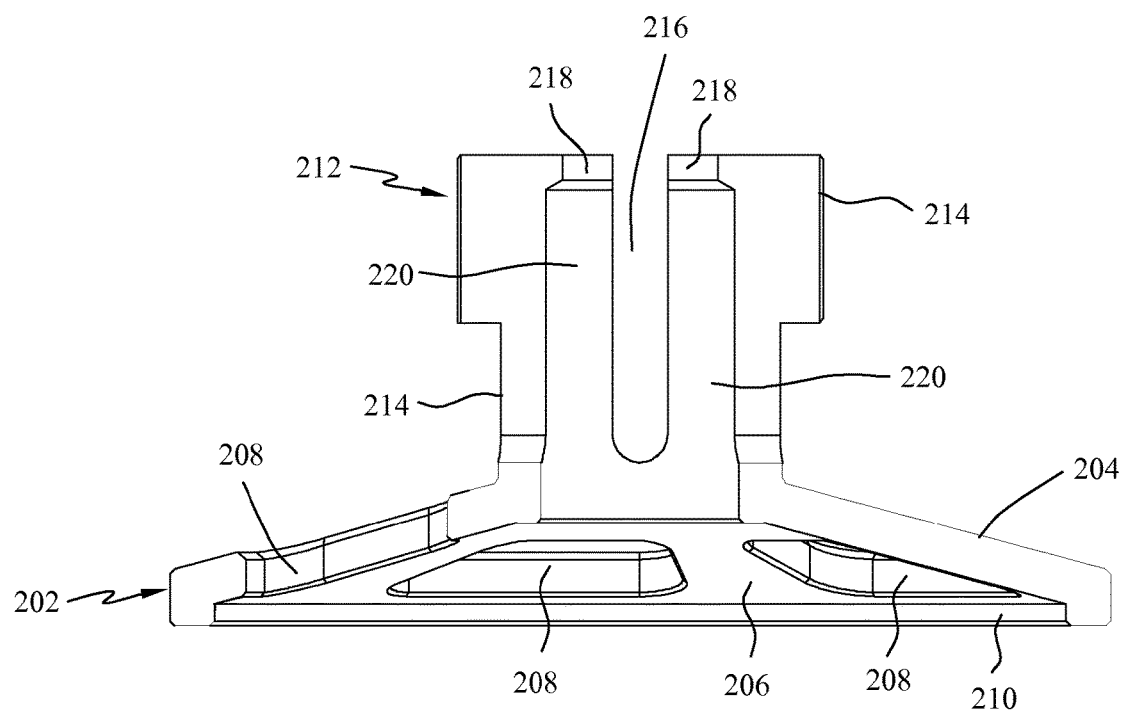
FIG. 29 is a cross-sectional view of the reamer sleeve of FIG. 25 taken along line 29-29 in FIG. 27, in accordance with an aspect of the present invention.

Referring now to FIGS. 25-29, another backstop or cup reamer sleeve 200 is shown. The terms "backstop," "cup reamer sleeve," "male reamer sleeve," "female reamer sleeve," "reamer sleeve," and "sleeve" may be used interchangeably herein as they essentially refer to the same structure. The term "male reamer sleeve" is used in reference to the reamer sleeve 200 being used with a male reamer and the term "female reamer sleeve" is used to describe the relationship with respect to the reamer sleeve 200 receiving the male reamer. The reamer sleeve 200 may include a base portion 202 and a collar portion or securement mechanism 212. The base portion 202 may include a top surface 204 and a bottom surface 206. The base portion 202 may have a thickness of, for example, approximately 0.25 mm to 2 mm. The base portion 202 may have a generally round or circular shape. The securement mechanism 212 may extend away from the top surface 204 of the base portion 202 near a center point of the base portion 202. The base portion 202 may also be angled in an opposite direction away from the securement mechanism 212 forming, for example, a circular pyramid shape. The top surface 204 and bottom surface 206 of the base portion 202 may be, for example, generally flat or planar, as shown in FIG. 29. The base portion 202 may also include at least one opening 208 extending from the top surface 204 to the bottom surface 206 of the base portion 202. The at least one opening 208 provides the surgeon with the ability to visualize the bone being reamed through the reamer sleeve 200 in order to determine when adequate bone has been resected and the subchondral bone exposed. In addition, the openings 208 may allow for the reamed material to escape or be removed from the site. As shown in FIGS. 27 and 28, the at least one opening 208 may be, for example, five openings 208. The base portion 202 may also include a rim 210 extending away from the bottom surface 206 of the base portion 202. The rim 210 may be positioned on the circumferential edge of the base portion 202.

Figure 25:
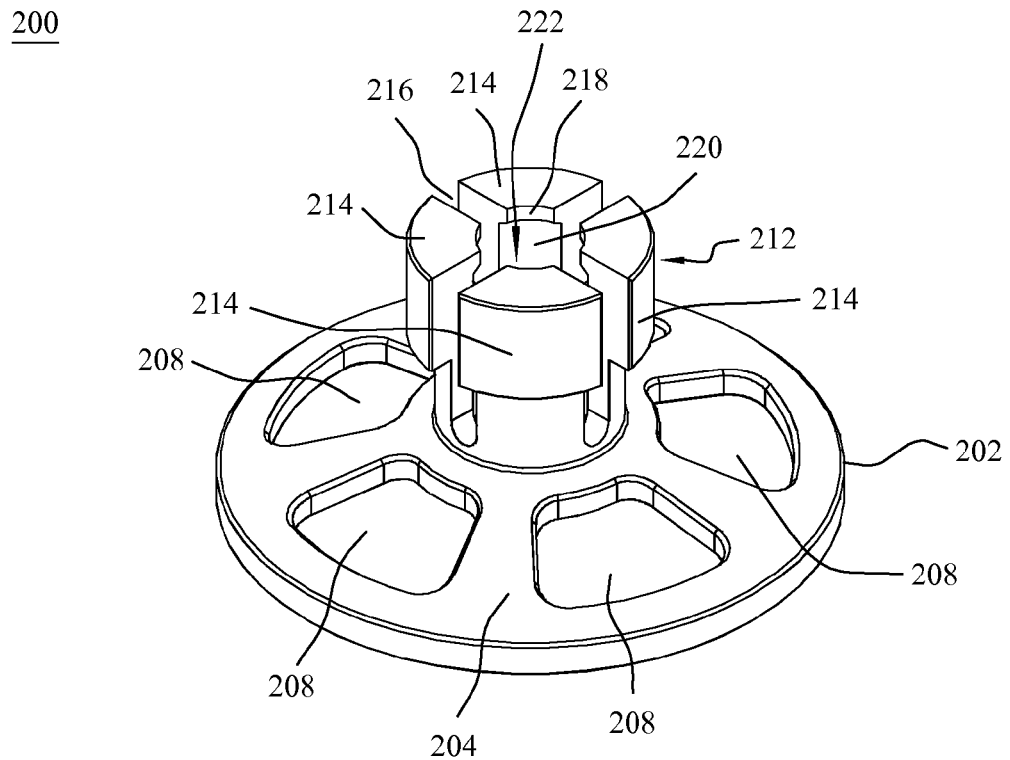
FIG. 25 is a perspective view of a reamer sleeve, in accordance with an aspect of the present invention.
Figure 26:
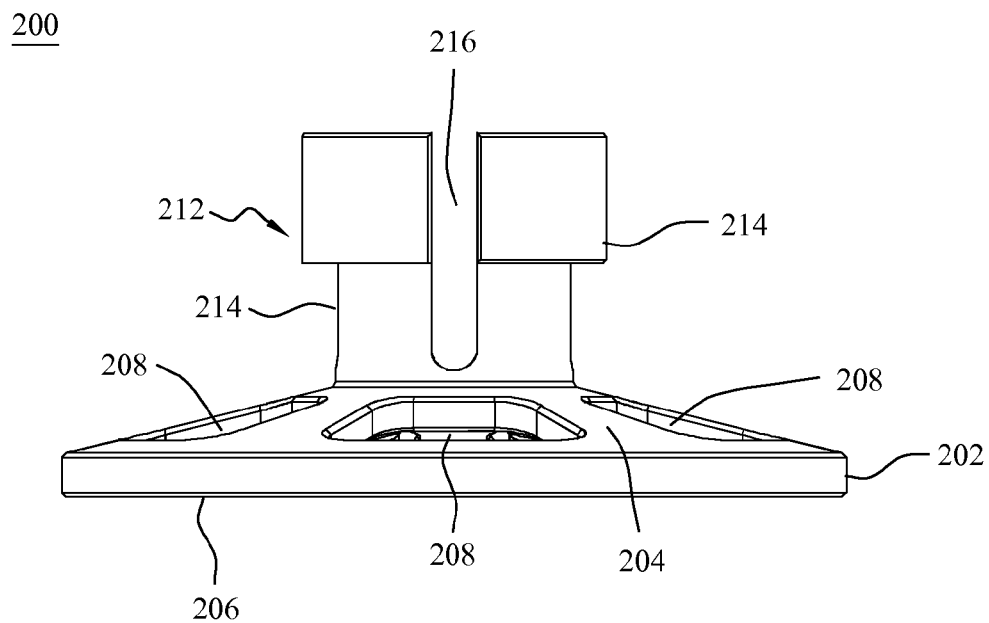
FIG. 26 is a side view of the reamer sleeve of FIG. 25, in accordance with an aspect of the present invention.

Referring now to FIGS. 25-29, the collar portion or securement mechanism 212 is shown and may include at least one engagement member 214 and an opening 222. The opening 222, as shown in FIGS. 25, 27 and 28, may extend from a top surface of the securement mechanism 212 through to the bottom surface 206 of the base portion 202 and be sized to fit over the shaft of a reamer, as described in greater detail below. The engagement members 214 may be separated by at least one channel 216. As shown in the depicted embodiment of FIGS. 25 and 27, the securement mechanism 212 may include, for example, four engagement members 214 and four channels 216, although alternative numbers of engagement members 214 and channels 216 are also contemplated, for example, approximately 1 to 10 engagement members 214 and approximately 1 to 10 channels 216. Each engagement member 214 may include an engagement protrusion or lip 218 extending out from the engagement member 214 and into the opening 222. The engagement members 214 may have varying thicknesses along the length of the securement mechanism 212 from the point of attachment with the base portion 202 to the top of the securement mechanism 212. For example, as shown in FIG. 29, the bottom portion of the engagement members 214 may be thinner than the top portion of the engagement members 214. In addition the thickest portion of the engagement members 214 may be where the lips 218 extend out from the engagement members 214. The varying thickness of the engagement members 214 may, for example, enable the engagement members 214 to deflect or to provide flexibility to the engagement members 214 when the reamer sleeve 200 is inserted on and removed from the reamer 230.

Referring now to FIGS. 30-35, an assembly including the reamer sleeve 200 and a male reamer 230 is shown. The terms "male reamer," "cup reamer" and "reamer" may be used interchangeably herein as they essentially refer to the same structure. The male reamer 230 may include a shank or shaft 232 with a first end and a second end. The shaft 232 may include an instrument mating surface 238 at the first end for coupling the reamer 230 to an instrument (not shown). The shaft 232 may also include an opening 242 extending from the first end to the second end for receiving, for example, a guide wire, pin, or the like to provide a guide for the reamer 230 to the appropriate cutting position. The shaft 232 may further include a groove 240 near the second end. The groove 240 may be sized to receive the at least one engagement protrusion 218 of the reamer sleeve 200. Although the groove 240 is depicted as being present around the entire circumferential surface of the shaft 232, it is also contemplated that the shaft 232 may include, for example, one or more separate grooves or recesses 240 to receive the at least one engagement protrusion 218 of the reamer sleeve 200. In this alternative embodiment (not shown), the number of grooves or recesses 240 would correspond directly to the number of engagement protrusions 218.

The reamer 230 may also include a cutting member 234 extending away from the second end, as shown in FIGS. 30-35. The cutting member 234 may also contain a plurality of blades or arms, which may have a generally convex bottom end with a rounded shape to enable cutting of a concave bone surface. The cutting member 234 may also include a planar or generally flat top surface which may be angled away from the second end of the shaft 232. The reamer sleeve 200 may be shaped to correspond to the shape of the top surface of the cutting member 234 to prevent contact between the cutting member 234 and reamer sleeve 200 during use. Thus, the shape of the base portion 202 of the reamer sleeve 200 may be, for example, generally flat or planar and angled away from the securement mechanism 212.

Figure 30:
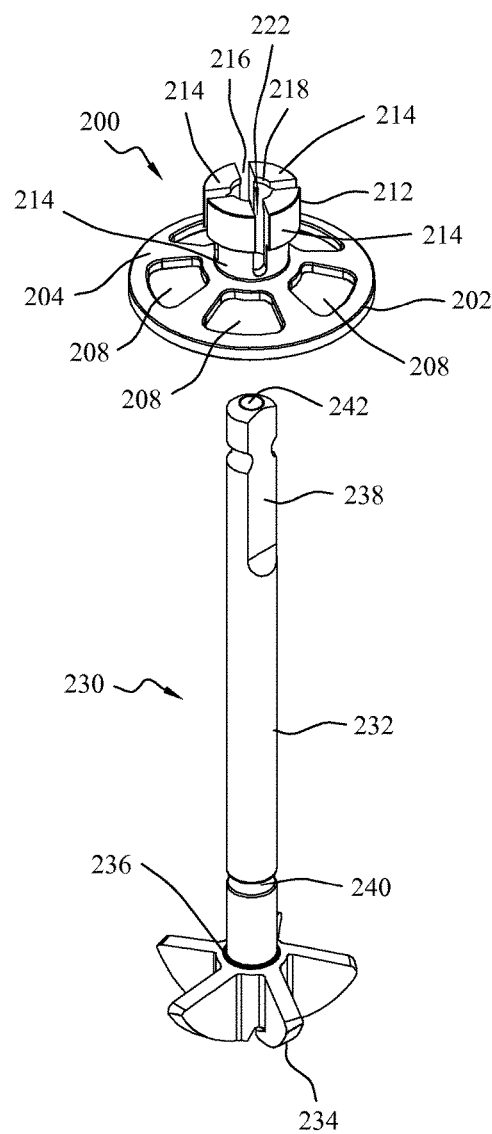
FIG. 30 is an exploded perspective view of a reamer assembly including the reamer sleeve of FIG. 25, in accordance with an aspect of the present invention.
Figure 31:
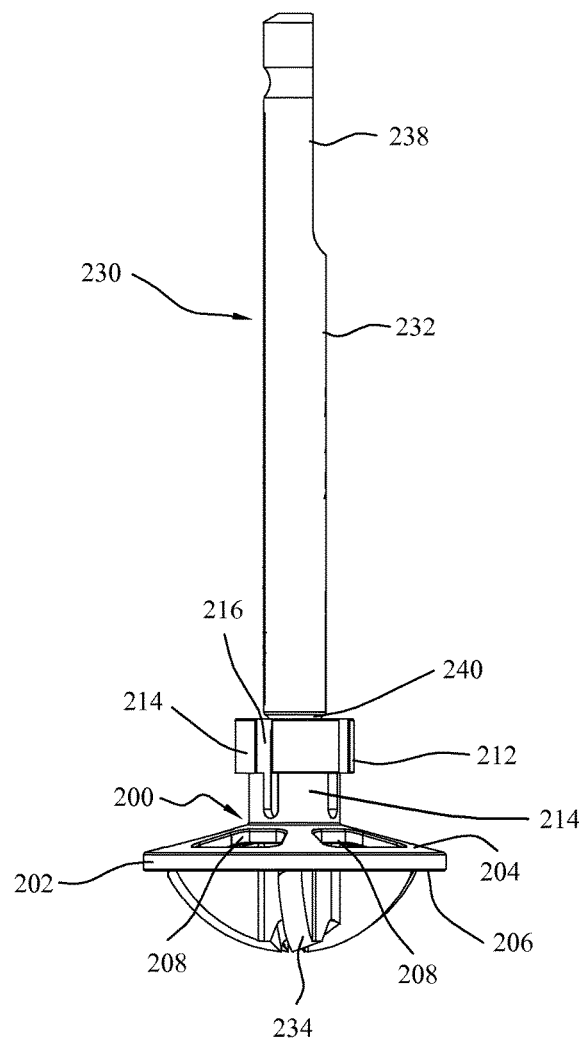
FIG. 31 is a side view of the reamer assembly of FIG. 30, in accordance with an aspect of the present invention.
Figures 32, 33:
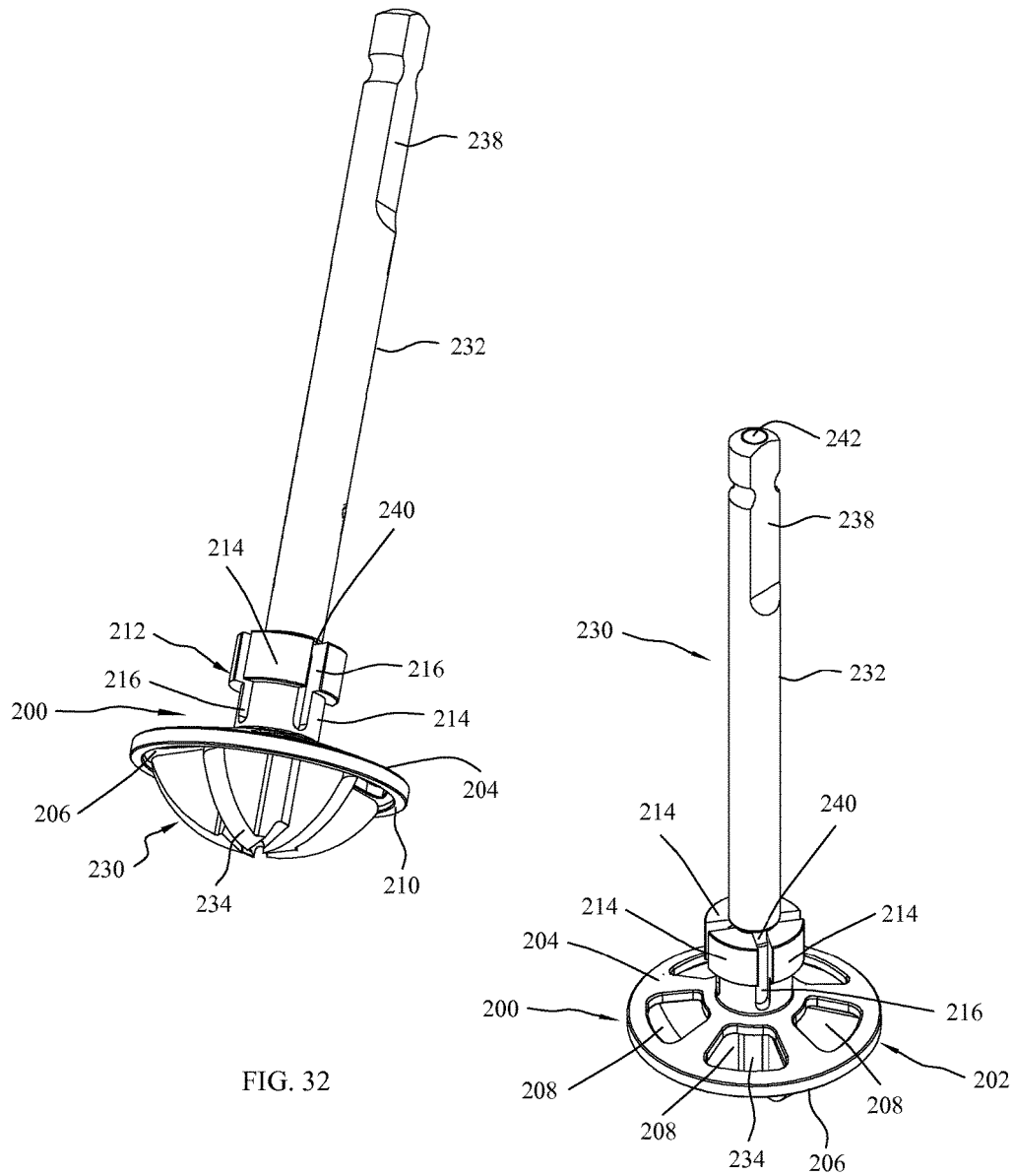
FIG. 32 is a bottom perspective view of the reamer assembly of FIG. 30, in accordance with an aspect of the present invention.
FIG. 33 is a top perspective view of the reamer assembly of FIG. 30, in accordance with an aspect of the present invention.

The assembly may further include, for example, a ring member 236 positioned where the cutting member 234 mates with the shaft 232, as shown in FIG. 30. The ring member 236 may act as a spacer to separate the reamer sleeve 200 from the cutting member 234. The ring member 236 may also allow the reamer sleeve 200 to float above the cutting member 234 as the reamer 230 spins to cut the patient's bone. The ring member 236 may be used to space the reamer sleeve 200 above the cutting member 234 in order to prevent the reamer sleeve 200 from catching on the reamer 230. If the reamer sleeve 200 was to catch on the reamer 230 it would act as an extension to the reamer 230 cutting the adjacent bone and causing unwanted damage to the surrounding bone or tissue. By floating the reamer sleeve 200 above the reamer 230, the reamer sleeve 200 is able to act independently of the reamer 230. For example, if the reamer sleeve 200 contacted surrounding bone or tissue during reaming, the reamer sleeve 200 would not be forced to spin with the reamer 230 and thus, would prevent damaging the surrounding bone and tissue. The ring member 236 may be, for example, integral with the reamer 230 or may be a separate member, such as, a washer or o-ring member that is slid over the shaft 232 of the reamer 230 prior to attachment of the reamer sleeve 200.

Figure 35:
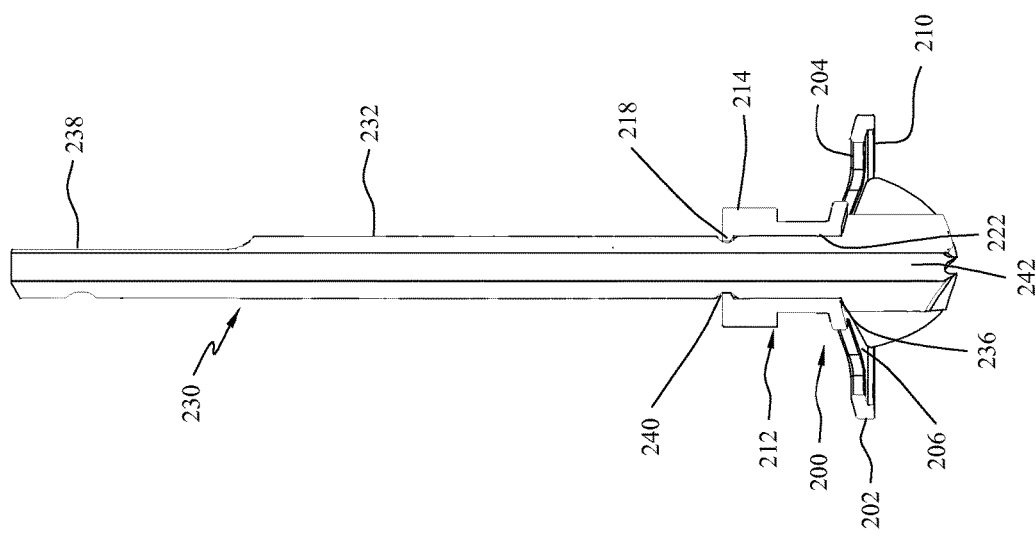
FIG. 35 is a cross-sectional view of the reamer assembly of FIG. 30 taken along line 35-35 of FIG. 34, in accordance with an aspect of the present invention.
Figure 34:
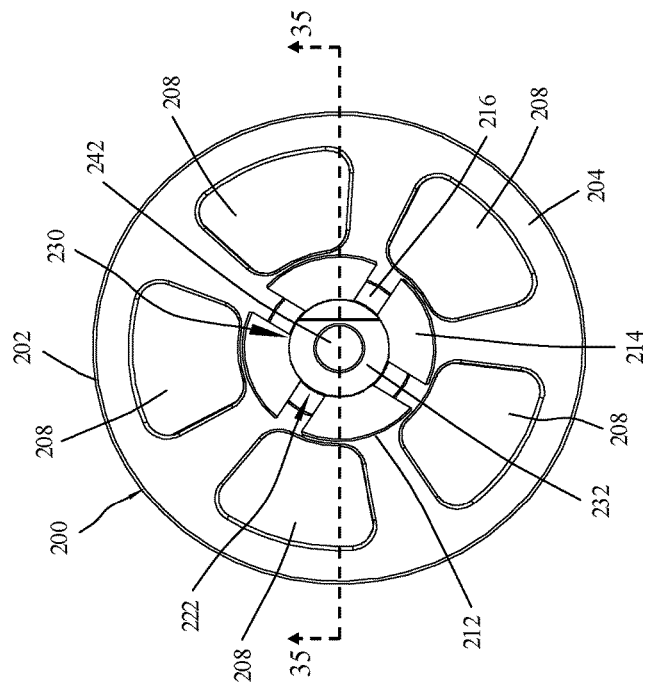
FIG. 34 is a top view of the reamer assembly of FIG. 30, in accordance with an aspect of the present invention.

With continued reference to FIGS. 30-35, the opening 222, as shown in FIGS. 30, 34 and 35, of the reamer sleeve 200 may be sized to slide over the shaft 232. The opening 222 may also be sized to maintain proper orientation between the reamer sleeve 200 and the shaft 232 of the reamer 230 to, for example, prevent the reamer sleeve 200 from tilting and engaging the reamer 230 during use. In addition, the proper orientation needs to be maintained in order to prevent, for example, seizing of the reamer sleeves 200 against the cutting member 234 of the reamer 230 and grinding of the metal reamer sleeve 200 on the metal reamer 230 which could produce particles or debris that could enter the surgical site. As the reamer sleeve 200 is slid down the shaft 232 of the reamer 230, the at least one engagement protrusion 218 will slide along the shaft 232 of the reamer 230 until the at least one engagement protrusion 218 engages the groove 240 in the shaft 232, as shown in FIGS. 31-33 and 35. The at least one engagement protrusion 218 fits into the groove 240 to moveably couple the reamer sleeve 200 to the reamer 230. The groove 240 and engagement protrusion 218 act to secure the reamer sleeve 200 to the shaft 232 of the reamer 230 to ensure the reamer sleeve 200 does not translate on the reamer shaft 232 as centrifugal force is introduced to the reamer 230. It is desirable to have engagement protrusions 218 which secure the reamer sleeve 200 to the shaft 232 to prevent certain movement, for example, translation in a proximal/distal direction or a medial/lateral direction, of the reamer sleeve 200 during reaming of the patient's bones. However, it is also desirable for the reamer sleeve 200 to be able to rotate freely with respect to the reamer 230. Thus, as the reamer 230 rotates to ream a patient's bone, the reamer sleeve 200 may rotate freely or may remain stationary to prevent damage to the surrounding tissue. For example, if the reamer sleeve 200 contacted the adjacent bone or tissue the ability of the reamer sleeve 200 to rotate freely would allow for the reamer sleeve 200 to remain stationary as the reamer 230 continued to spin and would prevent damage being caused to the bone contacted by the reamer sleeve 200. In addition, it is desirable for the engagement protrusions 218 to be able to be disengaged from the groove 240 by applying force to the reamer sleeve 200. By allowing the engagement protrusions 218 to be released from the groove 240, the reamer sleeve 200 may slide toward the first end of the shaft 232 of the reamer 230. The reamer sleeve 200 may be translated up the shaft 232 in order to provide the space needed to remove bone debris which may build up on the reamer during the reaming and to also allow for verification that the desired amount of bone cartilage was removed.

Figure 38:
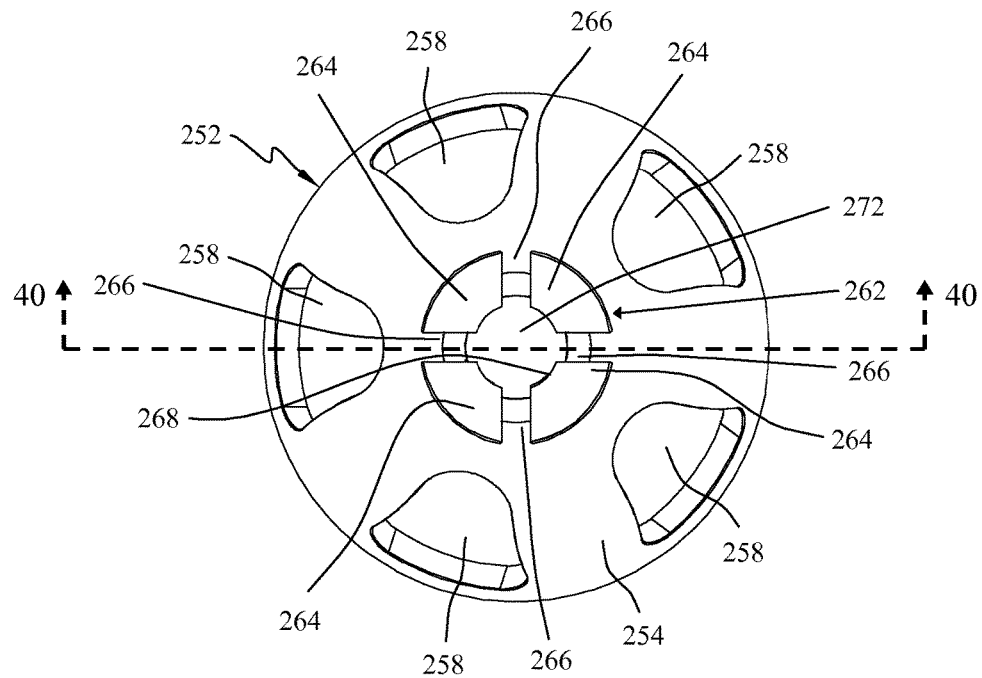
FIG. 38 is a top view of the reamer sleeve of FIG. 36, in accordance with an aspect of the present invention.
Figure 39:
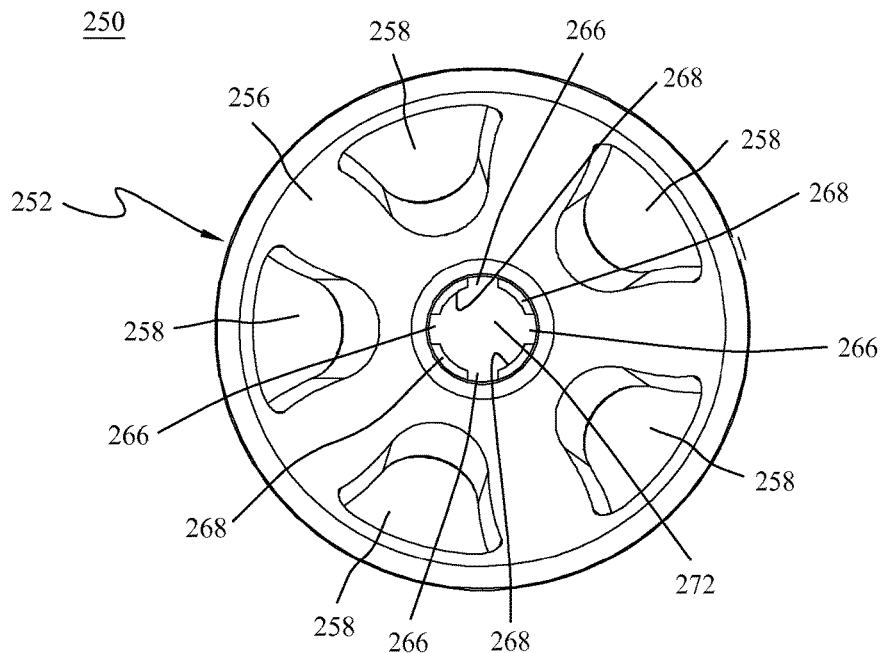
FIG. 39 is a bottom view of the reamer sleeve of FIG. 36, in accordance with an aspect of the present invention.
Figure 40:
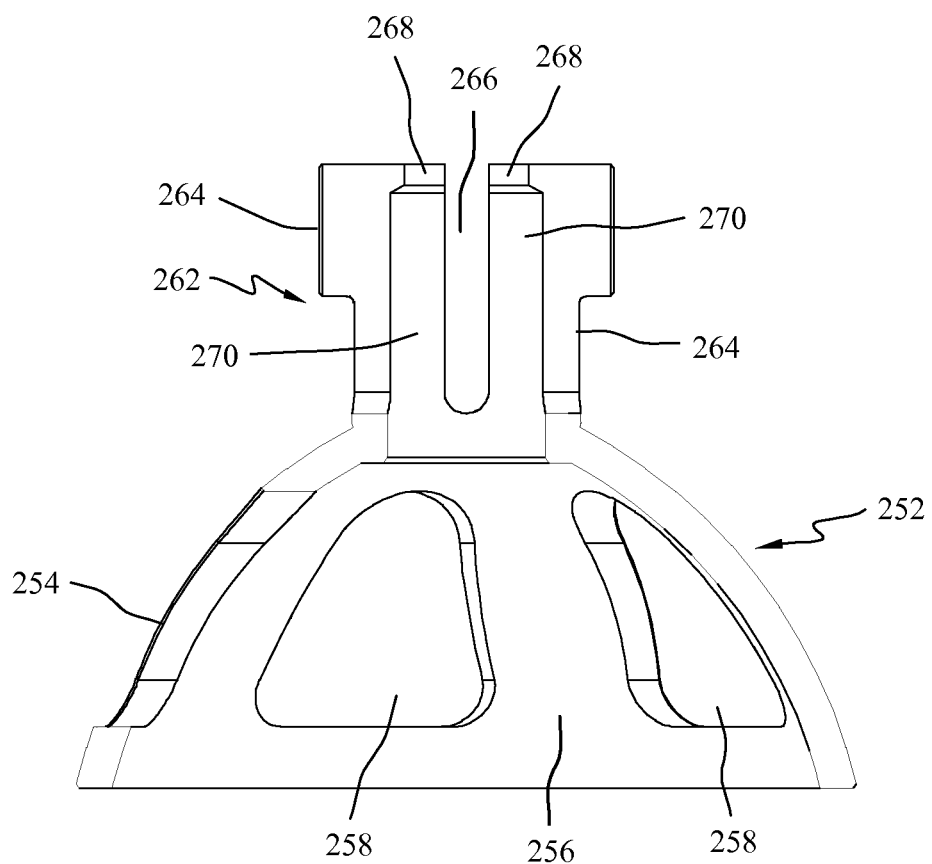
FIG. 40 is a cross-sectional view of the reamer sleeve of FIG. 36 taken along line 40-40 in FIG. 38, in accordance with an aspect of the present invention.

Referring now to FIGS. 36-40, another backstop or cone reamer sleeve 250 is shown. The terms "backstop," "cone reamer sleeve," "female reamer sleeve," "reamer sleeve," and "sleeve" may be used interchangeably herein as they essentially refer to the same structure. The term "female reamer sleeve" is used with respect to reamer sleeve 250 to describe both that reamer sleeve 250 is used with a female reamer and to describe the shape of the reamer sleeve 250 being such that it receives the convex surface of a female reamer 280. The reamer sleeve 250 may include a base portion 252 and a collar portion or securement mechanism 262. The base portion 252 may include a top surface 254 and a bottom surface 256. The base portion 252 may have a thickness of, for example, approximately 0.25 mm to 2 mm. The securement mechanism 262 may extend away from the top surface 254 of the base portion 252 near a center point of the base portion 252. The base portion 252 may have, for example, a generally domed, cone, arcuate, or curved shape extending away from the securement mechanism 262. The top surface 254 of the base portion 252 may be a generally convex surface and the bottom surface 256 of the base portion 252 may be a generally concave surface. The base portion 252 may also include at least one opening 258 extending from the top surface 254 through to the bottom surface 256 of the base portion 252. The at least one opening 258 provides the surgeon the ability to visualize the bone being reamed through the reamer sleeve 250. The visualization allows for the surgeon to determine when adequate bone has been resected and the subchondral bone is exposed. In addition, the openings 258 may allow for the reamed material to escape or be removed from the target site. As shown in FIGS. 38 and 39, the at least one opening 258 may be, for example, five openings 258.

Figure 36:
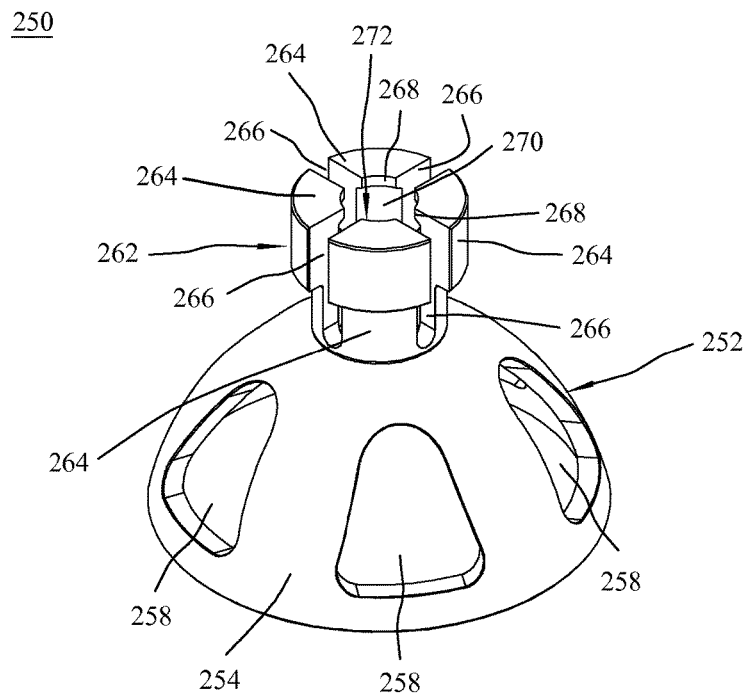
FIG. 36 is a perspective view of another embodiment of a reamer sleeve, in accordance with an aspect of the present invention.
Figure 37:
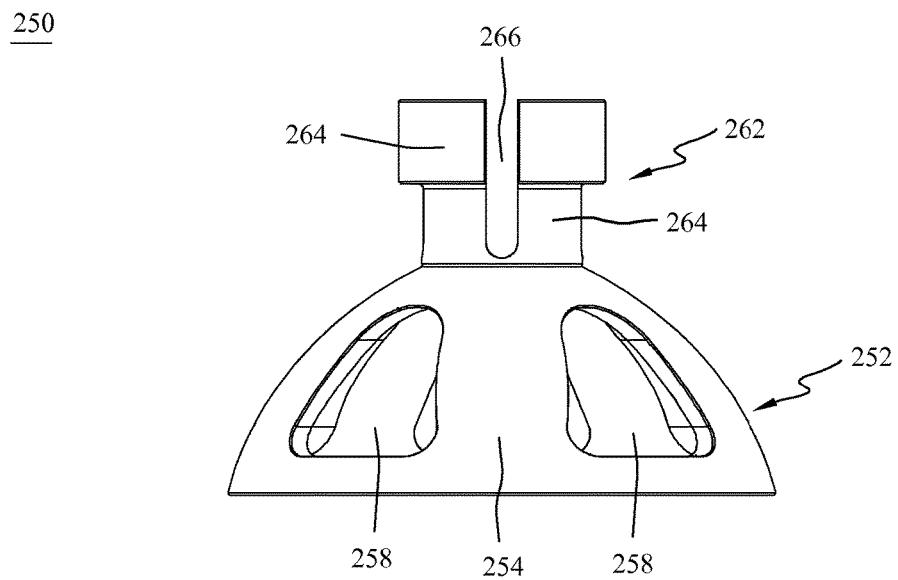
FIG. 37 is a side view of the reamer sleeve of FIG. 36, in accordance with an aspect of the present invention.

The securement mechanism 262 may include at least one engagement member 264, as shown in FIGS. 36-40, and an opening 272, as shown in FIGS. 36, 38, and 39. The opening 272 may extend from a top surface of the securement mechanism 262 through to the bottom surface 256 of the base portion 252 and be sized to fit over the shaft of a reamer, as described in greater detail below. The engagement members 268 may be separated by at least one channel 266. As shown in the depicted embodiment, the securement mechanism 262 may include, for example, four engagement members 264 and four channels 266, although other numbers of engagement members 264 and channels 266 are also contemplated, for example, approximately 1 to 10 engagement members 264 and approximately 1 to 10 channels 266. Each engagement member 264 may include an engagement protrusion or lip 268 extending out from the engagement member 264 and into the opening 272. The securement mechanism 262 may be of the type described above with reference to the securement mechanism 212, which will not be described again here in complete detail for brevity sake.

Referring now to FIGS. 41-46, an assembly including the reamer sleeve 250 and a female reamer 280 is shown. The terms "female reamer," "cone reamer" and "reamer" may be used interchangeably herein as they essentially refer to the same structure. The female reamer 280 may include a shank or shaft 282 with a first end and a second end. The shaft 282 may be of the type described above with reference to shaft 232. The shaft 282 may include an instrument mating surface 288, an opening 292, and a groove 290, similar to the mating surface 238, opening 242, and groove 240 as described above with reference to FIGS. 30-35, and which will not be described again here for brevity sake.

The reamer 280 may also include a cutting member 284 extending away from the second end, as shown in FIGS. 41-46. The cutting member 284 may contain a plurality of blades or arms, which may have a generally concave end with a curved shape to enable cutting of a convex bone surface. The cutting member 284 may also include a generally curved top surface which may be curved away from the second end of the shaft 282. The reamer sleeve 250 may be shaped to correspond to the shape of the top surface of the cutting member 284. Thus, the shape of the base portion 252 of the reamer sleeve 250 may be, for example, generally curved away from the securement mechanism 262.

Figures 41, 42:
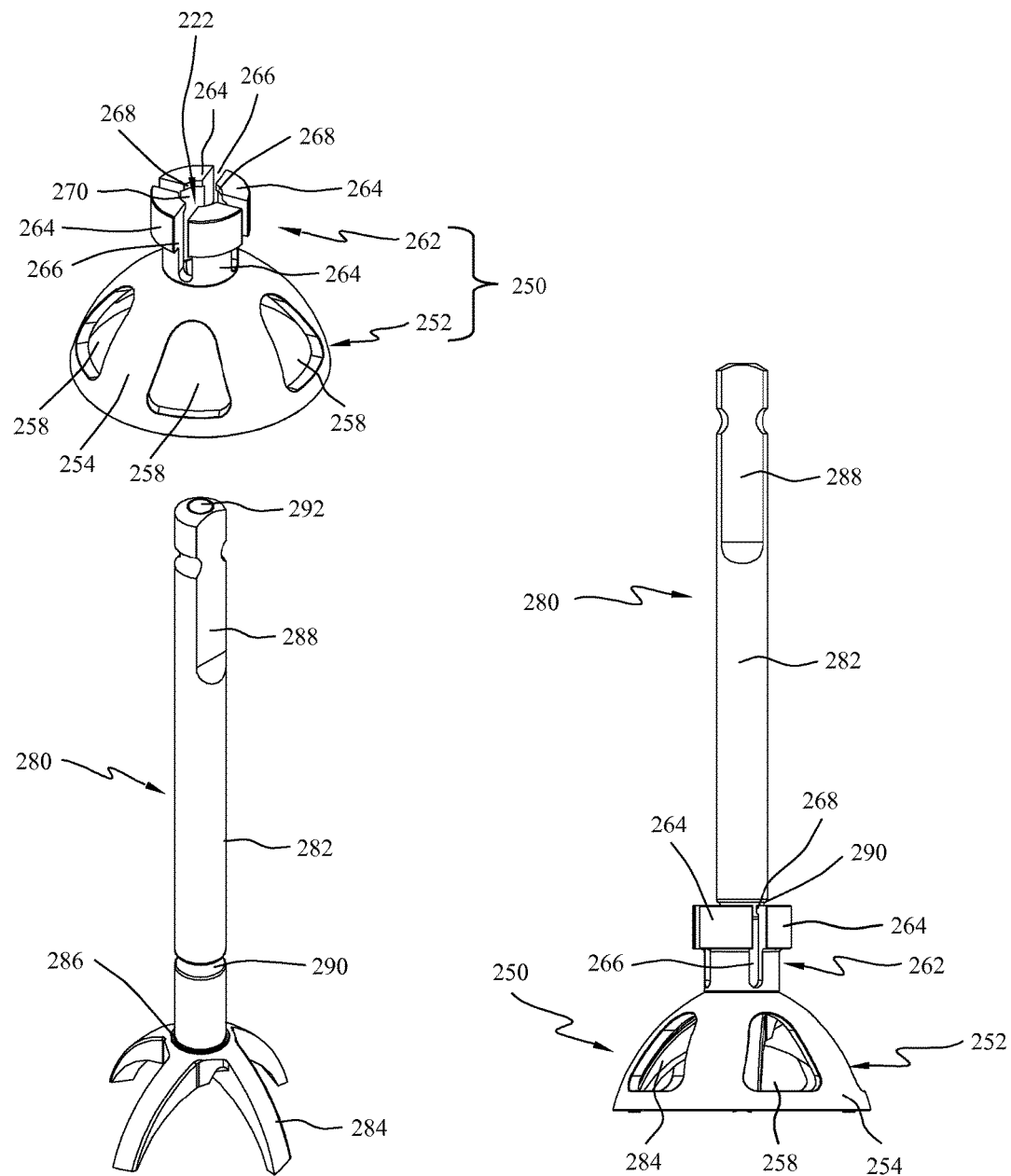
FIG. 41 is an exploded perspective view of a reamer assembly including the reamer sleeve of FIG. 36, in accordance with an aspect of the present invention.
FIG. 42 is a side view of the reamer assembly of FIG. 41, in accordance with an aspect of the present invention.
Figure 47:
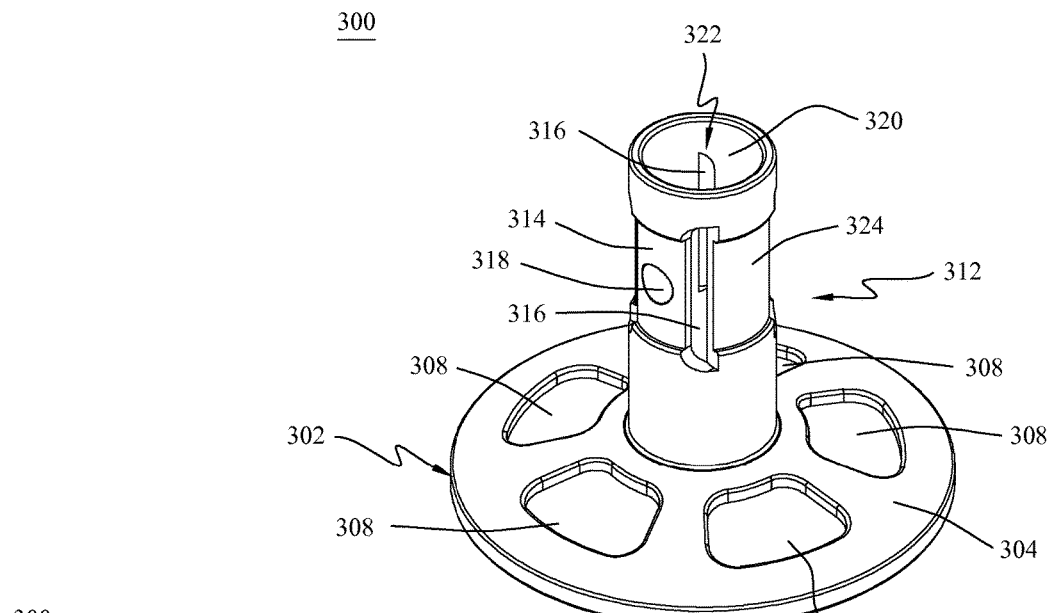
FIG. 47 is a top perspective view of an embodiment of a reamer sleeve, in accordance with an aspect of the present invention.
Figure 48:
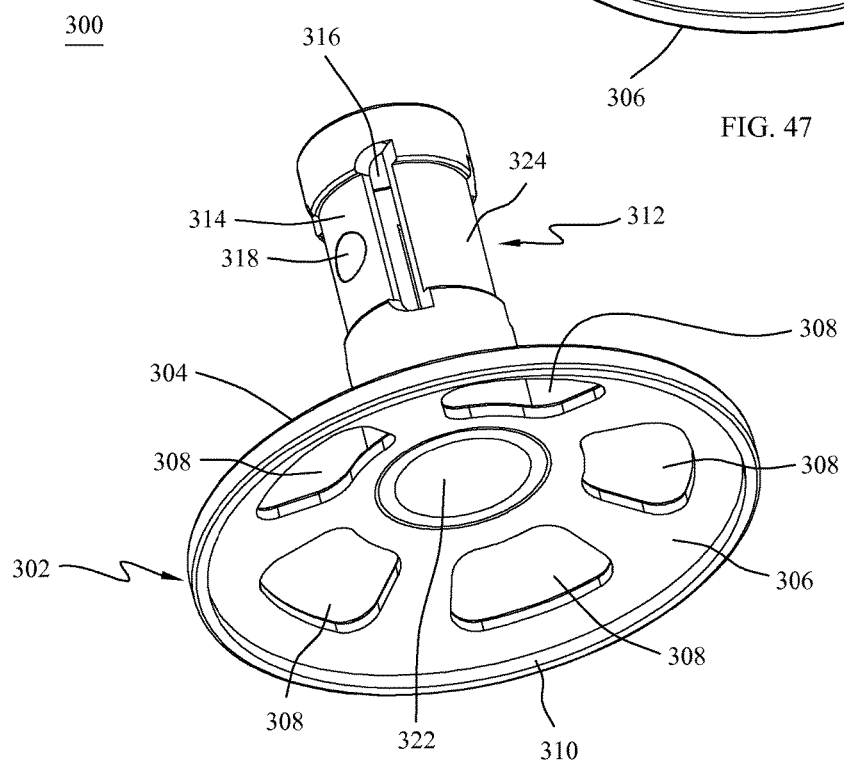
FIG. 48 is a bottom perspective view of the reamer sleeve of FIG. 47, in accordance with an aspect of the present invention.
Figure 49:
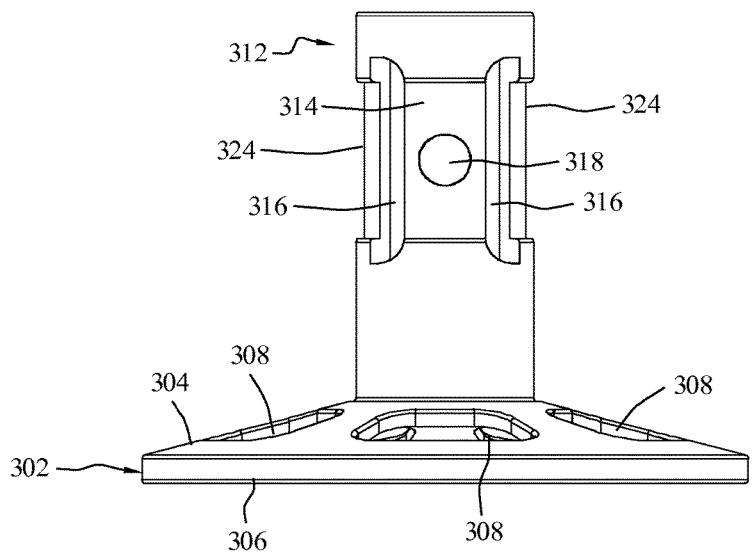
FIG. 49 is a side view of the reamer sleeve of FIG. 47, in accordance with an aspect of the present invention.
Figure 50:
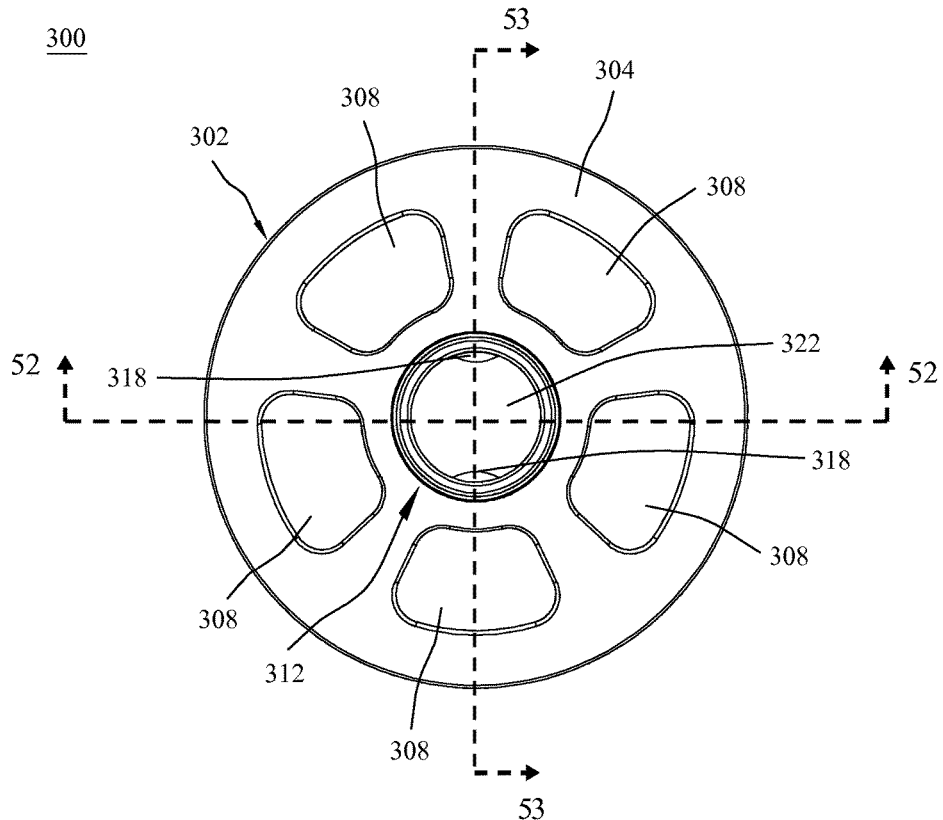
FIG. 50 is a top view of the reamer sleeve of FIG. 47, in accordance with an aspect of the present invention.
Figure 51:
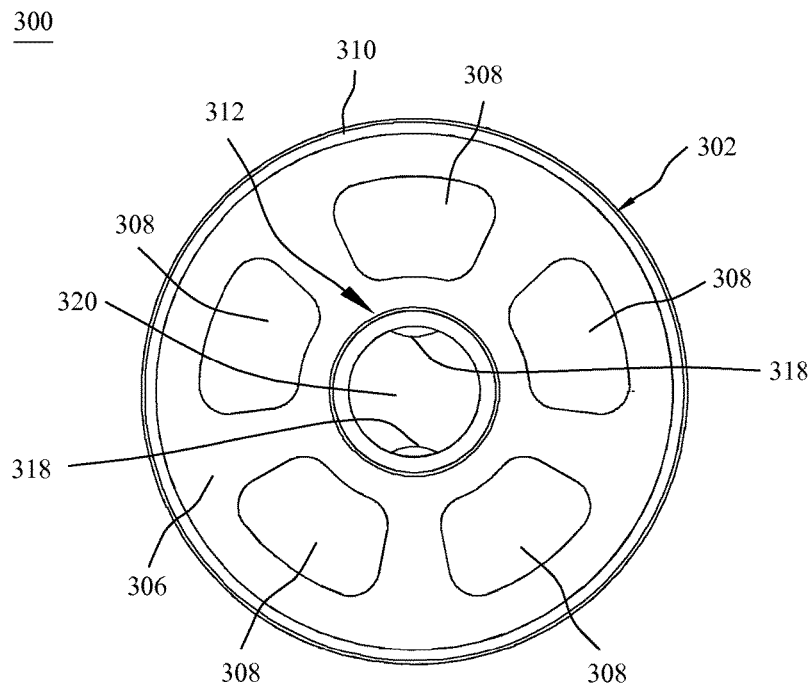
FIG. 51 is a bottom view of the reamer sleeve of FIG. 47, in accordance with an aspect of the present invention.
Figure 52:
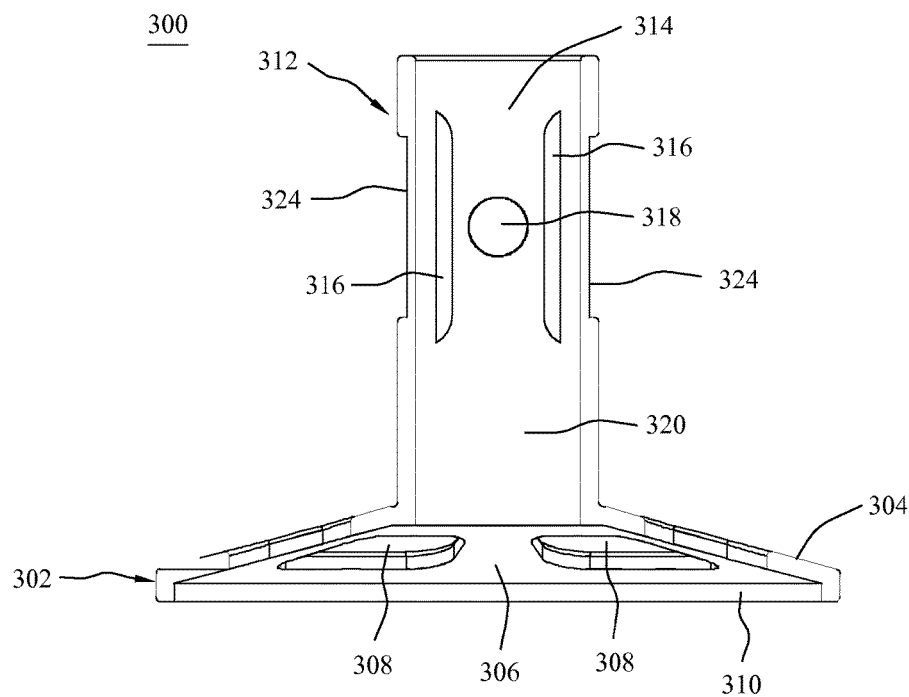
FIG. 52 is a cross-sectional view of the reamer sleeve of FIG. 47 taken along line 52-52 in FIG. 50, in accordance with an aspect of the present invention.
Figure 53:
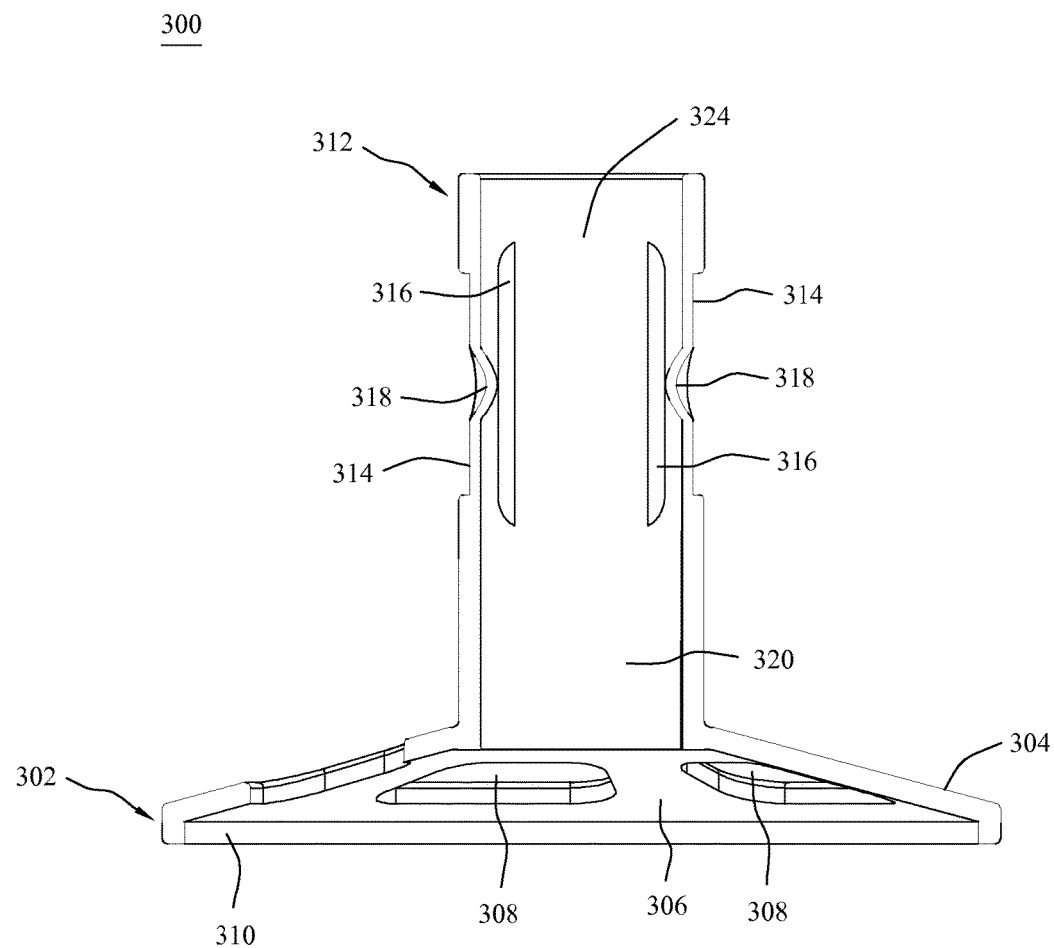
FIG. 53 is a cross-sectional view of the reamer sleeve of FIG. 47 taken along line 53-53 in FIG. 50, in accordance with an aspect of the present invention.
Figure 54:
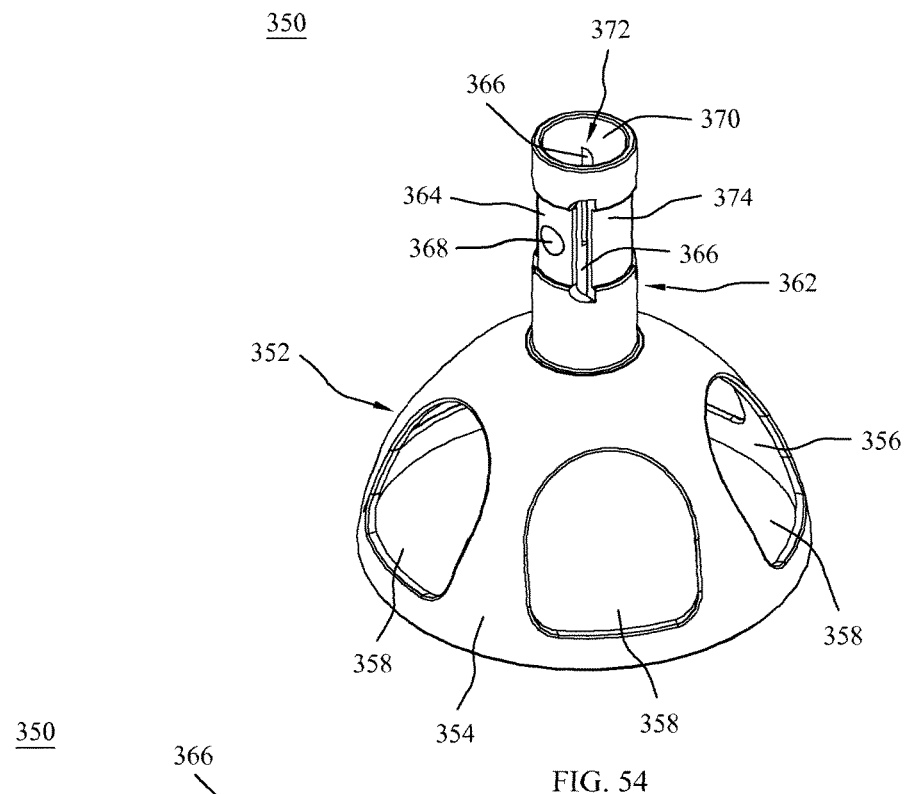
FIG. 54 is a top perspective view of another embodiment of a reamer sleeve, in accordance with an aspect of the present invention.
Figure 55:
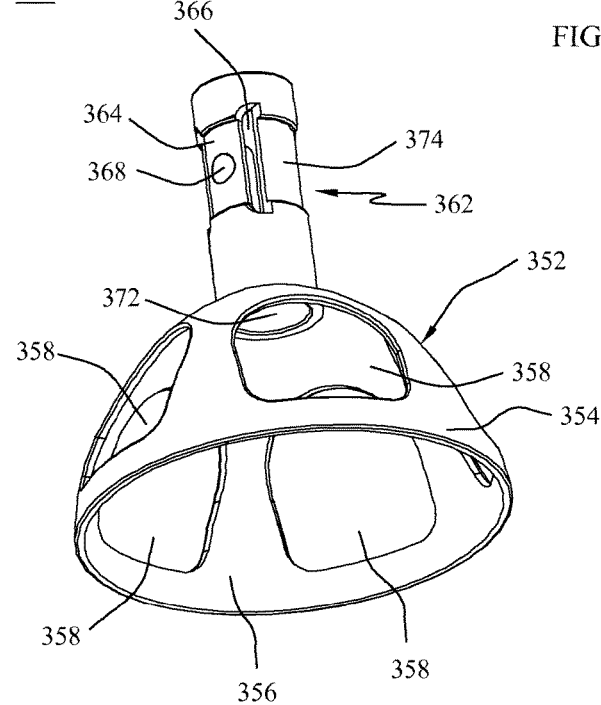
FIG. 55 is a bottom perspective view of the reamer sleeve of FIG. 54, in accordance with an aspect of the present invention.
Figure 58:
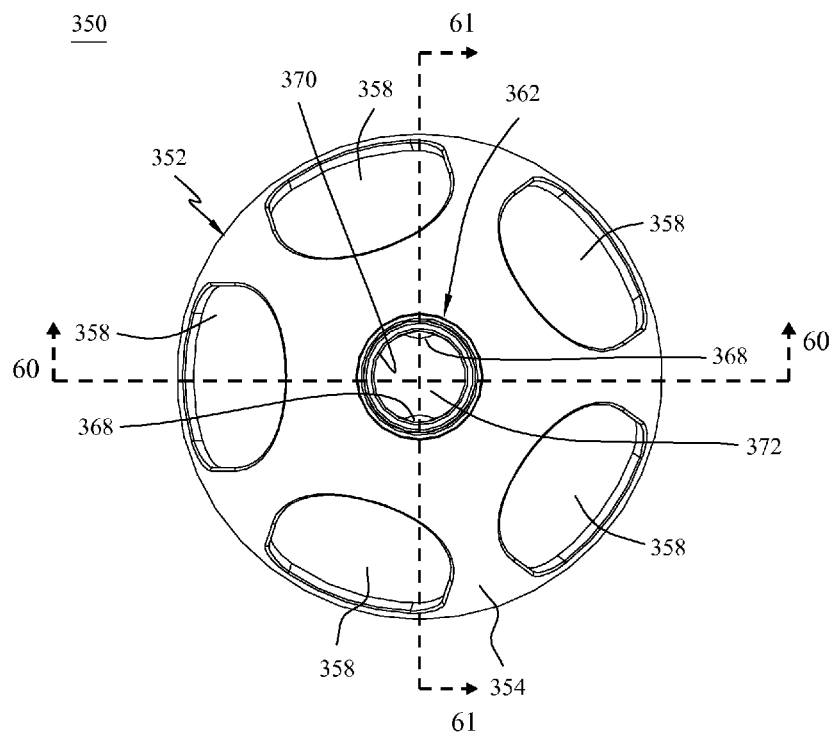
FIG. 58 is a top view of the reamer sleeve of FIG. 54, in accordance with an aspect of the present invention.
Figure 59:
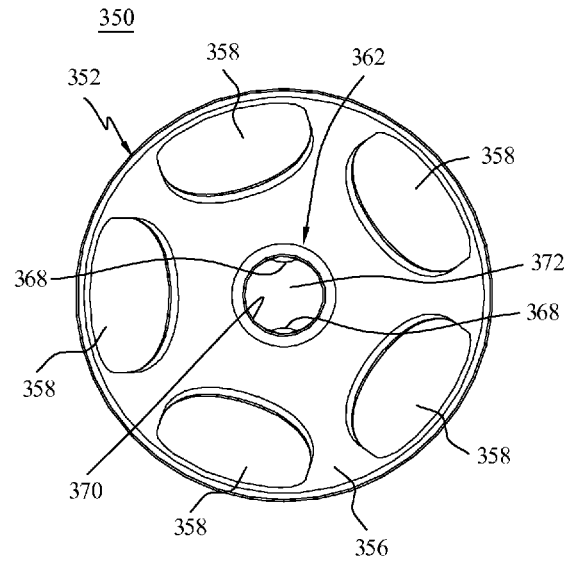
FIG. 59 is a bottom view of the reamer sleeve of FIG. 54, in accordance with an aspect of the present invention.

With continued reference to FIGS. 41-46, the assembly may further include, for example, a ring member 286, as shown in FIG. 41, positioned where the cutting member 284 mates with the shaft 282. The ring member 286 may act as a spacer to separate the reamer sleeve 250 from the cutting member 284. The ring member 286 may further be of the type described above with reference to ring member 236 and will not be described again here for brevity sake. The opening 272 of the reamer sleeve 250 may be sized to slide over the shaft 282. The opening 272, as shown in FIG. 41, may be sized as described above with reference to opening 222, which will not be described again here for brevity sake.

The assembly may be formed by sliding the reamer sleeve 250 down the shaft 282 of the reamer 280. As the reamer sleeve 250 travels down the shaft 282, the at least one engagement protrusion 268 will slide along the shaft 282 of the reamer 280 until the at least one engagement protrusion 268 engages the groove 290 in the shaft 282, as shown in FIGS. 42-44 and 46. The at least one engagement protrusion 268 fits into the groove 290 to couple the reamer sleeve 250 to the reamer 280. The groove 290 and the at least one engagement protrusion 268 act to secure the reamer sleeve 250 to the shaft 282 of the reamer 280 to ensure the reamer sleeve 250 does not translate on the reamer shaft 282 as centrifugal force is introduced to the reamer 280. It is desirable to have the at least one engagement protrusion 268 that secures the reamer sleeve 250 to the shaft 282 to prevent movement in certain directions with respect to the longitudinal axis of the shaft 282 during rotation of the assembly, for example, to prevent translation along the longitudinal axis of the shaft 282 or angulation of the reamer sleeve 250 with respect to the longitudinal axis of the shaft 282. However, it is also desirable for the reamer sleeve 250 to be able to rotate freely with respect to the reamer 280. Thus, as the reamer sleeve 250 is not fixed to the reamer 280, the reamer sleeve 250 may rotate freely or remain stationary as the reamer 280 rotates to prevent damage to the surrounding tissue. For example, if the reamer sleeve 250 contacts adjacent bone or tissue the reamer sleeve 250 may remain stationary as the reamer 280 continues to spin to prevent damage to the surrounding bone or tissue contacted by the reamer sleeve 250. In addition, it is desirable for the engagement protrusions 268 to be able to disengage from the groove 290 by applying force to the reamer sleeve 250. By allowing the engagement protrusions 268 to be released from the groove 290, the reamer sleeve 250 may slide toward the first end of the shaft 282 of the reamer 280. The reamer sleeve 250 may be translated up the shaft 282 in order to provide the space needed to remove bone debris which may build up on the reamer during the reaming and to also allow for verification that the desired amount of bone cartilage was removed.

Referring now to FIGS. 47-53, another backstop or reamer sleeve 300 is shown. The reamer sleeve 300 may include a base portion 302 and a collar portion or securement mechanism 312. The base portion 302 may be of the type described above with reference to base portion 202. The base portion 302 may include a top surface 304, a bottom surface 306, at least one opening 308, and a rim 310 which may be similar to the top surface 204, bottom surface 206, at least one opening 208, and rim 210, which will not be described again here for brevity sake.

The securement mechanism 312, as shown in FIGS. 47-53, may include a first end, a second end, and an opening 322 extending from the first end to the second end and forming an interior surface 320. The second end of the securement mechanism 312 may be coupled to the base portion 302. The securement mechanism 312 may also include at least one deformable member 314, at least one aperture 316, and at least one side member 324 positioned between the first end and second end of the securement mechanism 312. The terms "deformable member" and "engagement member" may be used interchangeably herein as they each refer to a structure of the securement mechanism 312 that moves when a force is applied. The at least one aperture 316 may be positioned between the at least one deformable member 314 and the at least one side member 324. The securement mechanism 312 may have, for example, two deformable members 314, four apertures 316, and two side members 324, as shown in the depicted embodiment. Alternative numbers of deformable members 314, apertures 316, and side members 324 are also contemplated. The at least one deformable member 314 may include at least one engagement protrusion 318 extending from the interior surface 320 into the opening 322. The at least one deformable member 314 may have a thickness that is less than the thickness of the surrounding securement mechanism 312 to enable the deformable member 314 to flex during assembly with a reamer, such as, reamer 110, 112, 230, and 280. The side members 324 may also have a thickness that is less than the thickness of the surrounding securement mechanism 312, although it is also contemplated that the thickness of the side members 324 and surrounding securement mechanism 312 may be equal.

The reamer sleeve 300, as shown in FIGS. 47-53, may be assembled with a reamer, such as, reamer 112, 230, or a like male reamer, by aligning the opening 322 of the reamer sleeve 300 with the shaft 120, 232 and sliding the reamer sleeve 300 down the shaft 120, 232 toward the cutting member 122, 234. As the reamer sleeve 300 is moved down the shaft 120, 232 of the reamer 112, 230, the at least one engagement protrusion 318 slides along the shaft 120, 232 until the at least one engagement protrusion 318 engages the groove 240 in the shaft 120, 232. The at least one engagement protrusion 318 fits into the groove 240 to couple the reamer sleeve 300 to the reamer 112, 230. The groove 240 and the engagement protrusion 318 act to secure the reamer sleeve 300 to the shaft 120, 232 of the reamer 112, 230 to ensure the reamer sleeve 300 does not translate on the reamer shaft 120, 232 as centrifugal force is introduced to the reamer 112, 230. The engagement protrusions 318 may also act to prevent movement in certain directions with respect to the longitudinal axis of the shaft 120, 232 during rotation of the assembly, for example, to prevent translation along the longitudinal axis of the shaft 120, 232 or prevent angulation or tilting of the reamer sleeve 300 with respect to the longitudinal axis. The engagement protrusions 318 may act with a ring member, such as, ring member 236, 286, on the shaft 120, 232 to keep the reamer sleeve 300 from contacting the cutting member 122, 234 of the reamer 112, 230. In addition, the engagement protrusions 318 may be disengaged from the groove 240 by applying force to the reamer sleeve 300 along the longitudinal axis. By allowing the engagement protrusions 318 to be released from the groove 240, the reamer sleeve 300 may be translated along the longitudinal axis toward the first end of the shaft 120, 232 of the reamer 112, 230. The reamer sleeve 300 may be moved away from the cutting member 122, 234 to provide the space needed to remove bone debris that may build up on the reamer 112, 230 during reaming and to allow for verification that the desired amount of bone cartilage was removed. Further, the engagement protrusions 218 allow for the sleeve 300 to rotate freely with respect to a reamer 112, 230. As the sleeve 300 is not fixed to the reamer 112, 230, the sleeve 300 may be stationary as the reamer 112, 230 rotates or alternatively the sleeve 300 may rotate as the reamer 112, 230 rotates. The free rotation of the reamer sleeve 300 allows for the sleeve 300 to remain stationary if it contacts any surrounding bone or tissue to prevent damage to that bone or tissue.

Referring now to FIGS. 54-61, another backstop or reamer sleeve 350 is shown. The reamer sleeve 350 may include a base portion 352 and a collar portion or securement mechanism 362. The base portion 352 may be of the type described above with reference to base portion 252. The base portion 352 may include a top surface 354, a bottom surface 356, and at least one opening 358 which may be similar to the top surface 254, bottom surface 256, and at least one opening 258 which will not be described again here for brevity sake.

The collar portion or securement mechanism 362, as shown in FIGS. 54-61, may include a first end, a second end, and an opening 372 extending from the first end to the second end and forming an interior surface 370. The securement mechanism 362 may be of the type described above with reference to securement mechanism 312, which will not be described in detail here for brevity sake. The second end of the securement mechanism 362 may be coupled to the base portion 352. The securement mechanism 362 may include at least one deformable member 364, at least one aperture 366, and at least one side member 374 positioned between the first end and second end of the securement mechanism 362. The at least one deformable member 364, at least one aperture 366, and the at least one side member 374 may be of the type described above with reference to at least one deformable member 314, at least one aperture 316, and the at least one side member 324, which will not be described again here for brevity sake.

The reamer sleeve 350, as shown in FIGS. 54-61, may be assembled with a reamer, such as, reamer 110, 280, or a like female reamer, by aligning the opening 372 of the reamer sleeve 350 with the shaft 114, 282 and sliding the reamer sleeve 350 down the shaft 114, 282 toward the cutting member 116, 284. As the reamer sleeve 350 is moved down the shaft 114, 282 of the reamer 110, 280, the at least one engagement protrusion 368 slides along the shaft 114, 282 until the at least one engagement protrusion 368 engages the groove 290 in the shaft 114, 282. The at least one engagement protrusion 368 fits into the groove 290 to couple the reamer sleeve 350 to the reamer 110, 280. The groove 290 and the engagement protrusion 368 act to secure the reamer sleeve 350 to the shaft 114, 282 of the reamer 110, 280 to ensure the reamer sleeve 350 does not translate on the reamer shaft 114, 282 as centrifugal force is introduced to the reamer 110, 280. The engagement protrusions 368 may also act to prevent movement in certain directions with respect to the longitudinal axis of the shaft 114, 282 as described above with reference to engagement protrusions 318 and which will not be described again here for brevity sake. The engagement protrusions 368 may act with a ring member, such as, ring member 236, 286, on the shaft 114, 282 to keep the reamer sleeve 350 from contacting the cutting member 116, 284 of the reamer 110, 280. In addition, the engagement protrusions 368 may be disengaged from the groove 290 by applying force to the reamer sleeve 350 along the longitudinal axis. By allowing the engagement protrusions 368 to be released from the groove 290, the reamer sleeve 350 may be translated along the longitudinal axis toward the first end of the shaft 114, 282 of the reamer 110, 280. The reamer sleeve 350 may be moved away from the cutting member 116, 284 to provide the space needed to remove bone debris that may build up on the reamer 110, 280 during reaming and to allow for verification that the desired amount of bone cartilage was removed. Further, the engagement protrusions 368 allow the reamer sleeve 350 to rotate freely with respect to the reamer 110, 280. Thus, as the reamer 230 rotates to ream a patient's bone, the reamer sleeve 350 may rotate freely or may remain stationary to prevent damage to the surrounding tissue. For example, if the reamer sleeve 350 contacts the adjacent bone the reamer sleeve 350 can remain stationary as the reamer 110, 280 continues to rotate to prevent damage to the bone or tissue contacted by the reamer sleeve 350.

Referring now to FIGS. 62-65, another backstop or reamer sleeve 400 is shown. The reamer sleeve 400 may include a base portion 402 and a collar portion 412. The base portion 402 may be of the type described above with reference to base portion 202. The base portion 402 may include a top surface 404, a bottom surface 406, at least one opening 408, and a rim 410, which may be the same or similar to the top surface 204, bottom surface 206, at least one opening 208 and rim 210, respectively, which will not be described again here for brevity sake.

Figure 62:
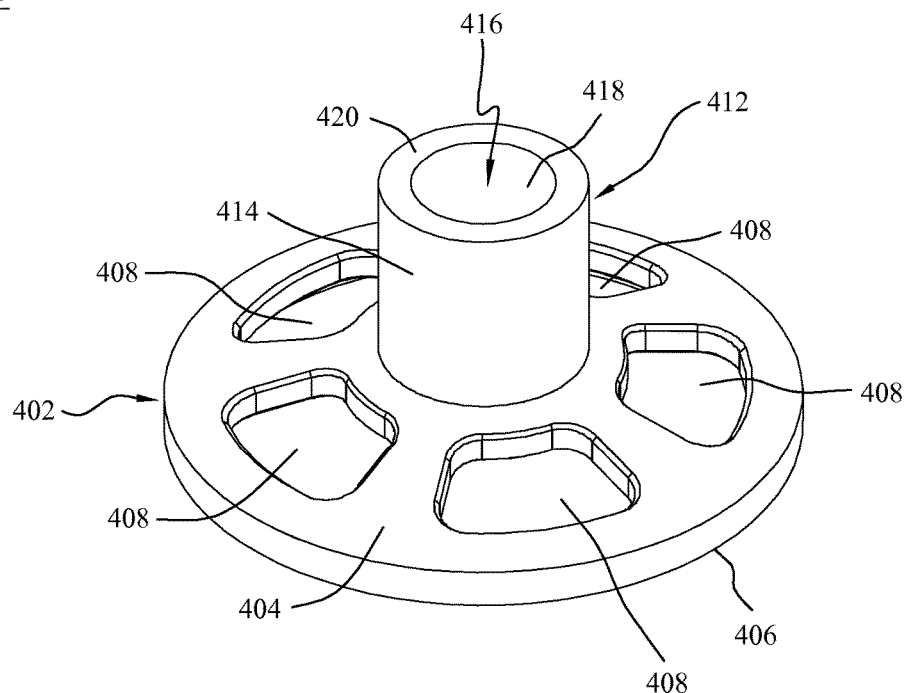
FIG. 62 is a top perspective view of another embodiment of a reamer sleeve, in accordance with an aspect of the present invention.
Figure 63:
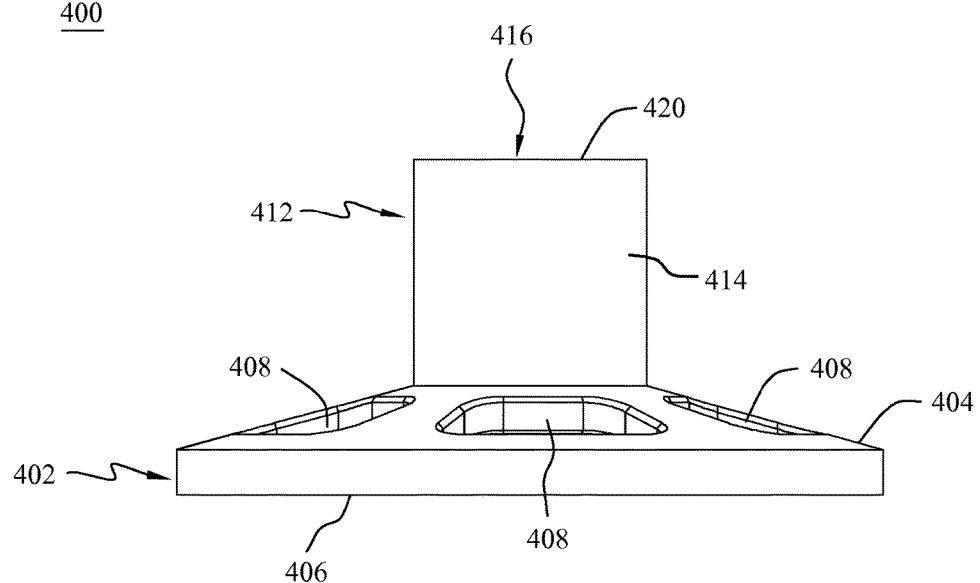
FIG. 63 is a side view of the reamer sleeve of FIG. 62, in accordance with an aspect of the present invention.
Figure 64:
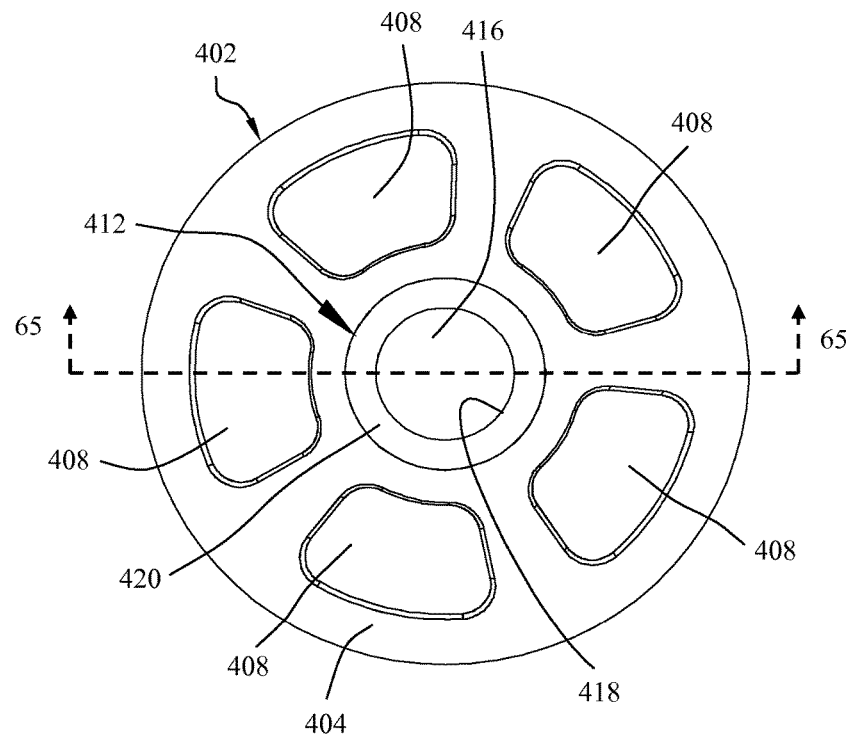
FIG. 64 is a top view of the reamer sleeve of FIG. 62, in accordance with an aspect of the present invention.
Figure 65:
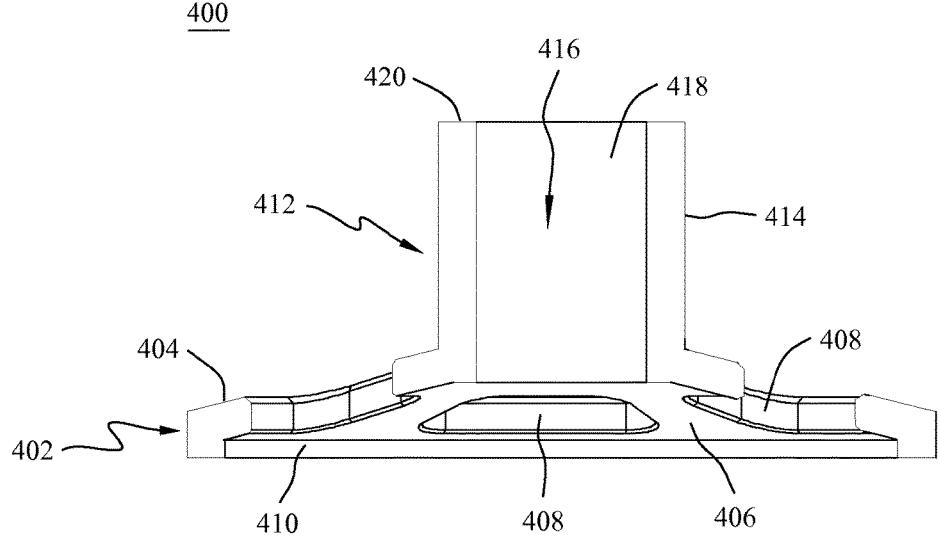
FIG. 65 is a cross-sectional view of the reamer sleeve of FIG. 62 taken along line 65-65 in FIG. 64, in accordance with an aspect of the present invention.
Figure 66:
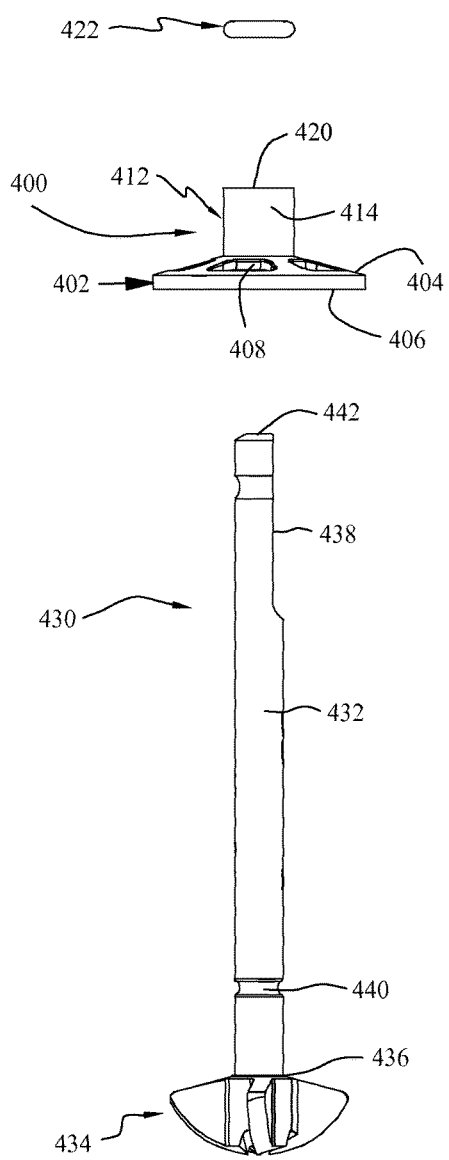
FIG. 66 is an exploded side view of a reamer assembly including the reamer sleeve of FIG. 62, with an aspect of the present invention.

The collar portion 412, as shown in FIGS. 62-65, may include a first end, a second end, and an opening 416 extending from the first end to the second end and forming an interior surface 418, as shown in FIGS. 62, 64, and 65. The second end of the collar portion 412 may be coupled to the base portion 402. The opening 416 may be sized to receive the shaft of a reamer, such that, the shaft cannot angle or tilt within the opening 416, as described in greater detail below.

Figure 67:
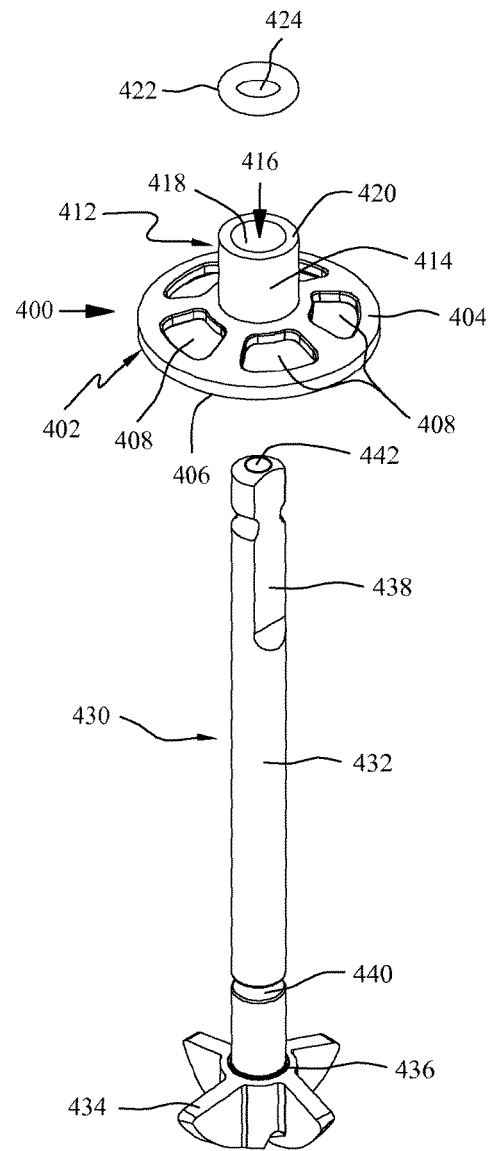
FIG. 67 is an exploded top perspective view of the reamer assembly of FIG. 66, in accordance with an aspect of the present invention.
Figures 68, 69:
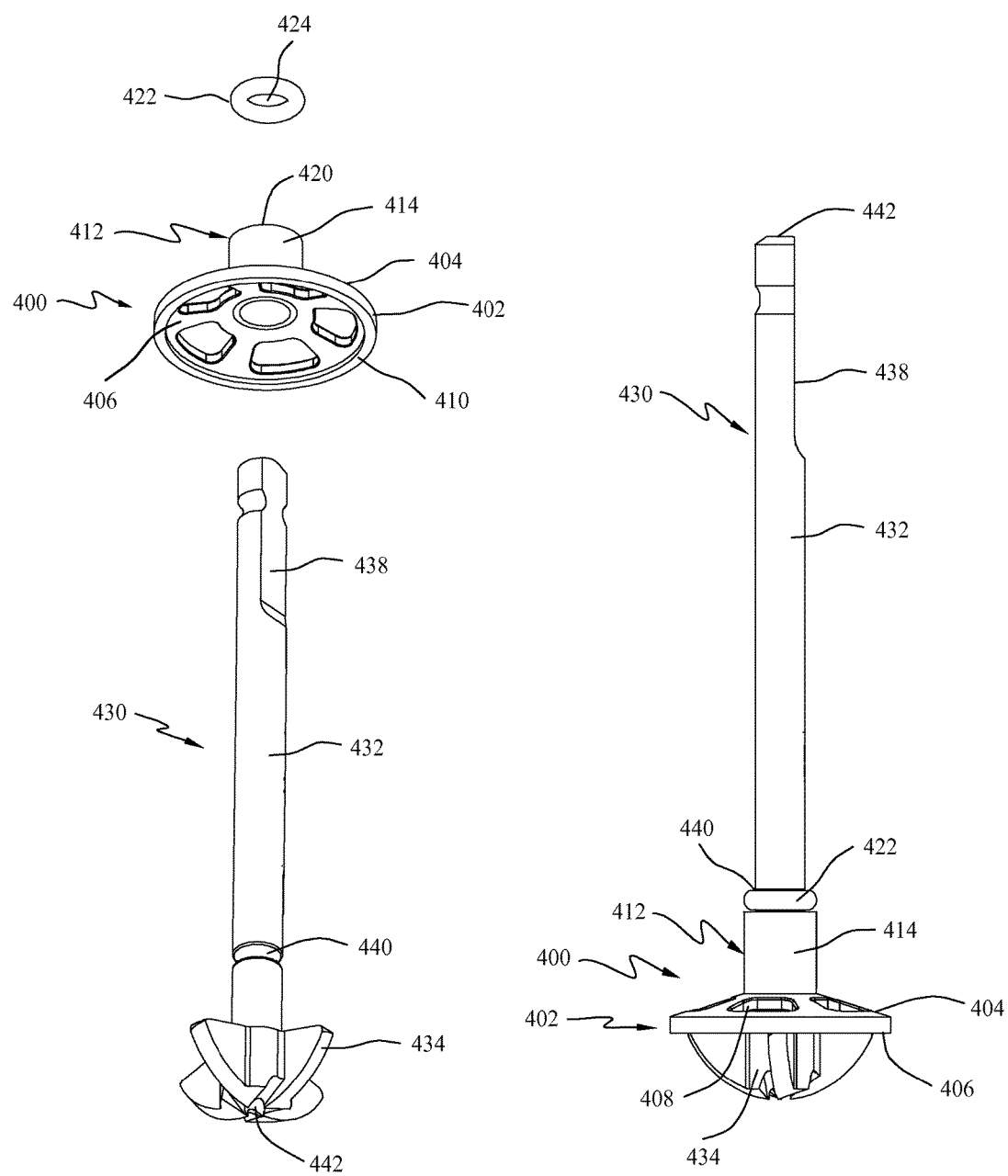
FIG. 68 is an exploded bottom perspective view of the reamer assembly of FIG. 66, in accordance with an aspect of the present invention.
FIG. 69 is a side view of the reamer assembly of FIG. 66, in accordance with an aspect of the present invention.
Figure 74:
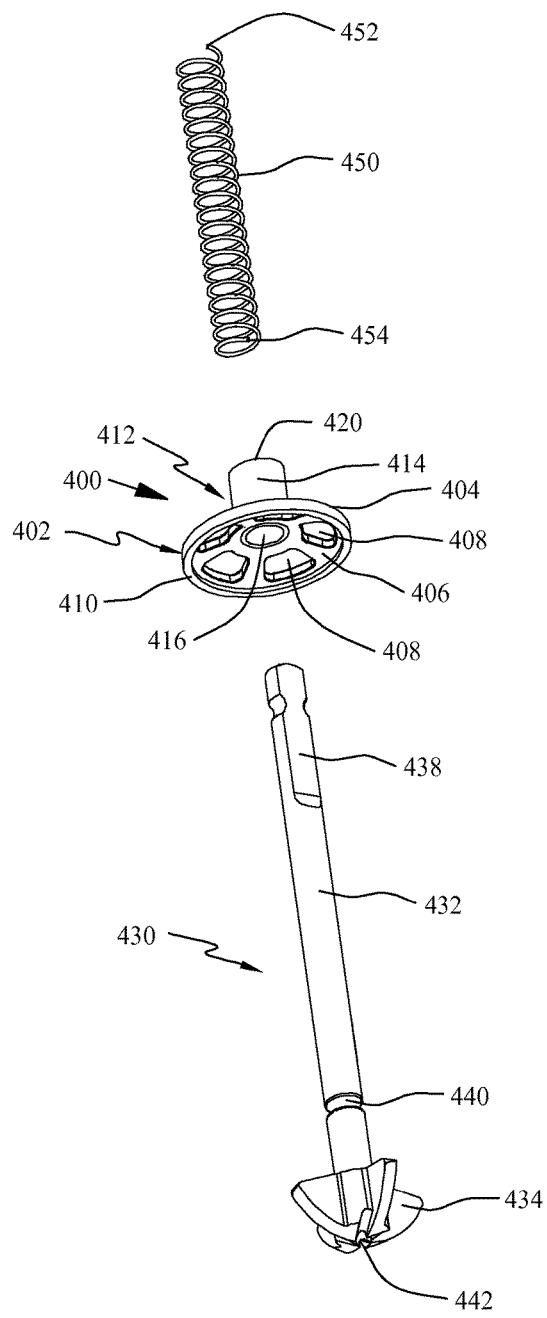
FIG. 74 is an exploded bottom perspective view of the reamer assembly of FIG. 72, in accordance with an aspect of the present invention.
Figure 75:
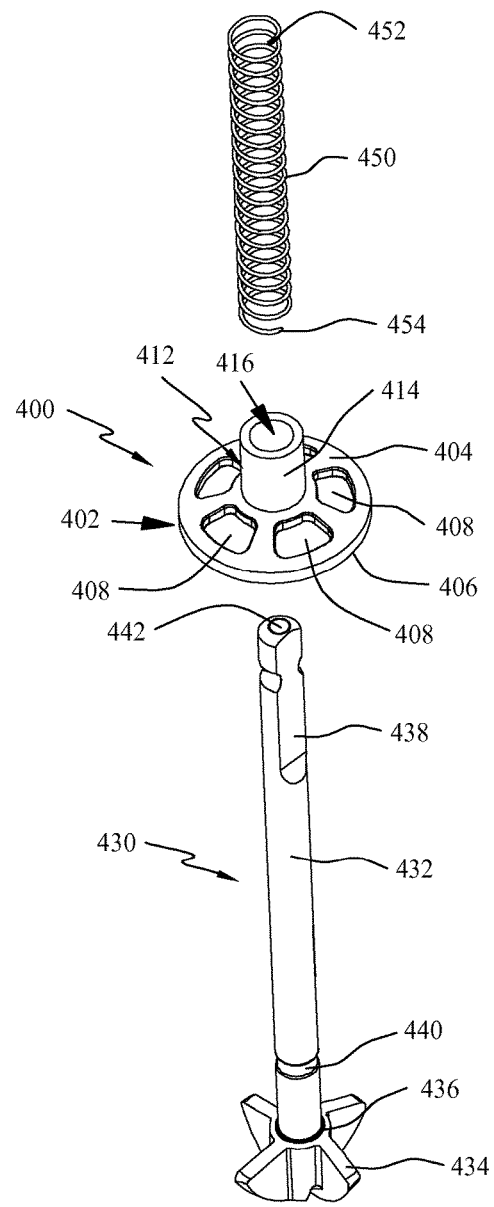
FIG. 75 is an exploded top perspective view of the reamer assembly of FIG. 72, in accordance with an aspect of the present invention.
Figure 81:
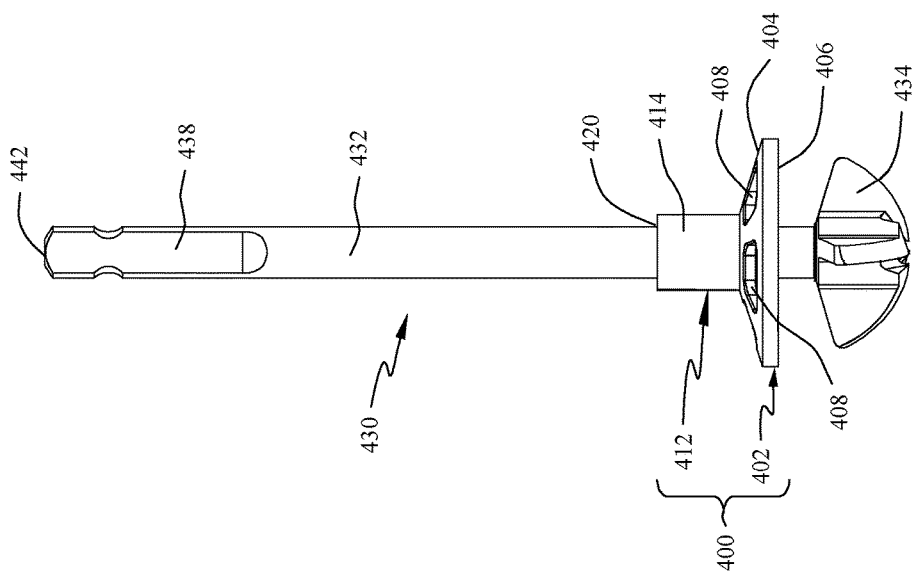
FIG. 81 is a side view of the reamer assembly of FIG. 79 with the reamer sleeve translated along the shaft of the reamer, in accordance with an aspect of the present invention.
Figure 80:
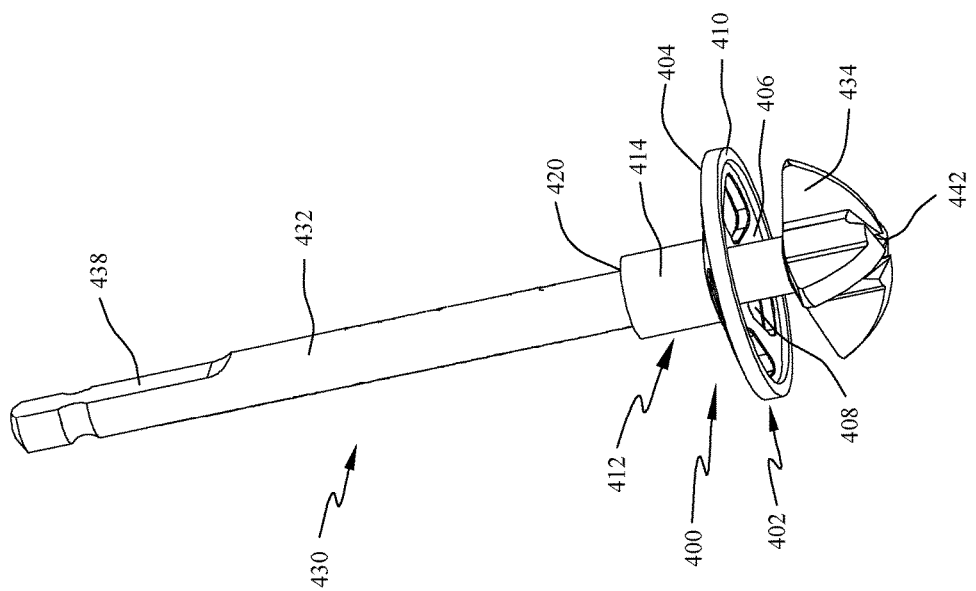
FIG. 80 is a perspective view of the reamer assembly of FIG. 79 with the reamer sleeve translated along the shaft of the reamer, in accordance with an aspect of the present invention.
Figure 84:
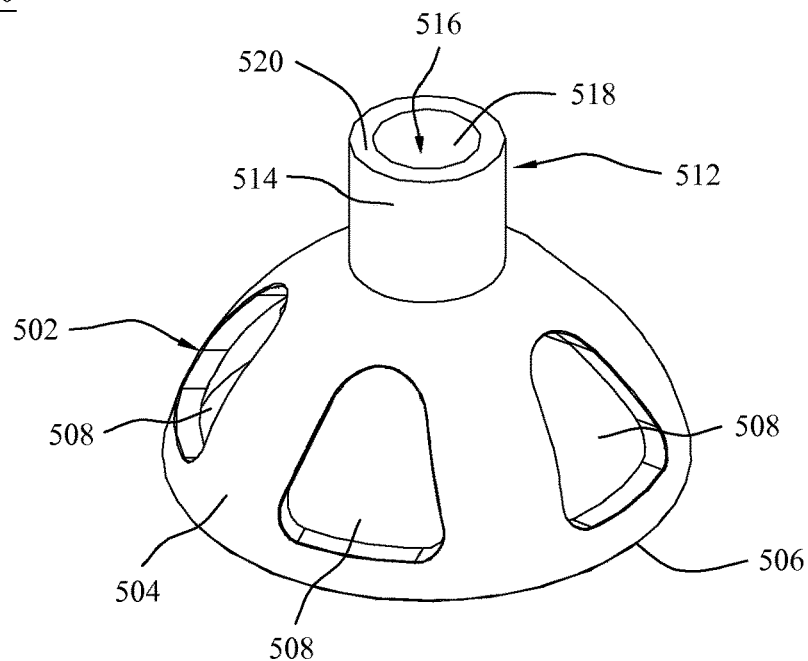
FIG. 84 is a top perspective view of an embodiment of a reamer sleeve, in accordance with an aspect of the present invention.

A reamer sleeve assembly including the reamer sleeve 400 and a male reamer 430 is shown in FIGS. 66-71. The reamer sleeve assembly may also include a securement mechanism 422. The male reamer 430 may be of the type described above with reference to male reamer 230. The reamer 430 may include a shaft 432 with a first end and a second end, an instrument mating surface 438, an opening 442, a groove 440, a cutting member 434, and a ring member 436, which may be the same or similar to shaft 232, instrument mating surface 238, opening 242, groove 240, cutting member 234, and ring member 236, respectively, which will not be described again here for brevity sake. The securement mechanism 422, as shown in FIGS. 67, 68, and 71, may include an opening 424 sized to fit over the shaft 432 of the reamer 430 and to engage the groove 440 to secure the reamer sleeve 400 over the cutting member 434 of the reamer 430. The securement mechanism 422 may be made of, for example, a deformable material to enable the securement mechanism 422 to stretch or deform slightly when placed over the shaft 432 and then fit snuggly in the groove 440. The securement mechanism 422 may also be sized to enable removal from the groove 440 to allow the surgeon to slide the reamer sleeve 400 away from the cutting member 434 of the reamer 430 to remove bone debris that may build up on the reamer 430 during reaming the bone and to also allow for verification that the desired amount of bone or cartilage was removed.

The reamer sleeve assembly may be formed by aligning the opening 416 of the reamer sleeve 400 with the shaft 432 of the reamer 430 and sliding the reamer sleeve 400 down the shaft 432 to a position above the cutting member 434. The reamer sleeve 400 may be spaced apart from the cutting member 434 by the ring member 436, such that the ring member 436 contacts the cutting member 434 on a first side and the reamer sleeve 400 on a second side and preventing the cutting member 434 and reamer sleeve 400 from coming into contact. In addition, the size of the opening 416 may be selected to enable translation of the reamer sleeve 400 up and down the shaft 432 of the reamer 430, while also preventing the reamer sleeve 400 from tilting and contacting the cutting member 434. Once the reamer sleeve 400 is positioned above the cutting member 434, the securement mechanism 422 may be inserted over the shaft 432 of the reamer 430. The opening 424 of the securement mechanism 422 may be aligned with the top of the shaft 432 and slid down the shaft 432 until the securement mechanism 422 engages the groove 440, as shown in FIGS. 69 and 71. Then the reamer sleeve assembly may be inserted into a drill (not shown) and the patient's bones reamed to remove tissue. The reamer sleeve 400 may be removed by disengaging the securement mechanism 422 from the groove 440 and sliding both the securement mechanism 422 and reamer sleeve 400 up the shaft 432 away from the cutting member 434. If the sleeve 400 is moved to remove tissue from the site or to check the site to determine if the desired amount of bone was reamed, then when additional reaming needs to be performed, the surgeon may slide the reamer sleeve 400 and securement mechanism 422 back down towards the cutting member 434 and into position above the cutting member 434 and into the groove 440, respectively. Alternatively, the securement mechanism 422 may be cut to remove it and if additional reaming is required, a new securement mechanism 422 may be inserted.

Referring now to FIGS. 72-78, another reamer sleeve assembly and the end of a drill 444 are shown. The reamer sleeve assembly may include a reamer sleeve 400, a male reamer 430, and a securement mechanism 450. The reamer sleeve 400 and male reamer 430 are described above in greater detail and will not be described again here for brevity sake. The securement mechanism 450 may be, for example, a spring member. The spring member 450 may include a first end 452 and a second end 454. The spring member 450 may be sized to fit around the shaft 432 of the reamer 430. The spring member 450 may be positioned between the reamer sleeve 430 and the end surface 446 of the drill 444. It is also contemplated that multiple springs could be used to obtain the desired force between the reamer sleeve 400 and the drill end 444. In another embodiment, the spring member 450 may be, for example, attached to the reamer sleeve 400 and the drill 444.

As shown in FIGS. 72-78, the reamer sleeve assembly may be formed by aligning the opening 416 of the reamer sleeve 400 with the shaft 432 of the reamer 430 and sliding the reamer sleeve 400 down the shaft 432 to a position above the cutting member 434. The reamer sleeve 400 may be spaced apart from the cutting member 434 by the ring member 436, such that the ring member 436 contacts the cutting member 434 on a first side and the reamer sleeve 400 on a second side and prevents the cutting member 434 and reamer sleeve 400 from coming into contact. Once the reamer sleeve 400 is positioned above the cutting member 434, the securement mechanism 422 may be inserted over the shaft 432 of the reamer 430. The securement mechanism 422 may be aligned with the top of the shaft 432 and slid down the shaft 432 until the second end 454 of the securement mechanism 422 contacts the top edge 420 of the reamer sleeve 400. Next the end of the reamer 430 with the instrument mating surface 438 may be aligned and inserted into the opening 448 in the drill end 444, as shown in FIGS. 72 and 78. As the drill end 444 engages the end of the reamer 430 and the instrument mating surface 438 is inserted into the opening 448, the drill end 444 translates down the shaft 432 of the reamer 430 toward the cutting member 434 until the mating surface 438 is fully engaged by the drill end 444. As the drill end 444 moves down the shaft 432, the surface 446 of the drill end 444 will contact the first end 452 of the securement mechanism 422. Once the reamer 430 is in the desired positioned in the drill end 444, the reamer 430 may be secured in the drill end 444.

The securement mechanism 422 will be sized to enable engagement with the drill end 444 at the first end 452 and with the reamer sleeve 400 at the second end 454. The securement mechanism 450 will also be sized to exert a force on the reamer sleeve 400 after insertion of the drill end 444 to keep the reamer sleeve 400 positioned over the cutting member 434 during reaming of a patient's bone and tissue.

The reamer sleeve 400 may be moved away from the cutting member 434 by applying force on the reamer sleeve 400 in the direction toward the drill end 444. Moving the reamer sleeve 400 up the shaft 432 of the reamer 430 allows the surgeon to remove tissue from the site or to check the site to determine if the desired amount of bone was reamed. Once the site has been cleaned and/or checked the reamer sleeve 400 may be lowered back down over the cutting member 434 of the reamer 430. After the desired amount of reaming is achieved, the drill end 444 of the drill may be removed from the shaft 432 by disengaging the instrument mating surface 438. Then the securement mechanism 450 and reamer sleeve 400 may be removed from the shaft 432 of the reamer 430.

Another reaming sleeve assembly is shown in FIGS. 79-83. The reaming sleeve assembly in FIGS. 79-83 includes a reamer sleeve 400 and a reamer 430. The reamer sleeve 400 and reamer 430 are of the type described above with reference to FIGS. 62-78 and will not be described again here for brevity sake. The collar portion 412 of the reamer sleeve 400 may be sized, for example, to allow the reamer sleeve 400 to translate up and down the shaft 432 of the reamer 430 when force is applied, but otherwise to sit in a position over the cutting member 434 of the reamer 430 during reaming of the patient's bones to protect surrounding tissue and bones, as shown in FIGS. 79-81 and 83. Alternatively, the collar portion 412 may be sized, for example, to slide up and down the shaft 432 of the reamer 430 and to prevent the reamer sleeve 400 from tilting during reaming of the patient's bones.

Referring now to FIGS. 84-87, another backstop or reamer sleeve 500 is shown. The reamer sleeve 500 may include a base portion 502 and a collar portion 512. The base portion 502 may be of the type described above with reference to base portion 252. The base portion 502 may include a top surface 504, a bottom surface 506, and at least one opening 508, which may be the same or similar to the top surface 254, bottom surface 256, and at least one opening 258, respectively, which will not be described again here for brevity sake.

Figure 85:
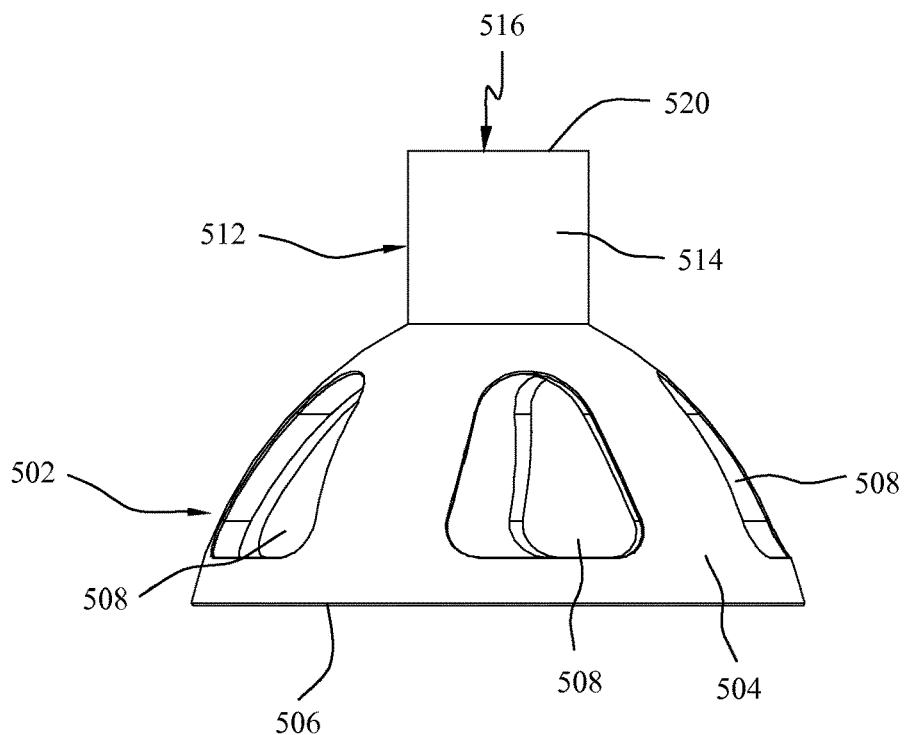
FIG. 85 is a side view of the reamer sleeve of FIG. 84, in accordance with an aspect of the present invention.
Figure 86:
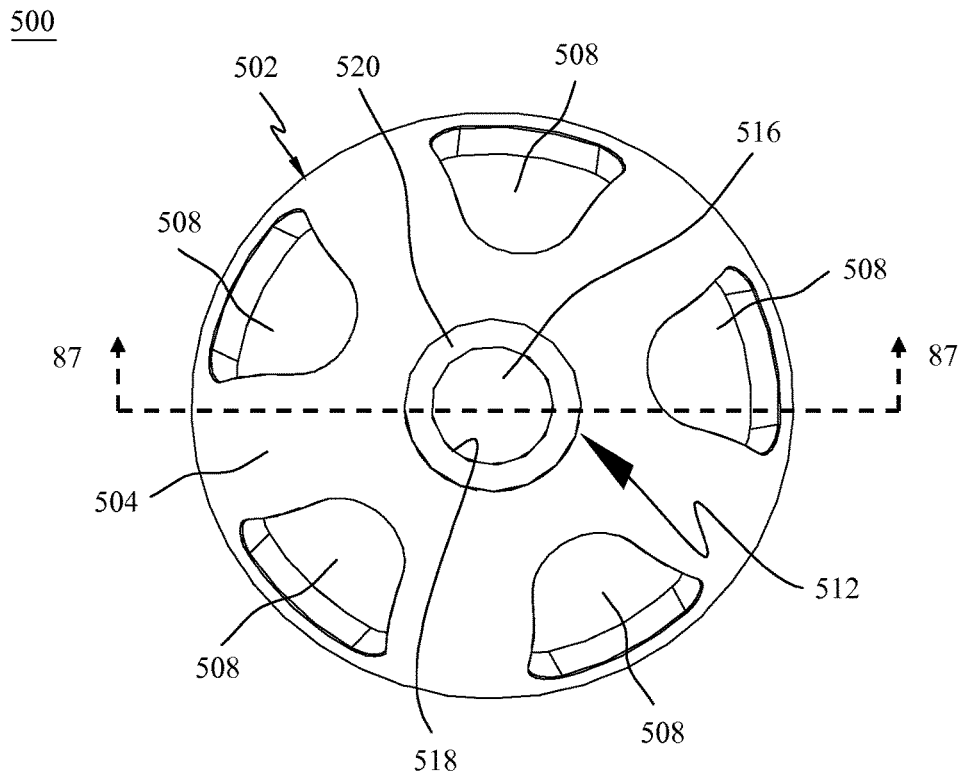
FIG. 86 is a top view of the reamer sleeve of FIG. 84, in accordance with an aspect of the present invention.
Figure 87:
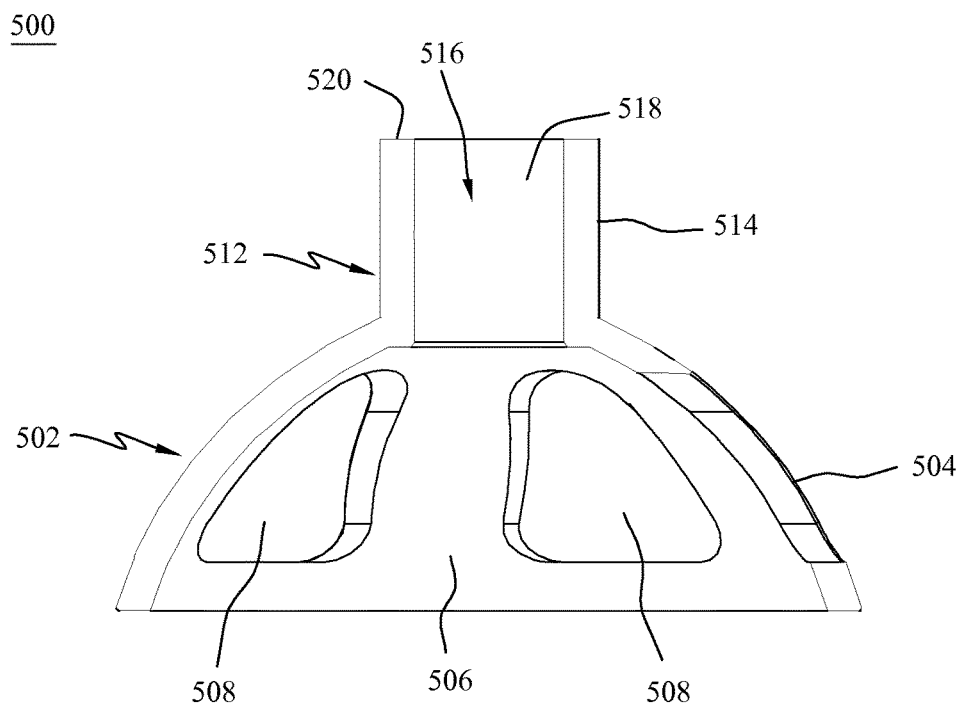
FIG. 87 is a cross-sectional view of the reamer sleeve of FIG. 84 taken along line 87-87 in FIG. 86, in accordance with an aspect of the present invention.
Figures 88, 89:
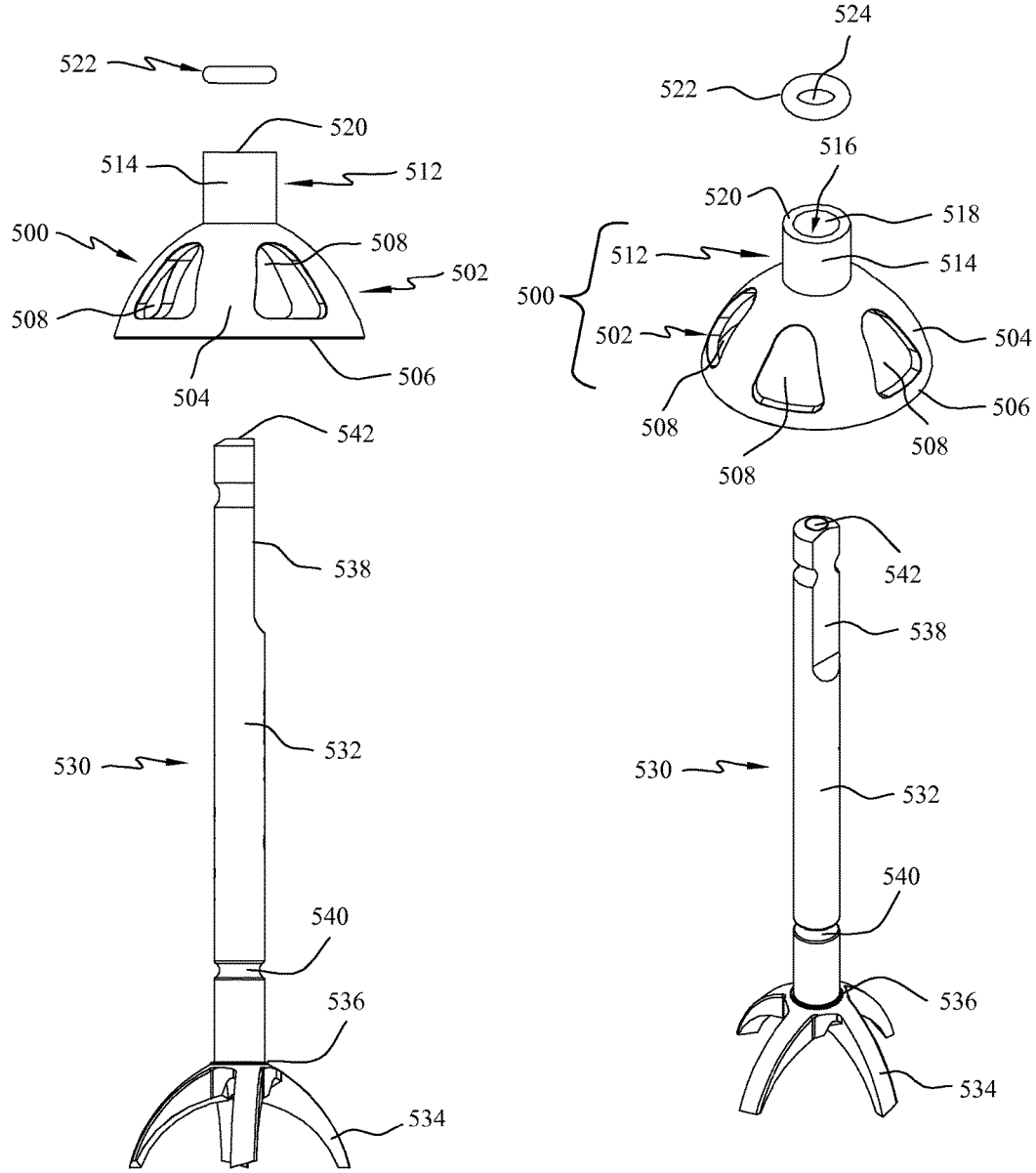
FIG. 88 is an exploded side view of a reamer assembly including the reamer sleeve of FIG. 84, in accordance with an aspect of the present invention.
FIG. 89 is an exploded top perspective view of the reamer assembly of FIG. 88, in accordance with an aspect of the present invention.

The collar portion 512, as shown in FIGS. 84-87, may include a first end, a second end, and an opening 516 extending from the first end to the second end and forming an interior surface 518, as shown in FIGS. 85, 86, and 87. The second end of the collar portion 512 may be coupled to the base portion 502. The opening 516 may be sized to receive the shaft of a reamer, such that, the shaft cannot angle or tilt within the opening 516, as described in greater detail below.

A reamer sleeve assembly including the reamer sleeve 500 and a female reamer 530 is shown in FIGS. 88-93. The reamer sleeve assembly may also include a securement mechanism 522. The female reamer 530 may be of the type described above with reference to female reamer 280. The reamer 530 may include a shaft 532 with a first end and a second end, an instrument mating surface 538, an opening 542, a groove 540, a cutting member 534, and a ring member 536, which may be the same or similar to shaft 282, instrument mating surface 288, opening 292, groove 290, cutting member 284, and ring member 286, respectively, which will not be described again here for brevity sake.

The securement mechanism 522, as shown in FIGS. 88-93, may be of the type described above with reference to securement mechanism 422. The securement mechanism 522 may have an opening 524, which may be the same or similar to opening 424. The opening 524 of the securement mechanism 522 may be sized to fit over the shaft 532 of the reamer 530 and to engage the groove 540 to secure the reamer sleeve 500 above the cutting member 534 of the reamer 530. The securement mechanism 522 may be made of, for example, a deformable material to enable the securement mechanism 522 to stretch or deform slightly when placed over the shaft 532 and then fit snuggly in the groove 540. The securement mechanism 522 may also be sized to enable removal from the groove 540, as described above in greater detail with respect to FIGS. 66-71 and which will not be described again here for brevity sake.

The reamer sleeve assembly, as shown in FIGS. 88-93, may be formed by aligning the opening 516 of the reamer sleeve 500 with the shaft 532 of the reamer 530 and sliding the reamer sleeve 500 down the shaft 532 to a position above the cutting member 534. The reamer sleeve 500 may be spaced apart from the cutting member 534 by the ring member 536, which contacts the cutting member 534 on a first side and the reamer sleeve 500 on a second side to prevent the cutting member 534 from contacting the reamer sleeve 500. In addition, the size of the opening 516 may allow translation of the reamer sleeve 500 up and down the shaft 532 of the reamer 530, while preventing the reamer sleeve 500 from tilting and contacting the cutting member 534. Once the reamer sleeve 500 is positioned above the cutting member 534, the opening 524 of the securement mechanism 522 may be aligned and inserted over the shaft 532 of the reamer 530 and slid down the shaft 532 until the securement mechanism 522 engages the groove 540, as shown in FIGS. 91 and 93. The reamer sleeve assembly may then be inserted into a drill (not shown) and the patient's bones reamed to remove tissue. The reamer sleeve 500 may be removed by disengaging the securement mechanism 522 from the groove 540 and sliding both the securement mechanism 522 and reamer sleeve 500 up the shaft 532 away from the cutting member 534. If the sleeve 500 is moved to remove tissue from the site or to check the site to determine if the desired amount of bone was reamed, then when additional reaming needs to be performed, the surgeon may slide the reamer sleeve 500 and securement mechanism 522 back down and into position above the cutting member 534. Alternatively, the securement mechanism 522 may be cut to remove it and if additional reaming is required a new securement mechanism 522 may be inserted.

Referring now to FIGS. 94-100, another reamer sleeve assembly and the end of a drill 544 are shown. The reamer sleeve assembly may include a reamer sleeve 500, a female reamer 530, and a securement mechanism 550. The reamer sleeve 500 and female reamer 530 are described above in greater detail and will not be described again here for brevity sake. The securement mechanism 550 may be, for example, a spring member. The spring member 550 may include a first end 552 and a second end 554. The spring member 550 may be sized to fit around the shaft 532 of the reamer 530. The spring member 550 may be positioned between the reamer sleeve 530 and the end surface 546 of the drill 544. The spring member 550 may be, for example, attached to the reamer sleeve 500 and the drill 544. The securement mechanism 522 is of the type described above with reference to securement mechanism 422 and will not be described again here for brevity sake.

Figure 94:
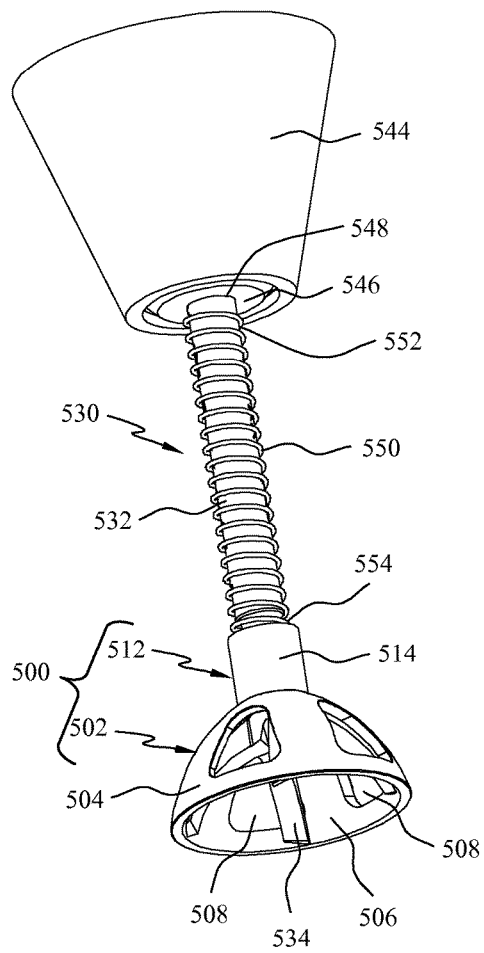
FIG. 94 is a perspective view of another reamer sleeve assembly attached to the end portion of a drill and including the reamer sleeve of FIG. 84, in accordance with an aspect of the present invention.
Figure 95:
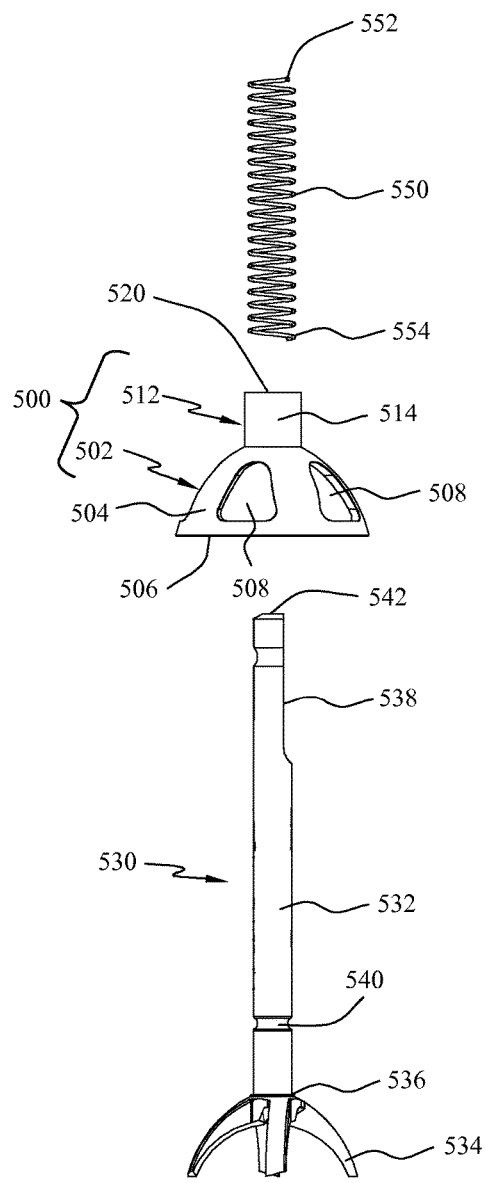
FIG. 95 is an exploded side view of the reamer sleeve assembly of FIG. 94, in accordance with an aspect of the present invention.
Figure 99:
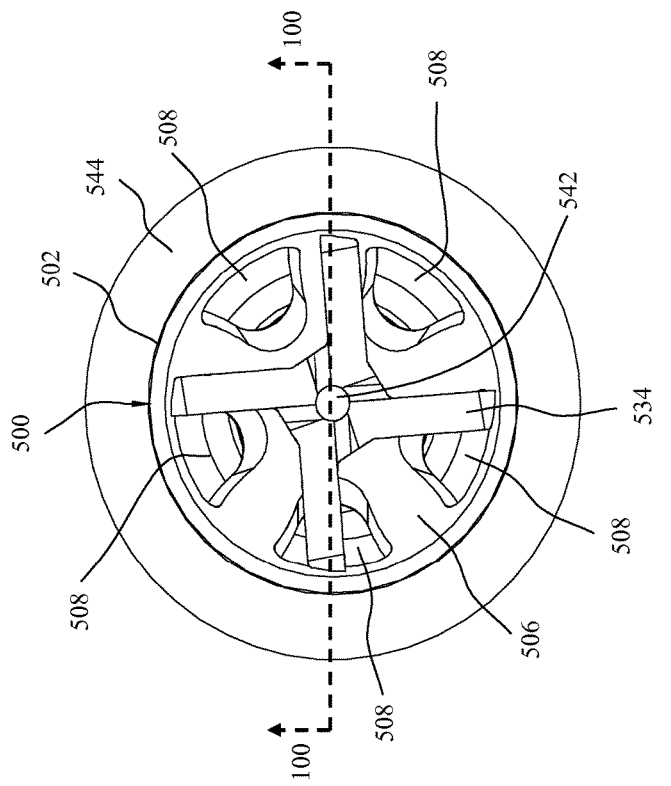
FIG. 99 is a bottom view of the reamer sleeve assembly of FIG. 94, in accordance with an aspect of the present invention.
Figure 98:
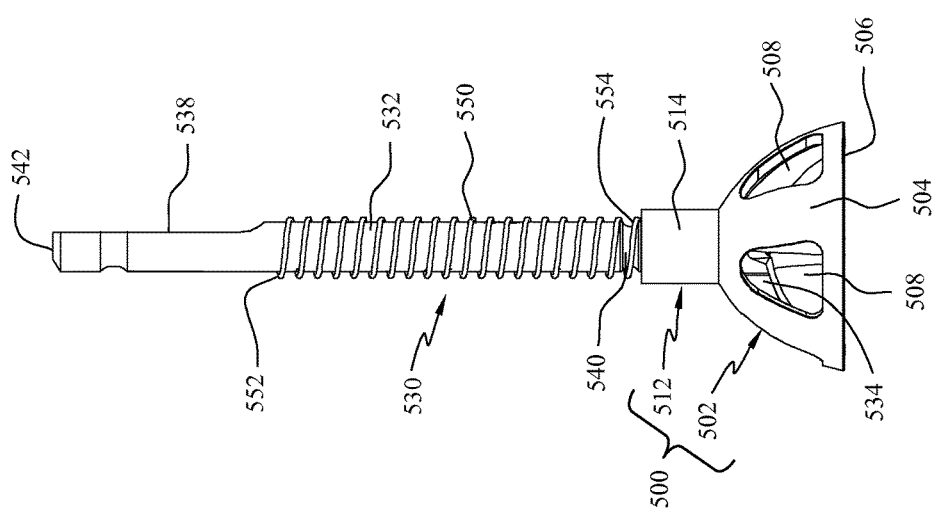
FIG. 98 is a side view of the reamer sleeve assembly of FIG. 94, in accordance with an aspect of the present invention.
Figure 103:
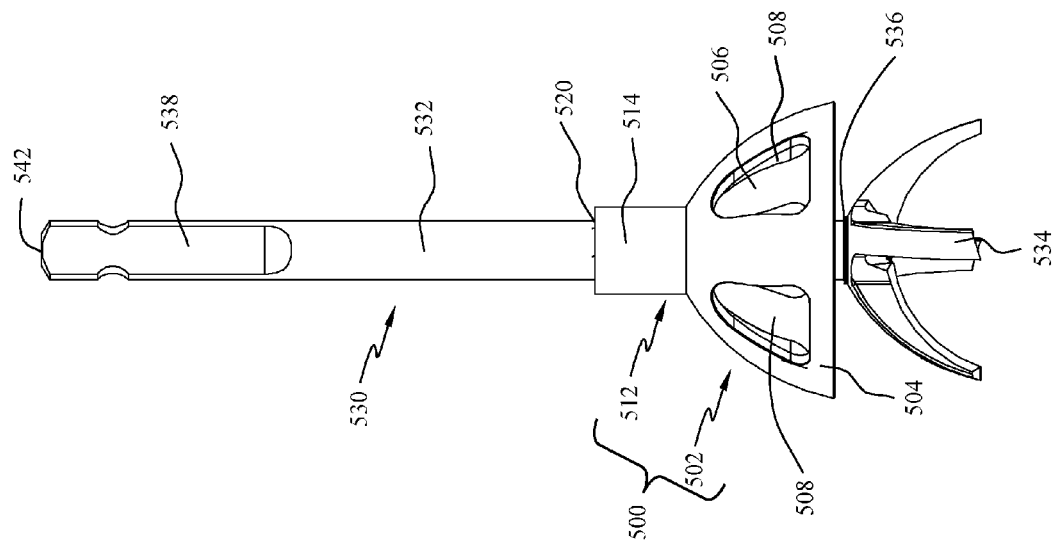
FIG. 103 is a side view of the reamer sleeve assembly of FIG. 101 with the reamer sleeve translated along the shaft of the reamer, in accordance with an aspect of the present invention.
Figure 102:
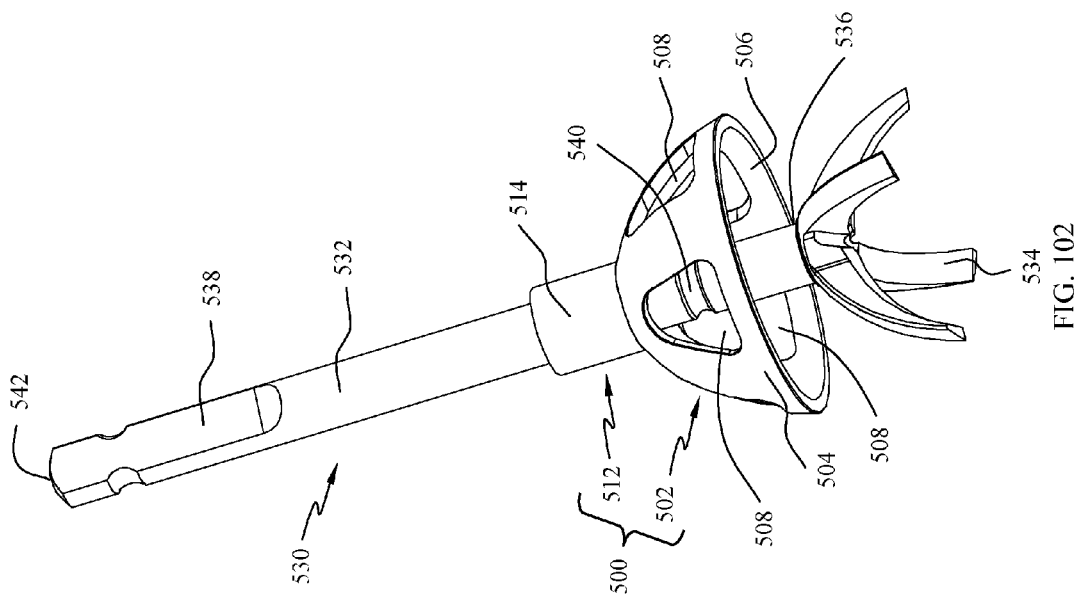
FIG. 102 is a perspective view of the reamer sleeve assembly of FIG. 101 with the reamer sleeve translated along the shaft of the reamer, in accordance with an aspect of the present invention.
Figure 105:
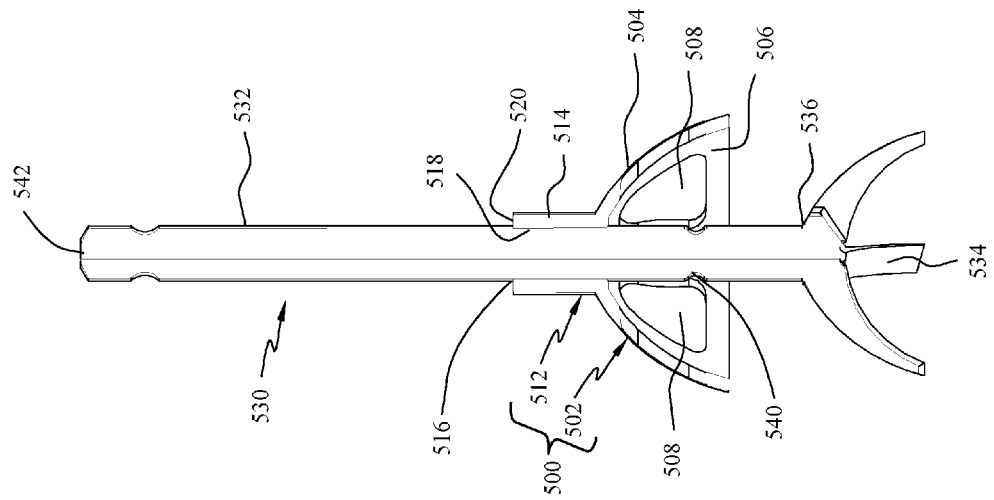
FIG. 105 is a cross-sectional view of the reamer sleeve assembly of FIG. 101 taken along line 105-105 in FIG. 104 with the reamer sleeve translated along the shaft of the reamer, in accordance with an aspect of the present invention.
Figure 104:
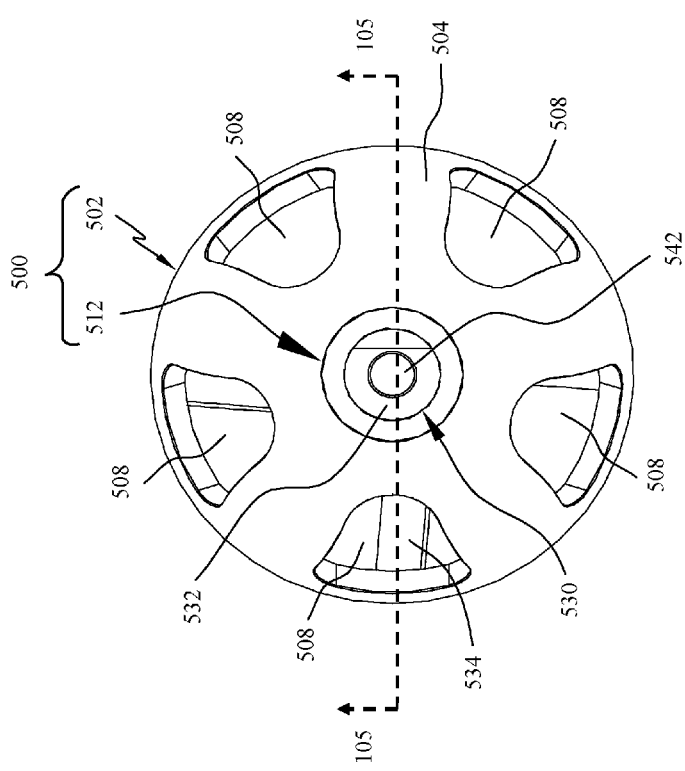
FIG. 104 is a top view of the reamer sleeve assembly of FIG. 101, in accordance with an aspect of the present invention.

As shown in FIGS. 94-100, the reamer sleeve assembly may be formed by aligning the opening 516 of the reamer sleeve 500 with the shaft 532 of the reamer 530 and sliding the reamer sleeve 500 down the shaft 532 to a position above the cutting member 534. The reamer sleeve 500 may be spaced apart from the cutting member 534 by the ring member 536, as described in greater detail above with respect to ring member 436 and which will not be described again here for brevity sake. Once the reamer sleeve 500 is positioned above the cutting member 534, the securement mechanism 522 may be aligned and inserted over the shaft 532 of the reamer 530 and translated until the second end 554 of the securement mechanism 522 contacts the top edge 520 of the reamer sleeve 500. Next the instrument mating surface 538 may be aligned and inserted into the opening 548 in the drill end 544, as shown in FIGS. 94 and 100. As the instrument mating surface 538 is inserted into the opening 548, the drill end 544 translates down the shaft 532 of the reamer 530 toward the cutting member 534 until the mating surface 538 is fully engaged by the drill end 544. As the drill end 544 moves down the shaft 432, the surface 546 of the drill end 544 contacts the first end 552 of the securement mechanism 522. Once in position, the reamer 530 is secured to the drill end 544.

The reamer sleeve 500 may be moved away from the cutting member 534 by applying force on the reamer sleeve 500 in the direction toward the drill end 544. Moving the reamer sleeve 500 up the shaft 532 of the reamer 530 allows the surgeon to remove tissue from the site or to check the site to determine if the desired amount of bone was reamed. Once the site has been cleaned and/or checked the reamer sleeve 500 may be lowered back down over the cutting member 534 of the reamer 530. After the desired amount of reaming is achieved, the drill end 544 of the drill may be removed from the shaft 532 by disengaging the instrument mating surface 538. Then the securement mechanism 550 and reamer sleeve 500 may be removed from the shaft 532 of the reamer 530.

Another reaming sleeve assembly is shown in FIGS. 101-105 and includes a reamer sleeve 500 and a reamer 530. The reamer sleeve 500 and reamer 530 are of the type described above with reference to FIGS. 84-100 and will not be described again here for brevity sake. The collar portion 512 of the reamer sleeve 500 may be sized, for example, to allow it to translate up and down the shaft 532 of the reamer 530 when force is applied, but to sit in position over the cutting member 534 of the reamer 530 during reaming of the patient's bones to protect surrounding tissue and bones, as shown in FIGS. 101-103 and 105. Alternatively, the collar portion 512 may be sized, for example, to slide up and down the shaft 532 of the reamer 530 and to prevent the reamer sleeve 500 from tilting during reaming of the patient's bones. It is also contemplated that another securement mechanism (not shown) may be used to secure the reamer sleeve 500 to the reamer 530 of FIGS. 101-105, for example, a pin, clip, or like fastener.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method of device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A bone reamer assembly, comprising:
  a bone reamer comprising:
    a shaft with a proximal end and a distal end;
    a cutting member coupled to the distal end of the shaft comprising a plurality of curved blades defining concave inner surfaces to enable cutting of a convex bone surface; and
    an annular groove in the shaft positioned near the distal end of the shaft;
  a reamer sleeve removably coupled to the annular groove of the reamer for protecting surrounding tissue from being cut by the reamer, wherein the reamer sleeve comprises:
    a base portion having a top surface and a concave bottom surface, the base portion comprising:
      a plurality of through openings extending from the top surface to the bottom surface, the plurality of through openings each including an edge, and wherein the edges are blunt; and
    a securement mechanism extending away from the top surface of the base portion, the securement mechanism comprising:
      a monolithic cylindrical body coupled to and extending away from the top surface of the base along a longitudinal axis and including an opening extending therethrough along the longitudinal axis to the bottom surface of the base portion, the cylindrical body comprising:
        a solid collar portion defining a proximal end of the cylindrical body;
        a solid distal ring portion defining a distal end of the cylindrical body;
        at least one deformable member extending between the collar portion and the distal ring portion of the cylindrical body;
        at least one aperture extending through the cylindrical body portion from an exterior surface thereof to the opening enclosed between the collar portion and the distal ring portion and adjacent to the at least one deformable member; and
        at least one engagement protrusion extending from an interior surface of the least one deformable member into the opening to engage the annular groove in the shaft of the bone reamer to couple the reamer sleeve to the annular groove of the bone reamer, wherein the plurality of through openings of the base portion are positioned circumferentially around the cylindrical body of the securement mechanism, wherein the top surface and the bottom surface of the base portion terminate at a peripheral rim, and wherein the peripheral rim is circumferential and has a smooth distal surface; and an instrument including a coupling portion for receiving the proximal end of the bone reamer, wherein the coupling of the reamer sleeve to the annular groove at the distal end of the shaft adjacent to the cutting member allows for relative rotation of the reamer sleeve about a longitudinal axis of the shaft and prevents axial translation along the longitudinal axis of the shaft, and wherein the reamer sleeve rotates independent of the instrument and the bone reamer;

wherein the base portion of the reamer sleeve extends distally beyond an outer edge of a top surface of the cutting member.

2. The bone reamer assembly of claim 1, wherein the reamer, further comprises:

a ring member positioned circumferentially around the shaft where the cutting member couples to the shaft.

3. The bone reamer assembly of claim 1, wherein the collar portion extends circumferentially about the shaft of the bone reamer when the reamer sleeve and the bone reamer are coupled together.

4. The bone reamer assembly of claim 3, wherein the base portion of the reamer sleeve is planar and angled as it extends away from the securement mechanism.

5. The bone reamer assembly of claim 3, wherein the base portion is curved as it extends away from the securement mechanism.

6. The bone reamer assembly of claim 1, wherein the securement mechanism removeably secures the reamer sleeve to the shaft of the reamer.

7. The bone reamer assembly of claim 1, wherein the opening of the reamer sleeve is removably coupled to the shaft of the reamer and the opening on the bottom surface of the base portion is inserted over the proximal end of the shaft.

8. The bone reamer assembly of claim 1, wherein the at least one aperture has a length and a width, the length extends along the longitudinal axis of the cylindrical body of the securement mechanism, and the length is larger than the width.

9. The bone reamer assembly of claim 1, wherein the at least one engagement protrusion is positioned on the at least one deformable member near a midpoint of the length of the at least one aperture.

10. The bone reamer assembly of claim 1, wherein the cylindrical body of the securement mechanism further comprises:

at least one side member extending between the collar portion and the distal ring portion of the cylindrical body; and wherein the at least one deformable member and the at least one side member are positioned adjacent to and separated by the at least one aperture, and wherein the at least one deformable member and the at least one side member are recessed in from an exterior surface of the collar portion and an exterior surface of the distal ring portion.

11. The bone reamer assembly of claim 1, wherein the at least one deformable member deforms when the engagement protrusion contacts the exterior surface of the shaft of the bone reamer until the engagement protrusion engages the annular groove in the shaft of the bone reamer preventing axial translation along the longitudinal axis of the shaft and allowing for relative rotation of the reamer sleeve.

\* \* \* \* \*

UNITED STATES PATENT AND TRADEMARK OFFICE
CERTIFICATE OF CORRECTION

PATENT NO. : 10,159,499 B2
APPLICATION NO. : 14/458722
DATED : December 25, 2018
INVENTOR(S) : Dacosta et al.

Page 1 of 1

It is certified that error appears in the above-identified patent and that said Letters Patent is hereby corrected as shown below:

In the Claims

Column 28, Line 44: Claim 1, Delete "base along a" and insert -- base portion along a --

Signed and Sealed this
Twelfth Day of February, 2019

Andrei Iancu
*Director of the United States Patent and Trademark Office*

UNITED STATES PATENT AND TRADEMARK OFFICE
CERTIFICATE OF CORRECTION

PATENT NO. : 10,159,499 B2  
APPLICATION NO. : 14/458722  
DATED : December 25, 2018  
INVENTOR(S) : Dacosta et al.

Page 1 of 1

It is certified that error appears in the above-identified patent and that said Letters Patent is hereby corrected as shown below:

On the Title Page

Item (73): Assignee: Delete "PARAGON 26, INC." and Insert -- "PARAGON 28, INC." --

This certificate supersedes the Certificate of Correction issued February 12, 2019.

Signed and Sealed this
First Day of September, 2020

Andrei Iancu
*Director of the United States Patent and Trademark Office*